US012601018B2

(12) United States Patent
Green et al.

(10) Patent No.: US 12,601,018 B2
(45) Date of Patent: Apr. 14, 2026

(54) DETECTION OF SARS-CoV-2 USING RNA MULTI-ARM JUNCTION LOGIC GATES

(71) Applicants: Alexander Green, Chestnut Hill, MA (US); Duo Ma, Tempe, AZ (US)

(72) Inventors: Alexander Green, Chestnut Hill, MA (US); Duo Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 882 days.

(21) Appl. No.: 17/822,213

(22) Filed: Aug. 25, 2022

(65) Prior Publication Data

US 2023/0147004 A1 May 11, 2023

Related U.S. Application Data

(60) Provisional application No. 63/237,012, filed on Aug. 25, 2021.

(51) Int. Cl.

| | |
|---|---|
| *C12Q 1/00* | (2006.01) |
| *C12Q 1/68* | (2018.01) |
| *C12Q 1/70* | (2006.01) |
| *C12Q 1/6851* | (2018.01) |
| *C12Q 1/6897* | (2018.01) |

(52) U.S. Cl.
CPC ........... *C12Q 1/701* (2013.01); *C12Q 1/6851* (2013.01); *C12Q 1/6897* (2013.01)

(58) Field of Classification Search
None
See application file for complete search history.

(56) References Cited

U.S. PATENT DOCUMENTS

| | | |
|---|---|---|
| 8,841,438 B2 | 9/2014 | Tenenbaum et al. |
| 9,534,224 B2 | 1/2017 | Collins et al. |
| 10,941,401 B2 | 3/2021 | Green et al. |
| 2019/0218624 A1 | 7/2019 | Green et al. |
| 2021/0102237 A1 | 4/2021 | Gasiunaite et al. |

OTHER PUBLICATIONS

Koksaldi et al. SARS-CoV-2 Detection with De Novo-Designed Synthetic Riboregulators. Anal. Chem. 2021, 93, 9719-9727.*
Duo Ma, RNA-Based Computing Devices for Intracellular and Diagnostic Applications—Dissertation Presented in Partial Fulfillment of the Requirements for the Degree Doctor of Philosophy, ProQuest 22584705, Published by ProQuest LLC (2019).*
Kim et al. De novo-designed translation-repressing riboregulators for multi-input cellular logic. Nature Chemical Biology, 2019, 15: 1173-1182.*
A. A. Green, "Synthetic bionanotechnology: synthetic biology finds a toehold in nanotechnology," Emerg Top Life Sci 3, 507-516 (2019).

A. A. Green, J. Kim, D. Ma, P. A. Silver, J. J. Collins & P. Yin, "Complex cellular logic computation using ribocomputing devices," Nature 548, 117-121 (2017).
A. A. Green, P. A. Silver, J. J. Collins & P. Yin, "Toehold switches: de-novo-designed regulators of gene expression," Cell 159, 925-939 (2014).
A. Serganov & E. Nudler, "A decade of riboswitches," Cell 152, 17-24 (2013).
A. Wittmann & B. Suess, "Engineered riboswitches: Expanding researchers' toolbox with synthetic RNA regulators," FEBS Letters 586, 2076-2083 (2012).
B. Groves, Y.-J. Chen, C. Zurla, S. Pochekailov, J. L. Kirschman, P. J. Santangelo & G. Seelig, "Computing in mammalian cells with nucleic acid strand exchange," Nature Nanotechnology 11, 287-294 (2016).
B. M. Lunde, C. Moore & G. Varani, "RNA-binding proteins: modular design for efficient function," Nat Rev Mol Cell Biol 8, 479-490 (2007).
Broughton, J. P. et al. CRISPR-Cas12-based detection of SARS-CoV-2. Nat. Biotechnol. 38, 870-874 (2020).
C. Geary, P. W. K. Rothemund & E. S. Andersen, "A single-stranded architecture for cotranscriptional folding of RNA nanostructures," Science 345, 799-804 (2014).
C. J. Delebecque, A. B. Lindner, P. A. Silver & F. A. Aldaye, "Organization of Intracellular Reactions with Rationally Designed RNA Assemblies," Science 333, 470-474 (2011).
Chen, J. S. et al. CRISPR-Cas 12a target binding unleashes indiscriminate single-stranded DNase activity. Science 360, 436-439 (2018).
D. Han, X. Qi, C. Myhrvold, B. Wang, M. Dai, S. Jiang, M. Bates, Y. Liu, B. An, F. Zhang, H. Yan & P. Yin, "Single-stranded DNA and RNA origami," Science 358, eaao2648 (2017).
D. Jasinski, F. Haque, D. W. Binzel & P. Guo, "Advancement of the Emerging Field of RNA Nanotechnology," ACS Nano 11, 1142-1164 (2017).
D. Liu, C. W. Geary, G. Chen, Y. Shao, M. Li, C. Mao, E. S. Andersen, J. A. Piccirilli, P. W. K. Rothemund & Y. Weizmann, "Branched kissing loops for the construction of diverse RNA homooligomeric nanostructures," Nature Chemistry (2020).
D. Ma, L. Shen, K. Wu, C. W. Diehnelt & A. A. Green, "Low-cost detection of norovirus using paper-based cell-free systems and synbody-based viral enrichment," Synth Biol (Oxf) 3, ysy018 (2018).
D. Shu, Y. Shu, F. Haque, S. Abdelmawla & P. Guo, "Thermodynamically stable RNA three-way junction for constructing multifunctional nanoparticles for delivery of therapeutics," Nature Nanotechnology 6, 658-667 (2011).
E. A. Doherty & J. A. Doudna, "Ribozyme structures and mechanisms," Annu. Rev. Biochem. (2000). 69:597-615.
F. Hong, D. Ma, K. Wu, L. A. Mina, R. C. Luiten, Y. Liu, H. Yan & A. A. Green, "Precise and Programmable Detection of Mutations Using Ultraspecific Riboregulators," Cell 180, 1018-1032 (2020).

(Continued)

*Primary Examiner* — Nianxiang Zou
(74) *Attorney, Agent, or Firm* — Quarles & Brady, LLP

(57) ABSTRACT

The present invention provides loop-mediated riboregulators for the detection of SARS-CoV-2. Also provided are DNA constructs encoding the loop-mediated riboregulators and methods of using the loop-mediated riboregulators to detect the presence of SARS-CoV-2 in a sample.

20 Claims, 20 Drawing Sheets

Specification includes a Sequence Listing.

(56)         References Cited

OTHER PUBLICATIONS

F. J. Isaacs, D. J. Dwyer, C. Ding, D. D. Pervouchine, C. R. Cantor & J. J. Collins, "Engineered riboregulators enable post-transcriptional control of gene expression," Nat Biotechnol 22, 841-847 (2004).

G. Chatterjee, Y .- J. Chen & G. Seelig, "Nucleic Acid Strand Displacement with Synthetic mRNA Inputs in Living Mammalian Cells," ACS Synthetic Biology 7, 2737-2741 (2018).

G. Rodrigo, S. Prakash, S. Shen, E. Majer, J.-A. Daròs & A. Jaramillo, "Model-based design of RNA hybridization networks implemented in living cells," Nucleic Acids Research 45, 9797-9808 (2017).

G. Sachdeva, A. Garg, D. Godding, J. C. Way & P. A. Silver, "In vivo co-localization of enzymes on RNA scaffolds increases metabolic production in a geometrically dependent manner," Nucleic Acids Research 42, 9493-9503 (2014).

Gootenberg, J. S. et al. Multiplexed and portable nucleic acid detection platform with Cas13, Cas12a, and Csm6. Science 360, 439-444 (2018).

I. Severcan, C. Geary, A. Chworos, N. Voss, E. Jacovetty & L. Jaeger, "A polyhedron made of tRNAs," Nature Chemistry 2, 772-779 (2010).

J. Chappell, M. K. Takahashi & J. B. Lucks, "Creating small transcription activating RNAs," Nat Chem Biol 11, 214-220 (2015).

J. G. Zalatan, M. E. Lee, R. Almeida, L. A. Gilbert, E. H. Whitehead, M. La Russa, J. C. Tsai, J. S. Weissman, J. E. Dueber, L. S. Qi & W. A. Lim, "Engineering complex synthetic transcriptional programs with Crispr Rna scaffolds," Cell 160, 339-350 (2015).

J. Hemelaar, "The origin and diversity of the HIV-1 pandemic," Trends Mol Med 18, 182-192 (2012).

J. K. Jung, K. K. Alam, M. S. Verosloff, D. A. Capdevila, M. Desmau, P. R. Clauer, J. W. Lee, P. Q. Nguyen, P. A. Pasten, S. J. Matiasek, J. F. Gaillard, D. P. Giedroc, J. J. Collins & J. B. Lucks, "Cell-free biosensors for rapid detection of water contaminants," Nat Biotechnol 38, 1451-1459 (2020).

J. Kim, P. Yin & A. A. Green, "Ribocomputing: Cellular Logic Computation Using RNA Devices," Biochemistry 57, 883-885 (2018).

J. Kim, Y. Zhou, P. D. Carlson, M. Teichmann, S. Chaudhary, F. C. Simmel, P. A. Silver, J. J. Collins, J. B. Lucks, P. Yin & A. A. Green, "De novo-designed translation-repressing riboregulators for multi-input cellular logic," Nat Chem Biol 15, 1173-1182 (2019).

J. Li, A. A. Green, H. Yan & C. Fan, "Engineering nucleic acid structures for programmable molecular circuitry and intracellular biocomputation," Nat Chem 9, 1056-1067 (2017).

J. N. Zadeh, C. D. Steenberg, J. S. Bois, B. R. Wolfe, M. B. Pierce, A. R. Khan, R. M. Dirks & N. A. Pierce, "NUPACK: Analysis and design of nucleic acid systems," J Comput Chem 32, 170-173 (2011).

K. A. Afonin, M. Kireeva, W. W. Grabow, M. Kashlev, L. Jaeger & B. A. Shapiro, "Cotranscriptional Assembly of Chemically Modified RNA Nanoparticles Functionalized with siRNAs," Nano Letters 12, 5192-5195 (2012).

K. A. Curtis, D. L. Rudolph & S. M. Owen, "Rapid detection of HIV-1 by reversetranscription, loop-mediated isothermal amplification (RT-LAMP)," J Virol Methods 151, 264-270 (2008).

K. H. Siu & W. Chen, "Riboregulated toehold-gated gRNA for programmable CRISPR Cas9 function," Nat Chem Biol 15, 217-220 (2019).

K. Pardee, A. A. Green, M. K. Takahashi, D. Braff, G. Lambert, J. W. Lee, T. Ferrante, D. Ma, N. Donghia, M. Fan, N. M. Daringer, I. Bosch, D. M. Dudley, D. H. O'Connor, L. Gehrke & J. J. Collins, "Rapid, Low-Cost Detection of Zika Virus Using Programmable Biomolecular Components," Cell 165, 1255-1266 (2016).

K. Pardee, A. A. Green, T. Ferrante, D. E. Cameron, A. DaleyKeyser, P. Yin & J. J. Collins, "Paper-based synthetic gene networks," Cell 159, 940-954 (2014).

L. M. Hochrein, M. Schwarzkopf, M. Shahgholi, P. Yin & N. A. Pierce, "Conditional Dicer substrate formation via shape and sequence transduction with small conditional RNAs," J Am Chem Soc 135, 17322-17330 (2013).

L. Oesinghaus & F. C. Simmel, "Switching the activity of Cas 12a using guide RNA strand displacement circuits," Nat Commun 10, 2092 (2019).

L. Zou, F. Ruan, M. Huang, L. Liang, H. Huang, Z. Hong, J. Yu, M. Kang, Y. Song, J. Xia, Q. Guo, T. Song, J. He, H. L. Yen, M. Peiris & J. Wu, "SARS-CoV-2 Viral Load in Upper Respiratory Specimens of Infected Patients," N Engl J Med 382, 1177-1179 (2020).

M. C. Tsai, O. Manor, Y. Wan, N. Mosammaparast, J. K. Wang, F. Lan, Y. Shi, E. Segal & H. Y. Chang, "Long noncoding RNA as modular scaffold of histone modification complexes," Science 329, 689-693 (2010).

M. H. Hanewich-Hollatz, Z. Chen, L. M. Hochrein, J. Huang & N. A. Pierce, "Conditional Guide RNAs: Programmable Conditional Regulation of CRISPR/Cas Function in Bacterial and Mammalian Cells via Dynamic RNA Nanotechnology," ACS Cent Sci 5, 1241-1249 (2019).

M. Li, M. Zheng, S. Wu, C. Tian, D. Liu, Y. Weizmann, W. Jiang, G. Wang & C. Mao, "In vivo production of RNA nanostructures via programmed folding of single-stranded RNAs," Nature Communications 9, 2196 (2018).

M. M. Arons et al., "Presymptomatic SARS-CoV-2 Infections and Transmission in a Skilled Nursing Facility," N Engl J Med 382, 2081-2090 (2020).

Ma et al., "Multi-arm RNA junctions encoding molecular logic unconstrained by input sequence for versatile cell-free diagnostics," Nature biomedical engineering, vol. 6, pp. 298-309, Mar. 2022.

Myhrvold, C. et al. Field-deployable viral diagnostics using CRISPR-Cas13. Science 360, 444-448 (2018).

O. H. Tam, A. A. Aravin, P. Stein, A. Girard, E. P. Murchison, S. Cheloufi, E. Hodges, M. Anger, R. Sachidanandam, R. M. Schultz & G. J. Hannon, "Pseudogene-derived small interfering RNAs regulate gene expression in mouse oocytes," Nature 453, 534-538 (2008).

Patchsung, M. et al. Clinical validation of a Cas13-based assay for the detection of SARSCoV- 2 RNA. Nat. Biomed. Eng. 4, 1140-1149 (2020).

R. Galizi, J. N. Duncan, W. Rostain, C. M. Quinn, M. Storch, M. Kushwaha & A. Jaramillo, "Engineered RNA-Interacting CRISPR Guide RNAs for Genetic Sensing and Diagnostics," CRISPR J 3, 398-408 (2020).

S. Bhadra & A. D. Ellington, "A Spinach molecular beacon triggered by strand displacement," RNA 20, 1183-1194 (2014).

S. P. Collins, W. Rostain, C. Liao & C. L. Beisel, "Sequence-independent RNA sensing and DNA targeting by a split domain CRISPR-Cas12a gRNA switch," Nucleic Acids Res (2021).

T. Gräf & A. R. Pinto, "The increasing prevalence of HIV-1 subtype C in Southern Brazil and its dispersion through the continent," Virology 435, 170-178 (2013).

T. Gräf, H. Machado Fritsch, R. M. de Medeiros, D. Maletich Junqueira, S. Esteves de Matos Almeida & A. R. Pinto, "Comprehensive Characterization of HIV-1 Molecular Epidemiology and Demographic History in the Brazilian Region Most Heavily Affected by AIDS," Journal of Virology 90, 8160-8168 (2016).

W. Wang, Y. Xu, R. Gao, R. Lu, K. Han, G. Wu & W. Tan, "Detection of SARS-CoV-2 in Different Types of Clinical Specimens," JAMA 323, 1843-1844 (2020).

X. Lu, L. Wang, S. K. Sakthivel, B. Whitaker, J. Murray, S. Kamili, B. Lynch, L. Malapati, S. A. Burke, J. Harcourt, A. Tamin, N. J. Thornburg, J. M. Villanueva & S. Lindstrom, "US CDC Real-Time Reverse Transcription PCR Panel for Detection of Severe Acute Respiratory Syndrome Coronavirus 2," Emerg Infect Dis 26 (2020).

Y. Nakashima, H. Abe, N. Abe, K. Aikawa & Y. Ito, "Branched RNA nanostructures for RNA interference," Chemical Communications 47, 8367-8369 (2011).

Y. Weizmann & E. S. Andersen, "RNA nanotechnology—The knots and folds of RNA nanoparticle engineering," MRS Bulletin 42, 930-935 (2017).

(56) References Cited

OTHER PUBLICATIONS

Z. D. Tong, A. Tang, K. F. Li, P. Li, H. L. Wang, J. P. Yi, Y. L. Zhang & J. B. Yan, "Potential Presymptomatic Transmission of SARS-CoV-2, Zhejiang Province, China, 2020," Emerg Infect Dis 26, 1052-1054 (2020).

* cited by examiner

*Hemagglutinin (HA) sequences*

H1N1   5'—..UCAUGCGAACAAUUCAACAGAGACACUGU..—3'    (SEQ ID NO:216)

H1N2   5'—..CCAUGCCAACAACUCAACCGACACUGU..—3'    (SEQ ID NO:217)

*Neuraminidase (NA) sequences*

H1N1   5'—..CGAAGAGAACACAAUCUGGACUAGCGGGGAGC..—3'    (SEQ ID NO:218)

H5N1   5'—..CAAAGAGAGCACAAUUUGGACUAGUGGGGAGC..—3'    (SEQ ID NO:219)

d

H1N1 identification: H1 AND N1 e

*Hemagglutinin (HA) sequences*

H1N2  5′ – ..ACAUUUACAGCUGCAUAUGCCGGACACAAU.. –3′      (SEQ ID NO:220)

H1N1  5′ – ..ACAUUUACAACCGCAAAUGCAGACACAUU.. –3′      (SEQ ID NO:221)

*Neuraminidase (NA) sequences*

H1N2  5′ – ..ACUUCAGGUACAUAUGGAACAGGCUCAUGGC.. –3′      (SEQ ID NO:222)

H3N2  5′ – ..ACCUCAGGUACAUAUGGAACAGGCUCAUGGC.. –3′      (SEQ ID NO:223)

f

H1N2 identification: H1 AND N2 a   Toehold switch AND logic:
Inputs are not sequence independent b   Toehold switch OR logic:
Gate RNA adds N-terminal peptides and requires translation through hairpin structures Fig. 14 (continued)

Fig. 14 (continued)

DETECTION OF SARS-CoV-2 USING RNA MULTI-ARM JUNCTION LOGIC GATES

CROSS-REFERENCE TO RELATED APPLICATIONS

This application claims priority to U.S. Provisional Application No. 63/237,012 filed on Aug. 25, 2021, the contents of which are incorporated by reference in their entireties.

STATEMENT REGARDING FEDERALLY SPONSORED RESEARCH

This invention was made with government support under grant numbers GM126892, U01 AI148319, R01 EB031893, R21 AI136571 awarded by the National Institutes of Health and 2029532 awarded by the National Science Foundation. The government has certain rights in this invention.

SEQUENCE LISTING

A Sequence Listing accompanies this application and is submitted as an XML file of the sequence listing named "112624.01349.xml" which is 219,254 bytes in size and was created on Jul. 25, 2022. The sequence listing is electronically submitted via Patent Center with the application and is incorporated herein by reference in its entirety.

BACKGROUND

RNA adopts diverse secondary and tertiary structures that enable it to perform a variety of different roles in the cell, from regulating gene expression and catalyzing chemical reactions to sensing small molecules and scaffolding proteins. RNA molecules designed to fold into diverse secondary structures have been used to tightly regulate gene expression at the transcriptional and translational levels in response to trans-acting RNAs, small molecules, proteins, or specified logic expressions, and have been used in strand-displacement systems for computing and imaging applications. Moreover, they have found use in low-cost systems for detection of viruses, mutations, and for water testing. At the same time, the structural diversity of RNA has been harnessed in RNA nanotechnology to generate a variety of RNA-based nanostructures with complex geometries through self-assembly. These structures are assembled from molecular building blocks featuring hairpins, multi-arm junctions, and other structural elements programmed to fold into prescribed structures through combinations of dangling end, kissing loop, and crossover interactions. Such assemblies have enabled the production of multivalent nanoparticles carrying siRNA payloads and have also been synthesized within living cells enabling enzyme localization. They provide a wealth of different RNA nanostructures that can be harnessed for programming cellular function.

Taking concepts from RNA nanotechnology and RNA-based regulation of gene expression, researchers have developed self-assembly-driven molecular computing systems that operate in living cells and exploit the combined interactions of multiple carefully designed synthetic RNAs. Such ribocomputing devices act by modulating gene expression in response to specified combinations of input RNAs and take advantage of the predictability of RNA-RNA interactions to enable effective computer-based design. These systems have been used to carry out combinations of AND, OR, NAND, and NOR logic with up to a dozen inputs and have operated using complexes formed from as many as five distinct RNAs in living cells. However, the ribocomputing devices developed thus far have had several significant limitations that constrain the range of input RNAs that they can monitor and the range of output proteins that they can produce. These systems have relied on hybridization between multiple input RNAs for implementing AND logic, limiting their use against natural transcripts that lack the necessary complementarity between sequences or requiring adapter strands that reduce system output (FIG. 12a). Moreover, encoding OR logic elements within RNA regions that are translated has often required long open reading frames with high secondary structure placed immediately upstream of the output gene sequence (FIG. 12b). These regions can impede ribosome processivity, thus decreasing translation efficiency, and lead to extended N-terminal peptide extensions with unpredictable effects on output protein folding (FIG. 12b,c). Addressing these limitations requires alternative means of initiating RNA-RNA interactions to reduce sequence constraints and improved strategies for encoding molecular logic that minimize their impact on output gene sequence.

SUMMARY

In a first aspect, the present invention provides loop-mediated riboregulators for the detection of SARS-CoV-2. The riboregulators comprise a multi-arm junction upstream of the coding sequence of a reporter gene. The multi-arm junctions comprise from 5' to 3': a first base stem region, at least two sensor arms, and a second base stem region. Importantly, the first base stem region is at least partially complementary to the second base stem region, such that the first and second base stem regions pair to form a base stem. Each sensor arm comprises from 5' to 3': a first sensor stem region, a loop region, and a second sensor stem region. Importantly, the first sensor stem region is at least partially complementary to the second sensor stem region such that the first and second sensor stem regions pair to form a sensor stem, and a portion of the loop region is at least partially complementary to a target RNA sequence from SARS-CoV-2. The multi-arm junctions comprise a ribosome binding site (RBS) and start codon within one of the base stem regions or sensor stem regions, such that the secondary structure of the multi-arm junction conceals the RBS and start codon in the absence of target RNA sequences. Binding of one or more target RNA sequences to one or more loop regions unwinds at least a portion of the secondary structure to expose the RBS and start codon thereby enabling translation of the reporter gene.

In a second aspect, the present invention provides DNA constructs comprising a promoter and a sequence encoding a loop-mediated riboregulator described herein.

In a third aspect, the present invention provides methods for detecting the presence of two or more target RNA sequences from SARS-CoV-2 in a sample. The methods comprise: (a) providing a sample comprising RNA; (b) contacting the sample with a loop-mediated riboregulator described herein; and (c) detecting translation of the reporter gene. In these methods, translation of the reporter gene indicates that SARS-CoV-2 is present in the sample.

DETAILED DESCRIPTION

The present invention provides loop-mediated riboregulators for the detection of SARS-CoV-2, as well as DNA constructs encoding the loop-mediated riboregulators and methods of using the loop-mediated riboregulators to detect the presence of severe acute respiratory syndrome coronavirus 2 (SARS-CoV-2) in a sample.

In previous work, the inventors developed a new strategy for implementing molecular logic that exploits multi-arm junction RNA nanostructures to regulate gene expression while eliminating input RNA sequence constraints and reducing sequence interference with the output gene. These ribocomputing systems make use of loop-initiated RNA activator (LTRA) motifs (also referred to herein as "sensor arms") that bind to input RNAs through extended loop domains and expose downstream functional domains for subsequent reactions. See U.S. Patent Application Publication US20190218624, which is hereby incorporated by reference in its entirety.

Figure 1:
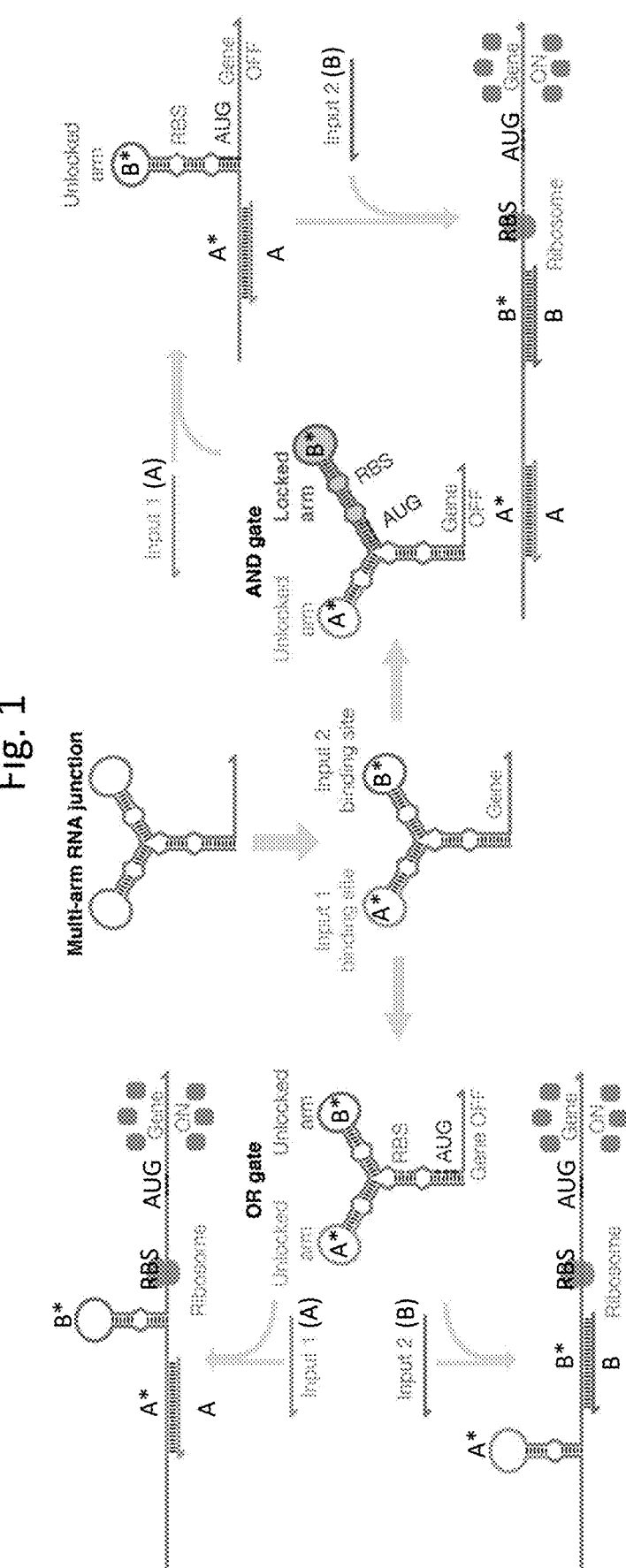
FIG. 1 shows design strategies for implementing sequence-independent RNA-based logic using multi-arm junctions. The three-arm junction in the schematic provides two sensing arms (A* and B*) for binding to complementary input RNAs (A and B) and is positioned upstream of the regulated gene. Logic operations are encoded within the multi-arm junction nanostructure by controlling the length and number of the stem-loop arms. Unlocked stem-loop arms enable direct binding of input RNAs and are used for OR logic. Locked arms are not available for binding to an input RNA until they are unlocked through binding of another input RNA species and are used for AND logic.

In the present application, the inventors show that LIRAs can be used as riboregulators that activate gene expression with high dynamic range and orthogonality in *Escherichia coli* without imposing any sequence constraints on the input RNAs and the output gene. Using these validated motifs, the inventors generate logic gate RNAs that encode multi-input molecular logic by folding up single strands of RNA into multi-arm junctions actuated by independent LIRA modules (FIG. 1). The resulting gate RNA nanostructures unfold in a prescribed manner as they interact with cognate input RNAs to activate gene expression when AND or OR logic expressions are satisfied. The inventors use the multi-arm junctions to implement three-input AND and OR operations in *E. coli* using completely sequence-independent input RNAs. Porting these systems to paper-based cell-free transcription-translation reactions, they show that LIRAs can be designed to detect viral RNA sequences and, when coupled with isothermal amplification reactions, to detect the dengue virus, norovirus, and yellow fever virus. Finally, they harness the capacity of multi-arm RNA junctions to detect sequence-independent inputs to use OR logic to tolerate sequence differences between HIV subtypes and AND logic to accurately identify SARS-CoV-2 in clinical saliva samples by targeting at two regions of the virus at the same time.

Compositions:

In a first aspect, the present invention provides loop-mediated riboregulators comprising a multi-arm junction upstream of the coding sequence of a reporter gene. The multi-arm junctions comprise from 5' to 3': a first base stem region, at least two sensor arms, and a second base stem region. Importantly, the first base stem region is at least partially complementary to the second base stem region, such that the first and second base stem regions pair to form a base stem. Each sensor arm comprises from 5' to 3': a first sensor stem region, a loop region, and a second sensor stem region. Importantly, the first sensor stem region is at least partially complementary to the second sensor stem region such that the first and second sensor stem regions pair to form a sensor stem, and a portion of the loop region is at least partially complementary to a target RNA sequence from SARS-CoV-2. The multi-arm junctions comprise a ribosome binding site (RBS) and start codon within one of the base stem regions or sensor stem regions, such that the secondary structure of the multi-arm junction conceals the RBS and start codon in the absence of target RNA sequences. Binding of one or more target RNA sequences to one or more loop regions unwinds at least a portion of the secondary structure to expose the RBS and start codon thereby enabling translation of the reporter gene.

As used herein, the term "riboregulator" refers to a ribonucleic acid (RNA) that generates a response upon binding to one or more target RNA sequences via Watson-Crick base pairing. The riboregulators of the present invention respond by activating translation of a reporter gene. Because activation is driven by base pairing, the riboregulators can be tailored to differentiate and respond to specific genetic sequences or to combinations of specific genetic sequences. The term "loop-mediated" refers to the fact that translation is activated upon binding of a target RNA sequence to a sequence within the loop of a sensor arm. Specifically, binding to the loop, exposes an RBS and start codon, thereby permitting translation of the reporter gene.

The loop-mediated riboregulators of the present invention comprise a multi-arm junction at the 5' end of an RNA followed by the coding sequence of a reporter gene. The "multi-arm junction" comprises multiple RNA stem-loops. As is illustrated in FIG. 1, the multi-arm junction comprises a "base stem" topped by at least two sensor arms. This configuration is achieved by flanking the sequences that form the sensor arms with "base stem regions," i.e., sequences that are at least partially complementary such that they pair to form a base stem.

The ideal length of the base stem depends on the logic of the riboregulator. For use in an OR gate riboregulator, the ideal length of the base stem is 20 bases since it needs to accommodate the RBS and AUG start codon. For use in an AND gate riboregulator, the base stem may be 9-12 bases in length. The stem of the sensor arms may be about 30 bases to about 39 bases in length, preferably about 36 bases in length. However, the stem length of the sensor arms may be truncated or elongated to accommodate a hairpin reconfiguration domain. The length of a stem-forming region may be measured from the first pair of complementary nucleotides to the last pair of complementary bases and includes mismatched nucleotides (e.g., pairs other than AT, AU, GC), nucleotides that form a bulge, or nucleotides that form an inner loop.

As used herein, a "sensor arm" (also referred to herein as a loop-initiated RNA activator (LIRA) motif) is a stem loop has the ability to bind to a target RNA sequence. Each sensor arm comprises a first sensor stem region and a second sensor stem region that are at least partially complementary, such that they pair to form a "sensor stem" in the absence of target RNA sequences. The sensor stem regions flank a non-complementary loop region that contains a binding site for a target RNA sequence.

As used herein, the term "complementary" refers to the ability of a nucleic acid molecule to bind to (i.e., hybridize with) another nucleic acid molecule through the formation of hydrogen bonds between specific nucleotides (i.e., A with T or U and G with C), forming a double-stranded molecule. As used herein, the term "at least partially complementary" describes a pair of nucleic acid molecules that are at least 80%, at least 85%, at least 90%, at least 95%, at least 97%, at least 98%, or at least 99% complementary to each other including G-U wobble base pairs.

As used herein, a "ribosome binding site (RBS)" is a sequence within an RNA molecule at which the 30S and 50S subunits of the ribosome assemble to initiate translation of an encoded protein. The RBS is positioned upstream of the "start codon", i.e., the first codon within an RNA that is translated by a ribosome. In the absence of target RNA sequences, the multi-arm junctions form strong secondary structures (i.e., base pairing interactions within the RNA molecule) that conceal the RBS and start codon. As a result, translation is repressed until target RNA sequences bind to the loop regions of sensor arms and unwind the structure. In some embodiments, the RBS and start codon are concealed within one of the base stem regions (i.e., the first base stem region or the second base stem region). In other embodiments, the RBS and start codon are concealed within one of the sensor stem regions (i.e., a first sensor stem region or a second sensor stem region).

Figure 3:
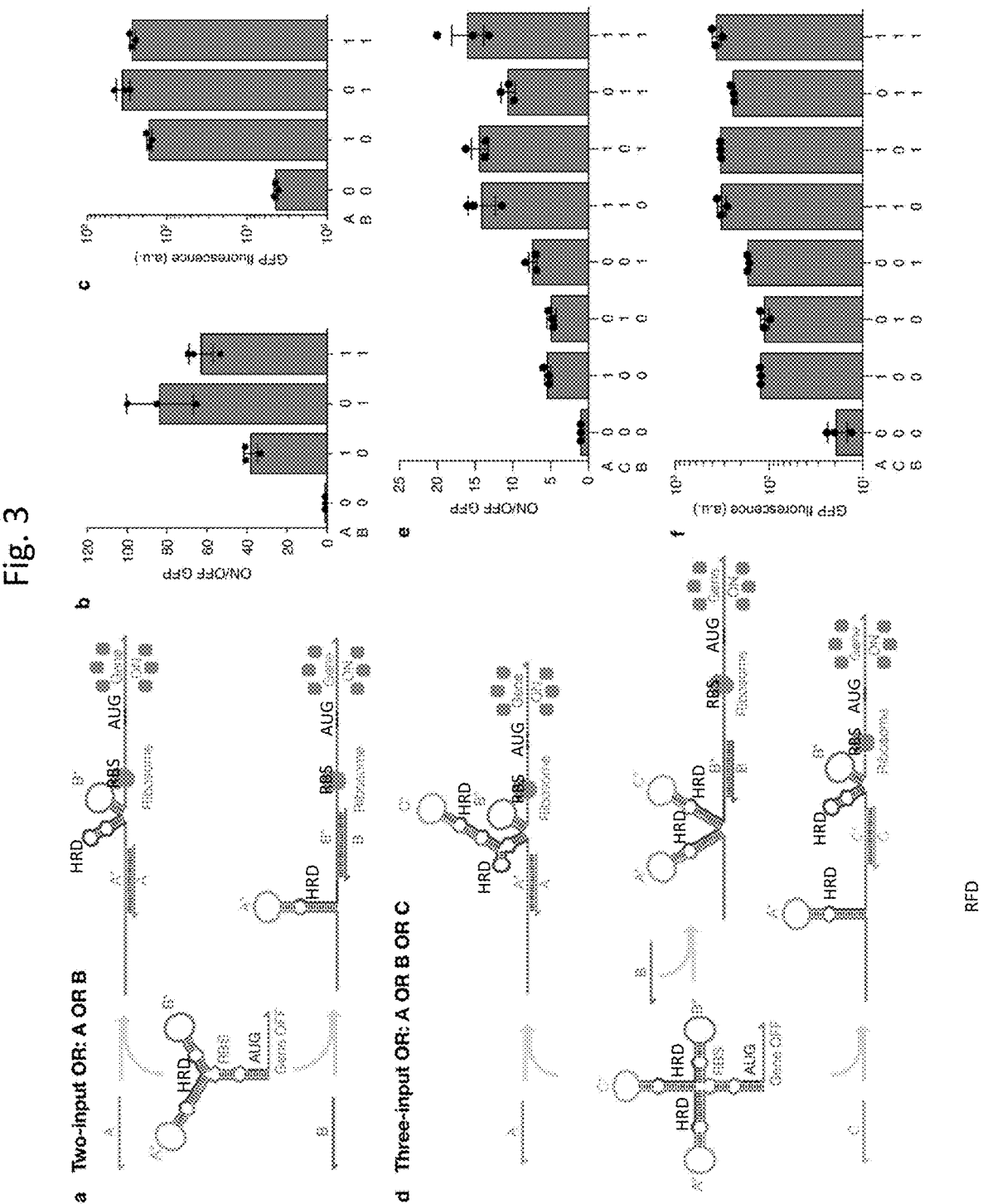
FIG. 3 depicts multi-arm RNA junction molecular OR logic in *E. coli* using hairpin reconfiguration domains (HRD). a, Schematic of a two-input OR logic design and its interaction mechanism with the input RNAs. b, ON/OFF fluorescence ratios of each input combination. c, GFP fluorescence of each input combination. d, Schematic of a three-input OR logic design and its interaction mechanism with the input RNAs. e, ON/OFF ratios of each input combination. f, GFP fluorescence of each input combination. All p values from two-tailed student's t-tests between each TRUE state and FALSE state are less than 0.05. Measurements were taken 4 hours after induction with IPTG, n=3, bars represent the geometric mean±SD.

In some embodiments, the multi-arm junction further comprises one or more hairpin reconfiguration domains positioned between the two sensor arms. The hairpin reconfiguration domains serve to decrease the thermodynamic barrier to riboregulator activation and increase translational output. As is illustrated in FIG. 3a, a "hairpin reconfiguration domain (RFD)" is an RNA sequence that generates an additional stem-loop upon the binding of a first target RNA sequence to a first sensor arm (A). The stem of the new stem-loop disrupts the bottom portion of the second sensor arm (B), providing a single-stranded region upstream of the RBS and more space to accommodate the ribosomal footprint. During transcription, the hairpin reconfiguration domain can also help to delay formation of strong sensor arm stem-loop structures to discourage transcriptional termination. In one embodiment, the hairpin reconfiguration domain may contain 28 bases in total. For the hairpin reconfiguration domain to work, its loop should be at least 4 bases in length, and it should be positioned such that it spans the two sensor arms with 20 bases incorporated into the base stem of the 5' arm and 8 bases incorporated into the base stem of the 3' arm (see FIG. 3a). In the Examples, the inventors incorporated a hairpin reconfiguration domain comprising a base stem that is 12 bases in length and the loop that is 4 bases in length into their multi-arm junctions. However, the dimensions of the hairpin reconfiguration domain used with the present invention can be modified to achieve the desired thermodynamics and translational output.

The loop-mediated riboregulators of the present invention respond to the presence of multiple SARS-CoV-2 sequences and comprise at least two sensor arms that each bind to different target RNA sequences. In the Examples, the inventors demonstrate that loop-mediated riboregulators can be used to implement three-input AND and OR operations in *E.*

*coli.* Thus, in some embodiments, the multi-arm junction comprises at least three sensor arms. In some embodiments, the loop-mediated riboregulators encode complex, multi-input logic circuits comprising more than three sensor arms. For example, the loop-mediated riboregulators may comprise 2, 3, 4, 5, or more sensor arms.

Figure 7:
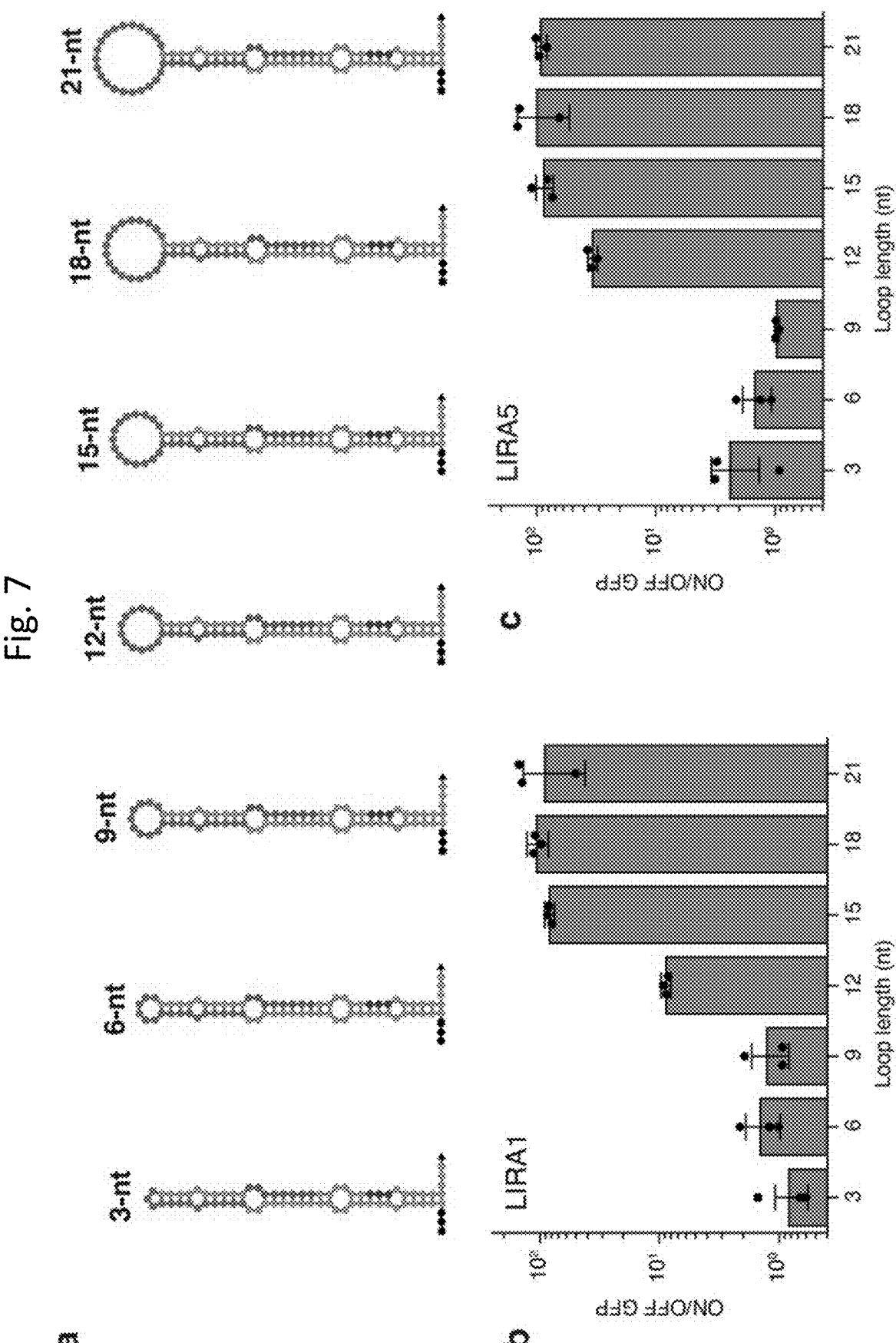
FIG. 7 shows testing of LIRAs with different loop lengths. a, Schematic of LIRAs with different loop lengths. b, ON/OFF GFP fluorescence ratios of LIRA1 loop variants tested in *E. coli* with and without expression of the cognate input RNA. c, ON/OFF fluorescence ratios of LIRA5 loop variants. For both sets of systems, device ON/OFF ratios saturate as loop size increases beyond 15 nt.

The inventors have determined that effective riboregulator-target RNA interactions require that the loop domains of the sensor arms are sufficiently long (i.e., ≥15 nucleotides) such that they provide sufficient binding free energy. Thus, in some embodiments, the loop region of the at least two sensor arms is at least 15 nucleotides in length. In the Examples, the inventors tested senor arms with loop regions of various lengths and determined that loop regions that are 21 nucleotides in length (i.e., the longest length tested) perform best (see FIG. 7). Thus, in some embodiments, the loop region of the at least two sensor arms is at least 21 nucleotides in length.

In some embodiments, the stems of the sensor arms (i.e., the sensor stems) comprise one or more bulges. As used herein, the term "bulge" refers to a region within a hybridized double-stranded RNA in which the bases are unpaired (i.e., not complementary). In the Examples, the inventors determine that including four bulges in the sensor stem (each separated by several bases) reduces the likelihood of premature rho-independent transcriptional termination and increases the thermodynamics driving the riboregulator-target RNA interaction. Thus, in some embodiments, the sensor stem comprises four bulges. In some embodiments, the length of the bulge(s) is about 1-2 bases on each side of the stem.

In some embodiments, the loop-mediated riboregulators are designed to activate gene expression when AND logic length (excluding any hairpin reconfiguration domain). Additionally, AND riboregulators are distinguished from OR riboregulators by the positioning of the RBS and stop codon within the RNA structure. In an AND riboregulator, the RBS and stop codon are positioned within the stem of the sensor arm with the locked configuration to prevent premature activation. In contrast, in an OR riboregulator, the RBS and stop codon are positioned within the base stem, ensuring that the binding of even a single target RNA will make them accessible to the translational machinery.

The loop-mediated riboregulators of the present invention are designed to detect target RNA sequences from severe acute respiratory syndrome coronavirus 2 (SARS-CoV-2), i.e., RNA sequences found within the SARS-CoV-2 genome. SARS-CoV-2 is a positive-sense single-stranded RNA virus that causes COVID-19, the respiratory illness responsible for the COVID-19 pandemic. Two regions within the SARS-CoV-2 nucleocapsid (N) gene, i.e., 2019-nCoV_N1 and 2019-nCoV_N2, are commonly used for the detection of SARS-CoV-2 due to their excellent specificity and sensitivity. In the Examples, the inventors tested two loop-mediated riboregulators, referred to as N1*N2* and N2*N1, that detect the presence of both of these N gene regions simultaneously (i.e., using AND logic). Thus, in some embodiments, the loop-mediated riboregulators are designed to detect two or more target RNA sequences from the SARS-CoV-2 N gene. In some embodiments, the sensor stems comprise at least one the sensor stem sequences that the inventors used to generate N1*N2* and N2*N1 (i.e., SEQ ID NOs:3-6). See Table 1, below. In some embodiments, the multi-arm junction comprises an RNA sequence selected from N1*N2* (i.e., SEQ ID NO:1) or N2*N1 (i.e., SEQ ID NO:2). See Table 10.

TABLE 1

| Sequences of sensor stems used in the riboregulators tested herein | | |
|---|---|---|
| Riboregulator | Sequence of left sensor stem | Sequence of right sensor stem |
| N1*N2* | TCGCTACAGCGACATCTACAC ATTACGTTTGGTGGACCCTCA GATTCAACTAAACCTAATGGG TAGAACTCGCTAAAGCGA (SEQ ID NO: 3) | TGTCTACCTGCCATATCTTATC TCCTGAACTGATTACAAACAT TGGCCGCAAATTGTGTATTCA GTAGAGGAGATACAATATGGC AATTAGACA (SEQ ID NO: 4) |
| N2*N1* | TCGCTACAGCGACATCTACAG GAACTGATTACAAACATTGGC CGCAAATTGAATCTGTTCCGG TAGAACTCGCTAAAGCGA (SEQ ID NO: 5) | TGTCTACCTGCCATATCTTATC TCCTGAACTGATTACAAACAT TGGCCGCAAATTGTGTATTCA GTAGAGGAGATACAATATGGC AATTAGACA (SEQ ID NO: 6) | expressions are satisfied, i.e., when all of their sensor stems are bound to cognate target RNA sequences. In other embodiments, the loop-mediated riboregulators are designed to activate gene expression when OR logic expressions are satisfied, i.e., when at least one of their sensor stems is bound to its cognate target RNA sequence. In "AND riboregulators", one sensor arm has a locked configuration and the other sensor arms have an unlocked configuration, whereas in "OR riboregulators," all of the sensor arms have an unlocked configuration. Sensor arms with an "unlocked configuration" are shorter and are always available for target RNA binding. In contrast, sensor arms with a "locked configuration" are longer and are not available for binding to a target RNA until they are unlocked through the binding of target RNA sequences to the other sensor arm(s). An unlocked sensor arm need only be 10 bases in length, whereas a locked sensor arm should be at least 30 bases in The loop-mediated riboregulators of the present invention comprise a coding sequence of a reporter gene. A "reporter gene" is a gene encoding a product that creates a detectable phenotype or signal. In some embodiments, the reporter gene is a resistance gene, i.e., a gene that encodes a protein that allows a cell or organism to grow in conditions in which it could not grow in the absence of that protein. For example, in some embodiments, the reporter gene is aadA, ampR, or cat, which confer resistance to spectinomycin, ampicillin, and chloramphenicol, respectively. In other embodiments, the resistance gene encodes a molecule that produces a detectable signal. Suitable detectable signals include, without limitation, fluorescent signals, luminescent signals, colorimetric signals, wavelength absorbance, and radioactive signals. For example, in some embodiments, the reporter gene encodes a fluorescent protein, such as mCherry or GFP. In other embodiments, the reporter gene encodes a portion of a split fluorescent protein, such as GFP11 or sfCherry2. Other reporter genes that can be used with the present invention include, without limitation, those than encode enzymes that act on reporter substrates (e.g., β-galactosidase, β-glucoronidase, alkaline phosphatase, DHFR, CAT, trehalase, glucose oxidase, EcoRI, BamHI, HindIII, CRISPR/Cas9, CRISPR/Cas12a, CRISPR/Cas13a, T3 RNA polymerase, SP6 RNA polymerase, luciferase, nanoluciferase) and truncated forms of these proteins that undergo spontaneous complementation (e.g., lacZ-alpha subunit).

In a second aspect, the present invention provides DNA constructs comprising a promoter and a sequence encoding a loop-mediated riboregulator described herein. The term "DNA construct" refers a to recombinant polynucleotide, i.e., a polynucleotide that was formed by combining at least two polynucleotide components from different sources, natural or synthetic. For example, a construct may comprise the coding region of one gene operably linked to a promoter that is (1) associated with another gene found within the same genome, (2) from the genome of a different species, or (3) synthetic. Constructs can be generated using conventional recombinant DNA methods.

The term "promoter" refers to a DNA sequence capable of controlling the transcription of an operably linked coding sequence (i.e., a DNA sequence encoding a protein or functional RNA). In general, a coding sequence is located 3' to a promoter sequence. Promoters may be derived in their entirety from a native gene or may be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. In some embodiments, the promoter used in the DNA construct is an "inducible promoter," i.e., a promoter that is regulated and is active only is response to specific stimuli.

Methods:

In a third aspect, the present invention provides methods for detecting the presence of two or more target RNA sequences from SARS-CoV-2 in a sample. The methods comprise: (a) providing a sample comprising RNA; (b) contacting the sample a loop-mediated riboregulator described herein; and (c) detecting translation of the reporter gene. In these methods, translation of the reporter gene indicates that SARS-CoV-2 is present in the sample.

Any sample comprising RNA can be subjected to the methods of the present invention. Suitable samples include patient samples (e.g., blood, serum, urine, saliva, tissues, cells, feces, nasopharyngeal swabs, organs), environmental samples (e.g., water, soil, surface swabs), and agricultural samples (e.g., leaves, roots, feces, urine).

In the present methods, the presence of SARS-CoV-2 is indicated by detection of the translation of the reporter gene. As is discussed above, the reporter gene may create a detectable phenotype or signal. Thus, depending on the reporter gene used, detection may involve assessing the phenotype of a cell or organism comprising the loop-mediated riboregulator or detecting a detectable signal. Alternatively, reporter gene expression may also be detected at the transcript or protein level (e.g., via RT-qPCR or western blotting, respectively).

In some embodiments, the methods further comprise incubating the sample under conditions that allow for translation of the reporter gene in the presence of at least one of the two or more target RNA sequences but not in the absence of the two or more target RNA sequences. Suitably, this incubation is performed at a temperature between 20° C. and 42° C. for at least 5, at least 10, at least 15, at least 20, at least 25, or at least 30 minutes. Preferably, the incubation is performed for at least 15 minutes. When a paper-based system is used in the assay (as described below), the humidity of the reaction must be maintained to prevent the reaction from drying out.

In some cases, it may be advantageous to adapt the methods described herein for high-throughput, reproducible, and rapid detection, for example in a clinical setting. The inventors have demonstrated that their loop-mediated riboregulators can be used for detection in colorimetric paper-based cell-free transcription-translation reactions. Thus, in some embodiments, the methods are carried out in a paper-based cell-free system, and, in some embodiments, translation of the reporter gene produces a colorimetric readout. The term "paper-based cell-free system" refers to an in vitro transcription-translation system that is freeze-dried onto paper disks for stable, long-term storage at room temperature. For a detailed description of such systems, see Pardee et al. (*Cell* 2014, 159(4):940-54), which is hereby incorporated by reference in its entirety, for a description of one such system.

The term "colorimetric readout" describes output that involves the production of a colored reagent. For example, in Pardee et al. (*Cell* 2014, 159(4):940-54), a yellow to purple color change serves as a colorimetric readout (see FIG. 3A). This color change is produced by β-galactosidase (LacZ), which cleaves a yellow substrate (i.e., chlorophenol red-β-D-galactopyranoside) embedded in the freeze-dried paper discs to produce a purple chlorophenol red product that is visible to the naked eye and can be measured on standard plate readers by monitoring the absorbance at 570 nm. Other enzymes that can be used to generate a colorimetric readout via substrate cleavage include β-glucoronidase. Each of these enzymes can be used with a variety of substrates to produce different color changes. For example, β-galactosidase can be used with the substrates X-Gal, Red-β-D-Gal, Rose-β-D-Gal, Purple-β-D-Gal, and Green-β-D-Gal, whereas β-glucoronidase can be used with the substrates X-GlcU, Red-β-D-GlcU, and Rose-β-D-GlcU. Colorimetric readouts may be detected by eye or using a device (e.g., a colorimeter, a camera).

In some embodiments, the RNA in the sample is amplified prior to step (b). RNA can be amplified using any method that is commonly used in the art including, but not limited to, reverse transcription polymerase chain reaction (RT-PCR), reverse-transcription, loop-mediated isothermal amplification (RT-LAMP), reverse transcription helicase-dependent amplification (RT-HDA), and reverse transcription recombinase polymerase amplification (RT-RPA). In the Examples, the inventors used nucleic acid sequence-based amplification (NASBA) to amplify low-concentration pathogen RNAs prior to use in the paper-based assays. NASBA utilizes reverse transcriptase, T7 RNA polymerase, RNase H, and DNA primers that incorporate the T7 promoter sequence to generate multiple RNA copies from a starting RNA template. Thus, in some embodiments, the RNA in the sample is amplified using NASBA prior to step (b).

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

The central role of RNA in regulating gene expression and its predictable base pairing properties make it a powerful tool for implementing molecular circuits. However, applications of RNA-based molecular logic have been hampered by sequence constraints imposed on the input and output of the circuits. In the following example, the inventors describe the generation of single-stranded RNA nanostructures consisting of multi-arm junctions that robustly execute molecular logic with substantially reduced sequence constraints. In their RNA nanostructures, self-assembled multi-arm junctions are inserted upstream of a regulated gene. The multi-arm junctions are designed to sequentially unfold in response to different RNA inputs to conditionally activate translation. Specifically, the multi-arm junctions comprise loop-initiated RNA activators (LIRAs) that function independently of the sequence of the input RNAs and that reduce interference with the output gene. The inventors show that these RNA nanostructures can be used to execute two-input and three-input OR and AND logic in *Escherichia coli*. Further, they designed paper-based cell-free colorimetric assays that utilize the nanostructures to accurately identify two human immunodeficiency virus (HIV) subtypes (by executing OR logic) in amplified synthetic HIV RNA as well as severe acute respiratory syndrome coronavirus-2 (via two-input AND logic) in amplified RNA from saliva samples. Thus, these RNA nanostructures are powerful tools for sequence-independent molecular sensing and logic with broad biotechnological and diagnostic applications.

Materials and Methods

LIRA Library Design

LIRAs were designed computationally using the NUPACK software package[41] and selected for experimental testing using procedures reported previously[7]. Briefly, a set of 337 candidate LIRA devices were generated by NUPACK and the top 60 of these riboregulators were selected on the basis of their ensemble defect levels. All candidate LIRAs shared the same secondary structures but differed in sequence outside of the conserved RBS, start codon, and reporter gene regions. Pairwise interactions between all the LIRAs and input RNAs were then computed to determine the expected equilibrium concentration of the LIRA-input complexes formed. Using non-cognate LIRA-input complex formation probability as a crosstalk metric, a Monte Carlo selection algorithm was used to generate a library of 24 LIRAs expected to display the lowest expected overall crosstalk.

Strains and Growth Conditions

The following *E. coli* strains were used in this study: BL21 Star DE3 (F⁻ ompT hsdS$_B$ (r$_B$⁻m$_B$⁻) gal dcm rne131 (DE3); Invitrogen), BL21 DE3 (F⁻ ompT hsdS$_B$ (r$_B$⁻m$_B$⁻) gal dcm (DE3); Invitrogen), MG1655Pro (F⁻ λ⁻ ilvG-rfb-50 rph-1 Sp$^R$ lacR tetR), and DH5$^α$ (endA1 recA1 gyrA96 thi-1 glnV44 relA1 hsdR17(r$_K$⁻m$_K$⁺) λ⁻; Invitrogen). All strains were grown in Luria broth (LB) medium at 37° C. with appropriate antibiotics.

Plasmid Construction

Plasmids were constructed using PCR and Gibson assembly. Single-stranded DNAs for expressing LIRAs, gate RNAs, and input RNAs were purchased from Integrated DNA Technologies and amplified into the double-stranded DNA form via PCR. The amplified DNAs were then connected with plasmid backbones by 30-bp homology domains using Gibson assembly. All Gibson assembly products were transformed in the *E. coli* DH5α strain and sent out for sequence validation via Sanger sequencing. Backbones used for constructing the plasmids were amplified from the commercial vectors pET15b, pCOLADuet, and pCDFDuet (ENVD Millipore) via PCR followed with DpnI treatment. The reporter protein for all plasmids is GFPmut3b with an ASV degradation tag unless otherwise noted. The primers used for plasmid construction are listed in Table 2.

lowing recipe: cell-free solution A, 40%; cell-free solution B, 30%; RNase Inhibitor (Roche, 03335402001, distributed

TABLE 2

| Universal primers for plasmid construction | | |
|---|---|---|
| Name | Sequence | Notes |
| Dnorm_T7_fwd | CTAGTAAATTCGCGTTTCTACGGTA GCCGGGCGCTAATACGACTCACTA TAGGG (SEQ ID NO: 7) | forward primer for inserts PCR |
| linker_21_rev_30N | CTTTTGCGCTGCCGCCAGGTT (SEQ ID NO: 8) | reverse primer for hairpin inserts PCR |
| T7_term_min_rev_30N | CCCGTTTAGAGGCCCCAAGGGGTT ATGCT (SEQ ID NO: 9) | reverse primer for trigger inserts PCR |
| linker_21_fwd_57C | AACCTGGCGGCAGCGCAA (SEQ ID NO: 10) | forward primer for hairpin backbone PCR |
| T7_term_min_fwd_57C | TAGCATAACCCCTTGGGGC (SEQ ID NO: 11) | forward primer for trigger backbone PCR |
| lacZ_min_fwd | AACCTGGCGGCAGCGCAAAAGATG CGTAAAATGACCATGATTACGGAT TCACTGG (SEQ ID NO: 12) | forward primer for hairpin backbone PCR with LacZalpha output |
| Dstar_pET15b_rev | CCGGCTACCGTAGAAACGCGAATT TACTAGCGAGATCTCGATCCTCTAC GC (SEQ ID NO: 13) | reverse primer for backbone PCR |
| Dstar_pCDF_pCOLA_rev | CCGGCTACCGTAGAAACGCGAATT TACTAGCATAAGGGAGAGCGTCGA GATC (SEQ ID NO: 14) | reverse primer for backbone PCR |
| pET15b_seq_fwd | CCTGCCACCATACCCACGC (SEQ ID NO: 15) | sequencing primer |
| pCOLA_seq_fwd | CGTTACTGGTTTCACATTCACCACC C (SEQ ID NO: 16) | sequencing primer |

Flow Cytometry Measurements and Analysis

Bacterial colonies transformed with combinations of LIRA or gate RNA and input RNA plasmids were inoculated in 1 ml of LB in triplicate with appropriate antibiotics and grown overnight at 37° C. with shaking. On the second day, 5 μl overnight-cultured medium was diluted by 100-fold in 495 μl of fresh LB with 30 μg/ml kanamycin, 50 μg/ml ampicillin, and 25 μg/ml spectinomycin. After 80 min of recovery, IPTG was added into each well to a final concentration of 0.1 mM. Flow cytometry measurements were performed after 3, 4, and 5 hours of induction.

Figure 11:
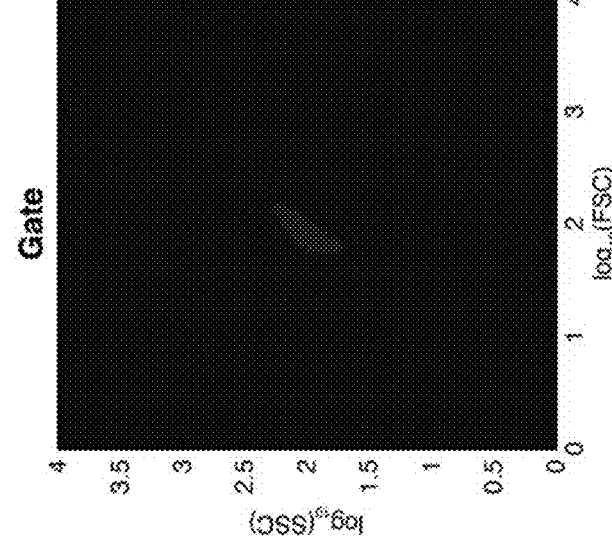
FIG. 11 shows representative flow cytometry gating data. Two-dimensional histograms of *E. coli* cells expressing LIRA11 and its cognate input RNA along the side scatter (SSC) and forward scatter (FSC) channels. A gate was defined based on the SSC and FSC histograms (middle histogram) to remove data caused by debris and doublets. Right histogram shows the overlay of the gate over the experimental data.
Figure 11:
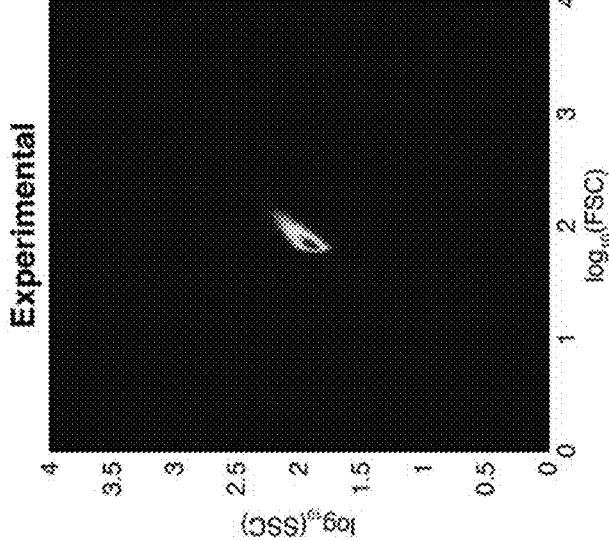

Flow cytometry was performed using a S1000 cell analyzer (Stratedigm) equipped with a high-throughput auto sampler (A600, Stratedigm). Before running measurements, cells were diluted by ~10-fold into phosphate buffered saline (PBS) in 384-well plates. Forward scatter (FSC) was used for the trigger, and ~40,000 individual cells were recorded. Cell populations were gated according to their FSC and side scatter (SSC) distributions, as described previously[7,33] (see FIG. 11 for representative gating data). The GFP fluorescence signal outputs of these gated cells were used for the following calculations. Error levels for the fluorescence measurements of ON-state and OFF-state cells were calculated from the SD of measurements from at least three biological replicates. The relative error levels for the ON/OFF fluorescence ratios were then determined by adding the relative errors of ON- and OFF-state fluorescence in quadrature.

Cell-Free Reactions

Cell-free transcription-translation systems (NEB, PUR-Express) were prepared for freeze-drying according to folby MilliporeSigma), 2%; chlorophenol red-b-D-galactopyranoside (Roche, 10884308001, distributed by MilliporeSigma, 24 mg/ml), 2.5%; with the remaining volume reserved for LIRA riboregulator or gate RNA plasmids, water, and lacZ α peptide added to a final concentration of 2 μM. When testing LIRA riboregulators from a plasmid, the plasmid DNA was added to a final concentration of 30 ng/μl in the cell-free reaction mix. For gate RNA devices tested in the paper-based system, the final concentration of the plasmid was 15 ng/μl.

Filter paper (Whatman, 1442-042) for depositing and freeze-drying the cell-free system was first blocked with 5% bovine serum albumin (BSA) overnight. The paper was washed three times in water for 5 to 10 min after overnight blocking. The paper was transferred on a hot plate at 50° C. for drying and then cut into 2-mm diameter paper disks with a biopsy punch. The disks were then transferred into 200-μl PCR strips and 1.8 μl of the above cell-free reaction mix was applied to each of them. Liquid nitrogen was used for freezing the PCR strips containing those paper devices. The frozen paper disks were dried overnight in a lyophilizer. Plate reader tests were carried out on the freeze-dried paper disks 2-4 days later. The systems were stored in a nitrogen environment shielded from light along with silica gel desiccation packages, as described previously[14]. The paper disks remained active for at least a month under storage at room temperature.

NASBA Reactions

NASBA experiments were carried out using following the standard protocols: reaction buffer (Life Sciences, NECB- 24; 33.5%), nucleotide mix (Life Sciences NECN-24; 16.5%), RNase inhibitor (Roche, 03335402001; 0.5%), and 12.5 μM of each DNA primer (2%), nuclease-free water (2.5%), and RNA amplicon (20%) were assembled at 4° C. After being incubated at 65° C. for 2 min and then at 41° C. for 10 min, 1.25 μl of enzyme mix (Life Sciences NEC-1-24; 25%) was added to the reaction. The reaction took place at 41° C. for 2 h and was then diluted 1:6 into water before applying 2 μl to the freeze-dried paper devices. For the dengue samples, de-identified clinical serum samples positive and negative for the virus were obtained at Salud Digna (Culiacan, Mexico) and provided as remnant biospecimens. The sample was first diluted 10-fold into water and then heated for 2 min at 95° C. for RNA release. The heat-extracted RNA was then added to the NASBA reaction. Heat-inactivated de-identified saliva samples that were positive and negative for SARS-CoV-2 were provided by the Arizona State University Biodesign Institute Clinical Testing Lab. Heat inactivation was performed by incubating samples at 65° C. for 30 min. The saliva samples were diluted 1:1 into water and heated at 95° C. for 2 min before spiking in NASBA reactions. A 1-μl aliquot of each sample was transferred into a 5-μl NASBA reaction. Each sample was amplified using separate NASBA reactions with the corresponding primer pairs designed for each input RNA. After a 2-hour reaction, 1 μl of each pair of NASBA products was combined and diluted with 5 μl water before adding 2 μL to the paper-based cell-free reaction.

RT-qPCR Reactions

Primers were designed to amplify both the GFP gene and 16S rRNA, which was used as the internal control. Colonies with bacteria transformed with LIRA plasmids and cognate or non-cognate input plasmids were inoculated into 6 ml LB in triplicate with appropriate antibiotics. Total RNA was extracted with a commercial RNA miniprep kit (Zymo Research, R2014) following the manufacturer-recommended protocol. Reverse transcription was performed using a commercial kit (Qiagen, 205311) with the manufacturer-recommended protocol. PCR was performed with a commercial kit (Life Technologies, 4367659) and measured by the Mx3005P qPCR system. The primers used for RT-qPCR are listed in Table 3. A no-RT control experiment was performed to confirm that no detectable DNA was present. Melting curve analysis confirmed that the qPCR product was correct.

TABLE 3

RT-qPCR primers for GFP and 16S rRNA

| Name | Sequence |
|---|---|
| qPCR1_GFP102_60C_fwd | AGGTGATGCAACATACGGAA (SEQ ID NO: 185) |
| qPCR1_GFP211_60C_rev | TGATCTGGGTATCTCGCAAA (SEQ ID NO: 186) |
| qPCR2_GFP222_60C_fwd | CCCAGATCACATGAAACAGC (SEQ ID NO: 187) |
| qPCR2_GFP310_60C_rev | GCACGTGTCTTGTAGTTCCC (SEQ ID NO: 188) |
| qPCR1_rrsA1107_60C_fwd | CGCAACCCTTATCCTTTGTT (SEQ ID NO: 189) |
| qPCR1_rrsA1194_60C_rev | TAAGGGCCATGATGACTTGA (SEQ ID NO: 190) |

TABLE 3-continued

RT-qPCR primers for GFP and 16S rRNA

| Name | Sequence |
|---|---|
| qPCR2_rrsA1236_60C_fwd | ACAATGGCGCATACAAAGAG (SEQ ID NO: 191) |
| qPCR2_rrsA1359_60C_rev | GTATTCACCGTGGCATTCTG (SEQ ID NO: 192) |

Results:

Multi-Arm Junctions for Controlling Gene Expression

Our general strategy for regulating gene expression using multi-arm junctions is illustrated in FIG. 1. In this strategy, a multi-arm nanostructure is placed at the 5' end of an mRNA and is followed by the coding sequence of a regulated gene. This configuration establishes strong secondary structures in the mRNA that conceal the ribosome binding site (RBS) and start codon (AUG) necessary to initiate translation. As a result, translation is repressed unless complementary input RNAs bind and unwind the structure. The stem-loop arms of the nanostructure act as sensors that provide binding sites for each of the input RNAs. The form of molecular logic evaluated by the multi-arm assembly is programmed by controlling the length and number of the sensor arms. OR logic is implemented using short sensor arms that remain "unlocked" and available for input RNA binding. Hybridization of either input RNA unwinds the cognate sensor arm through to the base stem to activate translation. To implement AND logic, all but one sensor arm is lengthened to establish a "locked" configuration that prevents binding by the corresponding input RNA. Binding of successive inputs unlocks additional sensor arms for input binding and ultimately allows the RNA strand to be fully unwound, activating translation of the downstream gene. Compared to other approaches for implementing logic-gated gene expression with RNAs, this strategy abolishes the need for any sequence correlations between input RNAs for AND operations. Moreover, it does not require extended N-terminal residues to be added to the output protein for OR operations, which can interfere with protein folding. Implementing this strategy, however, first required that we develop loop-based RNA-RNA interactions that functioned reliably in vivo to enable unwinding of the nanostructure through binding to the sensor arms.

Loop-Initiated Translational Activation

Figure 2:
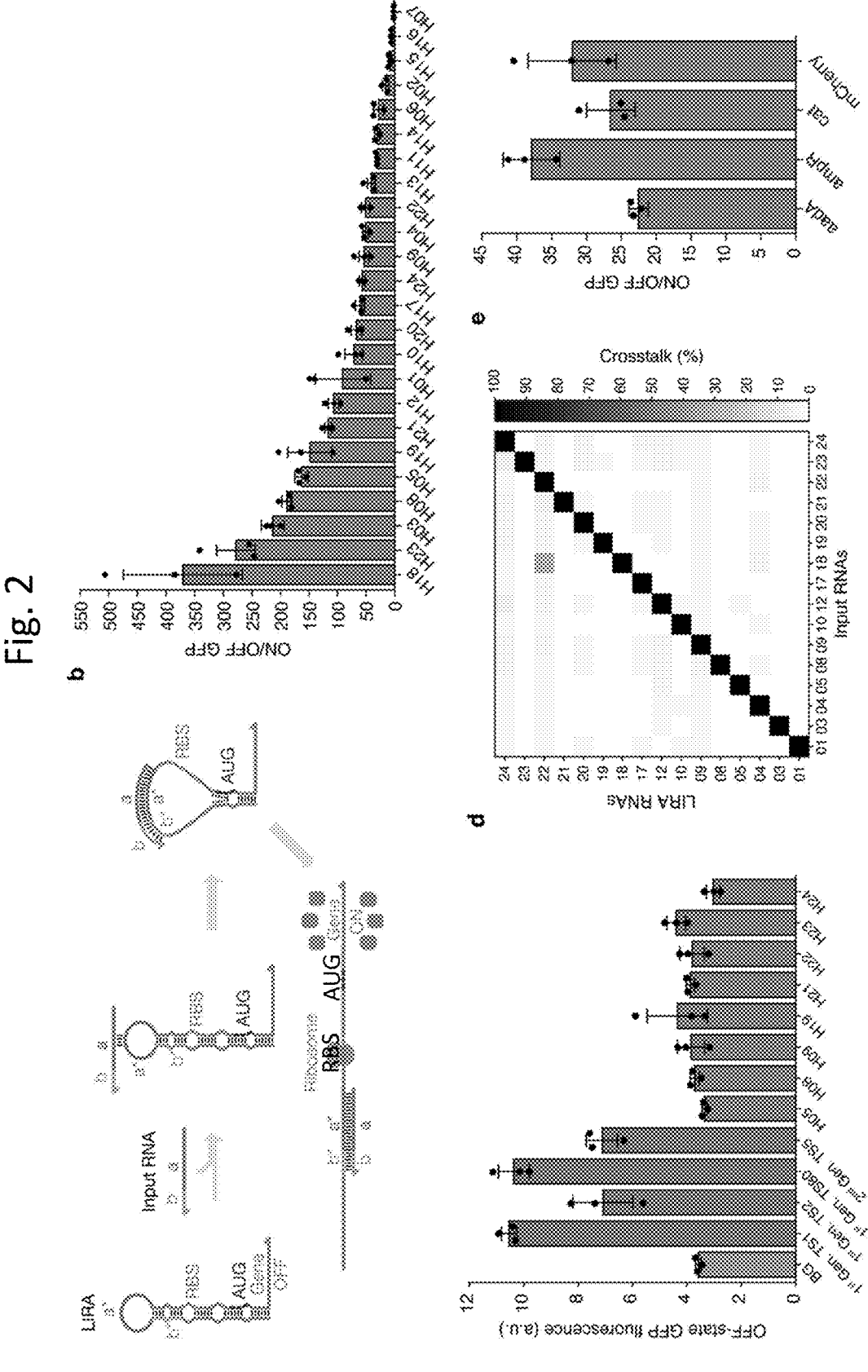
FIG. 2 shows the design and in vivo validation of loop-initiated RNA activators (LIRAs). a, Schematic of the LIRA design and its interaction mechanism with the input RNA. Binding between the input RNA and the LIRA loop domain triggers release of the ribosome binding site (RBS) and start codon (AUG) to activate translation. b, ON/OFF fluorescence ratios of a library of 24 different LIRAs. c, Leakage comparison of LIRAs and four toehold switches measuring GFP fluorescence in the absence of the input RNA. d, Crosstalk evaluation for 16 selected LIRA devices. e, Detection of full-length mRNAs using LIRAs. Measurements were taken 3 hours after induction with IPTG, n=3 biological replicates, bars represent the geometric mean±SD.
Figure 13:
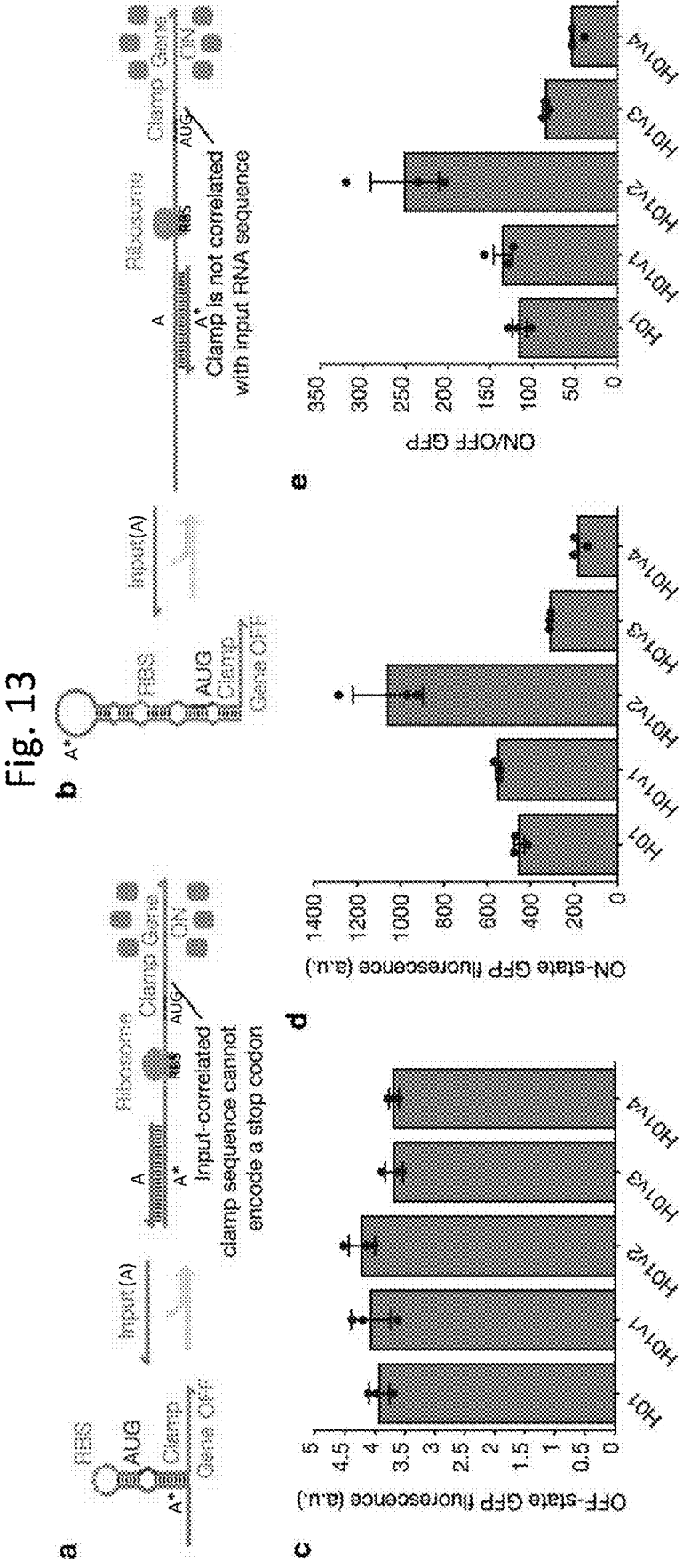
FIG. 13 shows a comparison of sequence constraints for toehold switches and LIRAs. a, The toehold switch contains a 9- to 12-nt stem sequence immediately after the start codon that is defined by the sequence of the input RNA. This clamp region cannot encode an in-frame stop codon, which in turn imposes sequence constraints on the input RNA sequence. The clamp also adds three to four N-terminal residues to the output protein. b, LIRAs employ a 6-bp clamp domain downstream of the start codon to achieve low translational leakage with high ON-state signals. This clamp domain is not correlated with the input RNA sequence but does incorporate two additional residues into the N-terminus of the output protein. c, Experimental study of the effect of different clamp sequences on the OFF-state GFP fluorescence of four LIRA H01 variants with different clamp sequences. OFF-state expression is unaffected by clamp sequence. d, Effect of different clamp sequences on the ON-state GFP fluorescence for LIRA H01 variants. e, ON/OFF fluorescence of LIRA H01 clamp variants. Significant variations in ON-state GFP and ON/OFF levels do occur, but all systems show ON/OFF levels greater than 50-fold. These results demonstrate that LIRAs can accommodate changes in clamp sequence and output protein N-terminal residues, while displaying good performance. n=3 biological replicates, bars represent the geometric mean±s.d. for c and d and the arithmetic mean±s.d. for e.

We thus developed a set of riboregulators designed to be integrated into the stem-loop regions of multi-arm junctions. While many recent high-performance riboregulators, such as toehold switches, have relied on single-stranded toehold domains to initiate reactions[38-40], we hypothesized that long loop domains could be utilized to provide similar performance. Such long loops would provide a strong thermodynamic driving force to initiate RNA-RNA interactions and provide an input RNA binding site that is sufficiently labile and unconstrained to offer good reaction kinetics. FIG. 2a shows the resulting loop-initiated RNA activators (LIRAs) that feature hairpins with extended loop domains regulating the expression of a downstream output gene. In the absence of the input RNA, translation by the LIRA is strongly repressed by sequestering both the RBS and the start codon of the output gene within the RNA duplex of the hairpin structure. A long loop domain a* of 21 nt is incorporated into the hairpin structure to promote the initial interaction between the LIRA and the activating RNA. After binding to the loop through the complementary a* sequence, the input RNA is designed to bind into the b* domain at the top of the hairpin stem, disrupting the existing base pairs and driving apart those located lower in the hairpin stem. Importantly, this effect enables the release of base pairs, in this case the RBS and start codon, that are completely unrelated to the sequence of the cognate input RNA. Thus, LIRAs can accommodate input RNAs without imposing any sequence constraints, and they can regulate a variety of different proteins without requiring modifications to the N-terminal sequence. In comparison, the design of toehold-switch riboregulators causes three to four N-terminal residues in the output protein to be defined by the sequence of the input RNA (FIG. 13a), which prevents recognition of input RNAs that would generate stop codons upstream of the output gene[7]. To enable efficient expression and testing in vivo, four bulges were incorporated into the LIRA hairpin structure to reduce the likelihood of premature rho-independent transcriptional termination and to increase the thermodynamics driving the input-LIRA reaction. A 6 bp clamp domain was also added immediately after the start codon in the LTRA stem to reduce the likelihood of translational leakage (FIG. 2a and FIG. 13b,c).

Figure 8:
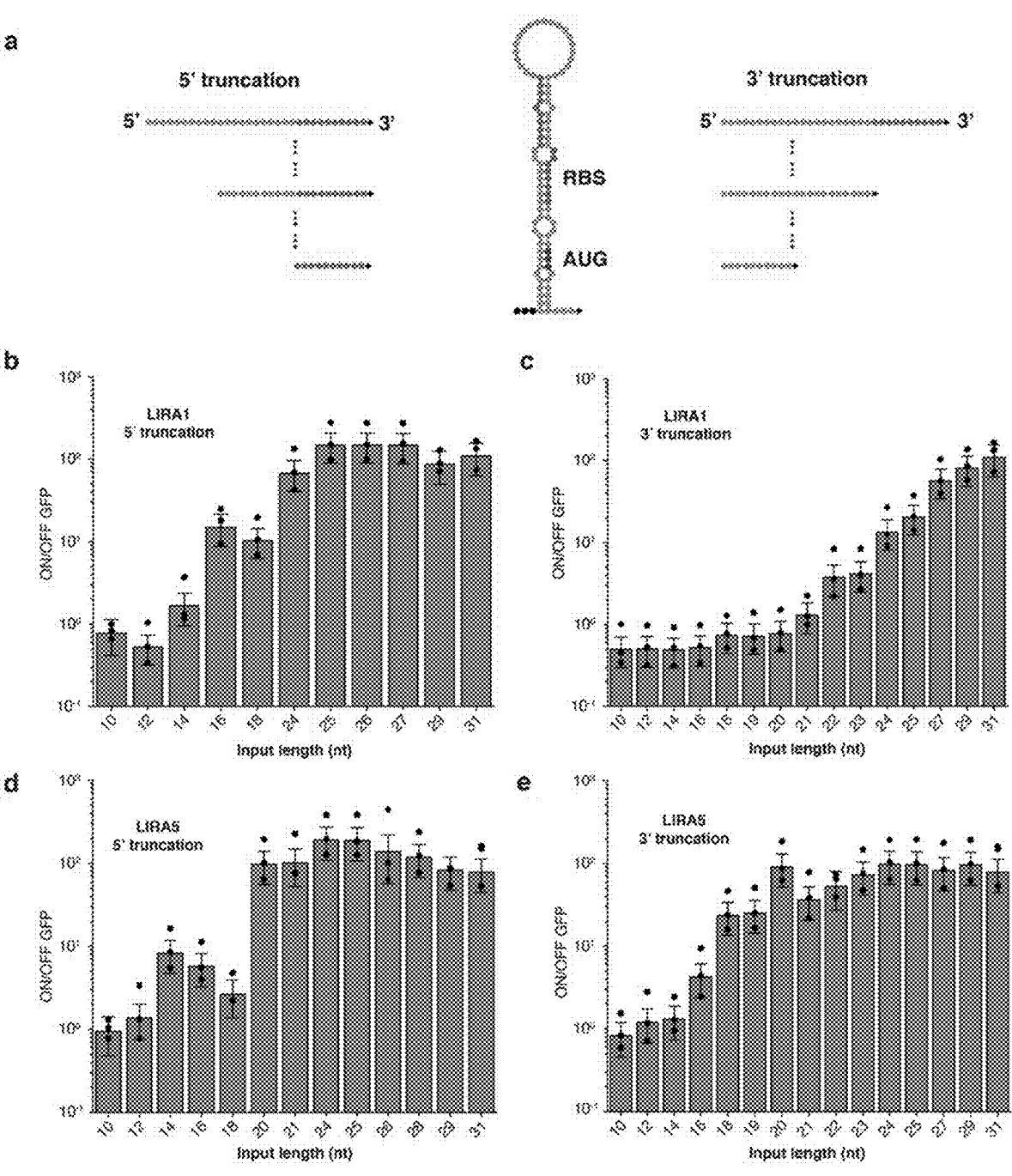
FIG. 8 shows testing of LIRAs with different input RNA lengths. a, Schematic of input RNAs truncated from the 5' and 3' ends. b, ON/OFF GFP fluorescence ratios of LIRA1 with inputs truncated from the 5' end. c, ON/OFF GFP fluorescence ratios of LIRA1 with inputs truncated from the 3' end. d, ON/OFF GFP fluorescence ratios of LIRA5 with inputs truncated from the 5' end. e, ON/OFF GFP fluorescence ratios of LIRA5 with inputs truncated from the 3' end. An input RNA length of 31 nt provides the best ON/OFF ratios overall, but shorter inputs can also achieve robust translation activation.
Figure 15:
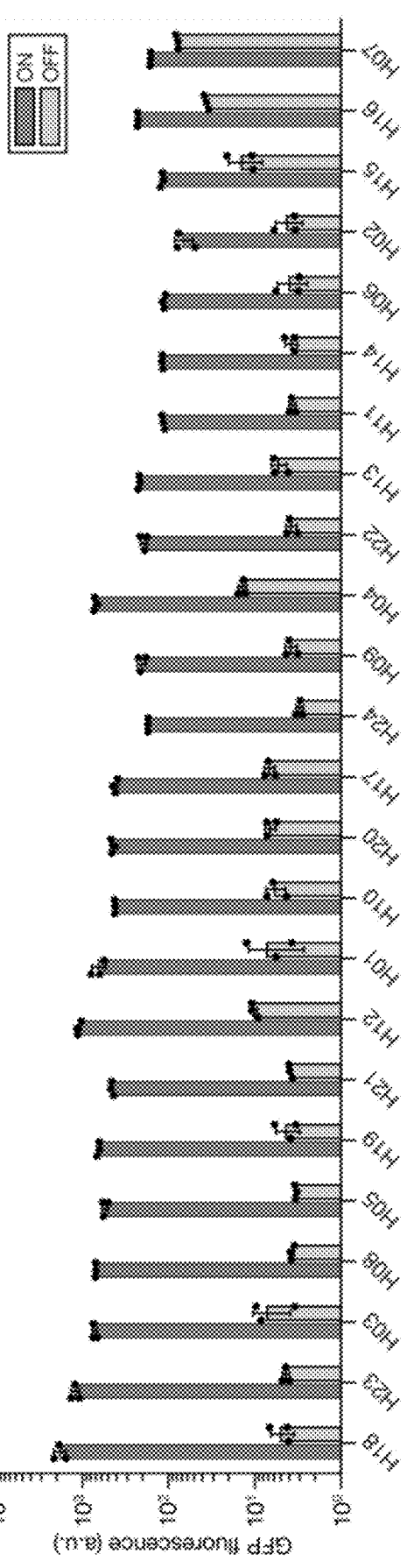
FIG. 15 shows the ON- and OFF-state signals ofall 24 LIRAs. Measurements were taken 3 hours after induction with IPTG, n=3 biological replicates, bars represent the geometric mean s.d.

A library of 24 different LIRA sequences were designed de novo using the NUPACK software package[41] and plasmids were constructed to express the input and LIRA transcripts using T7 RNA polymerase in E. coli BL21 Star DE3 cells (see Table 2 and Table 4 for primer and LIRA sequences). These experiments employed GFP as the reporter protein and measured fluorescence from the cells using flow cytometry. ON/OFF ratios for the LTRAs were determined by measuring the ON-state GFP expression in the presence of the cognate input and dividing it by the GFP expression measured in the OFF state where a non-cognate input was expressed in the cell (FIG. 2b, LIRA ON and OFF values are shown in FIG. 15). We found that 16 out of 24 of the LIRAs provided ON/OFF ratios over 50-fold, with the highest one yielding an ON/OFF ratio of ~350-fold. Additional tests using input RNAs complementary to different regions of the LIRA hairpin and different loop domain lengths revealed that the base LIRA design with a loop of 21 nt and a 31-nt input RNA provides the best overall performance (FIGS. 7 and 8; sequences are listed in Table 5 and Table 6).

TABLE 4

Sequences of the library of 24 LIRAs

| Name | Sequence | Terminator |
|---|---|---|
| LIRA_hairpin_1 | GGGTCTATCTATTTCACATCTCCTAAGTTTCCGTA TTCTGTGAAGCCCTAGGGTCCGATACAGAAACAG AGGAGATGACAAATGAATAGAAACCTGGCGGCA GCGCAAAAG (SEQ ID NO: 17) | N/A |
| LIRA_hairpin_2 | GGGTCCATTCATATACTATCTCCTAAGTTCTCGTT CCAATTCGCTCTCGTCCTGTCCGAACAAGAACAG AGGAGATAAGATATGAATGGAAACCTGGCGGCAG CGCAAAAG (SEQ ID NO: 18) | N/A |
| LIRA_hairpin_3 | GGGCTTATCAATATCACATCTCCTACGTCTTTAGT CGCTTCGGGACAGTGTGCATCCGACTAAAGACAG AGGAGATGACATATGAATAAGAACCTGGCGGCAG CGCAAAAG (SEQ ID NO: 19) | N/A |
| LIRA_hairpin_4 | GGGCGTTGAAATCTGCTATCTCCTACGTATTAGTT TATGCTACCGTAAGCCTGTCTCAAACGAATACAG AGGAGATACAAGATGACAACGAACCTGGCGGCA GCGCAAAAG (SEQ ID NO: 20) | N/A |
| LIRA_hairpin_5 | GGGTAGTGCCATATCTTATCTCCTGAGTTTCATCT TAAAGTCCTTGTAACAGTCGTCAAGACGAAACAG AGGAGATAACATATGACACTAAACCTGGCGGCAG CGCAAAAG (SEQ ID NO: 21) | N/A |
| LIRA_hairpin_6 | GGGATGTCCAATTACCTGTCTCCTGAGTCTACTCT ACCTCGCTCGTTCTCATGACTCTAGAATAGACAGA GGAGACACATAATGGGACATAACCTGGCGGCAGC GCAAAAG (SEQ ID NO: 22) | N/A |
| LIRA_hairpin_7 | GGGCATTGGAATCGAGTATCTCCTACGTTTAACTT AACCCTATACCCTCATAACCCTTAAGATAAACAG AGGAGATATACGATGGCAATGAACCTGGCGGCAG CGCAAAAG (SEQ ID NO: 23) | N/A |
| LIRA_hairpin_8 | GGGATGTACAATCCATTATCTCCTAAGTCTTATTC TACTGCCTTGTTCCACTCCCGTAGAACAAGACAGA GGAGATAACGGATGATACATAACCTGGCGGCAGC GCAAAAG (SEQ ID NO: 24) | N/A |
| LIRA_hairpin_9 | GGGCATTACAATTACCTATCTCCTACATTCTAGTG CCACGAGTTAGTATCTTCGCCTGCACAAGAATAG AGGAGATAGATAATGGTAATGAACCTGGCGGCAG CGCAAAAG (SEQ ID NO: 25) | N/A |

TABLE 4-continued

| Name | Sequence | Terminator |
|------|----------|------------|
| LIRA_hairpin_10 | GGGCATATGAATCGGAAGTCTCCTACAGTCATTTC GTCTTCGAGGCCGTCTCATCTGCGAACTGACTAGA GGAGACTAACGATGAATATGAACCTGGCGGCAGC GCAAAG (SEQ ID NO: 26) | N/A |
| LIRA_hairpin_11 | GGGCATCACAATTACATATCTCCTGAATCTTCATT CCATTCCATTGTCTCCAGACCGGAATGAAGATAG AGGAGATAGATAATGATGATGAACCTGGCGGCAG CGCAAAG (SEQ ID NO: 27) | N/A |
| LIRA_hairpin_12 | GGGATCATAGATGCAGTATCTCCTAAACTTCCACT TCGATCGCAGGTTTCACACTACAAGTAGAAGTAG AGGAGATAACGCATGAATGATAACCTGGCGGCAG CGCAAAG (SEQ ID NO: 28) | N/A |
| LIRA_hairpin_13 | GGGTCGTTCAATGTAGTATCTCCTAAGTCGTTTCT AGTACGAGATCGCCTGTTCCCATAGATACGACAG AGGAGATAAGACATGAAACGAAACCTGGCGGCA GCGCAAAG (SEQ ID NO: 29) | N/A |
| LIRA_hairpin_14 | GGGCATTTGCATATACCATCTCCTAAGTCTTATTC GTGACGCTTAAGTCCCGCAGAGCGAATAAGACAG AGGAGATGAGATATGGAAATGAACCTGGCGGCAG CGCAAAG (SEQ ID NO: 30) | N/A |
| LIRA_hairpin_15 | GGGCCATACAATCAACCGTCTCCTAAGTATTCCAA TACCGTGTCAATCTCTATAAGCATTGAAATACAGA GGAGACGGATGATGATATGGAACCTGGCGGCAGC GCAAAG (SEQ ID NO: 31) | N/A |
| LIRA_hairpin_16 | GGGCAATTACATGCAACGTCTCCTACATTCTTATC TATCAAAGTTCACGCACTACGCAGATAAGAATAG AGGAGACGAAGCATGAAATTGAACCTGGCGGCAG CGCAAAG (SEQ ID NO: 32) | N/A |
| LIRA_hairpin_17 | GGGACTCTACATGTACTATCTCCTACGTTTATCTA TGCTCCTATATCGTCACGTCTGATAGATAAACAGA GGAGATAAGACATGCAGAGTAACCTGGCGGCAGC GCAAAG (SEQ ID NO: 33) | N/A |
| LIRA_hairpin_18 | GGGATCTACCATTCATTATCTCCTAGGTTTCAGTT CTATTAGGGCTACGAAGACCGTGAACAGAAACAG AGGAGATACGGAATGATAGATAACCTGGCGGCAG CGCAAAG (SEQ ID NO: 34) | N/A |
| LIRA_hairpin_19 | GGGCTTATACATTTACCGTCTCCTAAGCTTAGTCG TGAAACCTATACAATCCTGTGCACGAATAAGCAG AGGAGACGACAAATGAATAAGAACCTGGCGGCA GCGCAAAG (SEQ ID NO: 35) | N/A |
| LIRA_hairpin_20 | GGGCTTAGCAATGTAGAATCTCCTGAGTTAGTTCC CATTGTTACTTTCACATCTCACGGGAACTAACAGA GGAGATTGAACATGACTAAGAACCTGGCGGCAGC GCAAAG (SEQ ID NO: 36) | N/A |
| LIRA_hairpin_21 | GGGCCTAACAATGTACCGTCTCCTAAGTCTCGATC CCGGTATCTTATGGCCTGGTCGGGATAGAGACAG AGGAGACGAAACATGATTAGGAACCTGGCGGCAG CGCAAAG (SEQ ID NO: 37) | N/A |
| LIRA_hairpin_22 | GGGCTTATCCATTTCACGTCTCCTACGCCTTCATC GTCGTCTTGCACCGTCCTACTCCGATAAAGGCAGA GGAGACGACAAATGAATAAGAACCTGGCGGCAG CGCAAAG (SEQ ID NO: 38) | N/A |
| LIRA_hairpin_23 | GGGCCTAACAATTCTATATCTCCTAAGTGTCAGTT CTTAGGCTACACATGTGAGTGTGAACAGACACAG AGGAGATAACGAATGATTAGGAACCTGGCGGCAG CGCAAAG (SEQ ID NO: 39) | N/A |

TABLE 4-continued

| Sequences of the library of 24 LIRAs | | |
|---|---|---|
| Name | Sequence | Terminator |
| LIRA_hairpin_24 | GGGCTTATCAATTGCACATCTCCTAGGTCATCTCG TCCAAATCGATCATCACTGTCCACGAGATGACAG AGGAGATGAACAATGGATAAGAACCTGGCGGCA GCGCAAAG (SEQ ID NO: 40) | N/A |
| LIRA_trigger_1 | GGGCCAGTGACTTGTCACTGGGAACGGACCCTAG GGCTTCACAGAATACGGAAACGAC (SEQ ID NO: 41) | T7 terminator |
| LIRA_trigger_2 | GGGAGTGGCACGCGTGCCACTAATGGACAGGACG AGAGCGAATTGGAACGAGAACGAC (SEQ ID NO: 42) | T7 terminator |
| LIRA_trigger_3 | GGGTCTCCACGGAAGTGGAGATAAGGATGCACAC TGTCCCGAAGCGACTAAAGACAAA (SEQ ID NO: 43) | T7 terminator |
| LIRA_trigger_4 | GGGCACGGACTCCTGTCCGTGGGCGAGACAGGCT TACGGTAGCATAAACTAATACAAC (SEQ ID NO: 44) | T7 terminator |
| LIRA_trigger_5 | GGGCTCACCTGCCAAGGTGAGAGCGACGACTGTT ACAAGGACTTTAAGATGAAACGAC (SEQ ID NO: 45) | T7 terminator |
| LIRA_trigger_6 | GGGCTGGAGCATACGCTCCAGAATGAGTCATGAG AACGAGCGAGGTAGAGTAGACGAA (SEQ ID NO: 46) | T7 terminator |
| LIRA_trigger_7 | GGGACAATGTAAGAACATTGTACGAGGGTTATGA GGGTATAGGGTTAAGTTAAACAGC (SEQ ID NO: 47) | T7 terminator |
| LIRA_trigger_8 | GGGATCCTGAATACTCAGGATGAAACGGGAGTGG AACAAGGCAGTAGAATAAGACAAC (SEQ ID NO: 48) | T7 terminator |
| LIRA_trigger_9 | GGGTCCGATCTAGAGATCGGATAAAGGCGAAGAT ACTAACTCGTGGCACTAGAATACA (SEQ ID NO: 49) | T7 terminator |
| LIRA_trigger_10 | GGGATCCAGCCGATGCTGGATGAACAGATGAGAC GGCCTCGAAGACGAAATGACTAGA (SEQ ID NO: 50) | T7 terminator |
| LIRA_trigger_11 | GGGAGCCATCGCATGATGGCTGGACGGTCTGGAG ACAATGGAATGGAATGAAGATACT (SEQ ID NO: 51) | T7 terminator |
| LIRA_trigger_12 | GGGCAGCTACTCAAGTAGCTGGAGGTAGTGTGAA ACCTGCGATCGAAGTGGAAGTACG (SEQ ID NO: 52) | T7 terminator |
| LIRA_trigger_13 | GGGAGTCAGCTGATGCTGACTAAGTGGGAACAGG CGATCTCGTACTAGAAACGACAAT (SEQ ID NO: 53) | T7 terminator |
| LIRA_trigger_14 | GGGCGTCACCTTTAGGTGACGGAACTCTGCGGGA CTTAAGCGTCACGAATAAGACACA (SEQ ID NO: 54) | T7 terminator |
| LIRA_trigger_15 | GGGCAGACCCTGCTGGGTCTGGACGCTTATAGAG ATTGACACGGTATTGGAATACAAA (SEQ ID NO: 55) | T7 terminator |
| LIRA_trigger_16 | GGGACGTTACTTAGGTAACGTGGAGCGTAGTGCG TGAACTTTGATAGATAAGAATGAA (SEQ ID NO: 56) | T7 terminator |
| LIRA_trigger_17 | GGGAGCTCGCAACCGCGAGCTAGACAGACGTGAC GATATAGGAGCATAGATAAACTCA (SEQ ID NO: 57) | T7 terminator |
| LIRA_trigger_18 | GGGAGCATGCCGTGGCATGCTAGGACGGTCTTCG TAGCCCTAATAGAACTGAAACATG (SEQ ID NO: 58) | T7 terminator |

TABLE 4-continued

| | Sequences of the library of 24 LIRAs | |
|---|---|---|
| Name | Sequence | Terminator |
| LIRA_trigger_19 | GGGCACAGACGTACGTCTGTGGAAGCACAGGATT GTATAGGTTTCACGACTAAGCGAA (SEQ ID NO: 59) | T7 terminator |
| LIRA_trigger_20 | GGGCCTACGCACTCGCGTAGGATTGTGAGATGTG AAAGTAACAATGGGAACTAACGAA (SEQ ID NO: 60) | T7 terminator |
| LIRA_trigger_21 | GGGCCAGACCATCGGGTCTGGAGGCGACCAGGCC ATAAGATACCGGGATCGAGACAAC (SEQ ID NO: 61) | T7 terminator |
| LIRA_trigger_22 | GGGACCGTACTCCCGTACGGTGATGAGTAGGACG GTGCAAGACGACGATGAAGGCTAC (SEQ ID NO: 62) | T7 terminator |
| LIRA_trigger_23 | GGGATGATCGACACCGATCATAGAACACTCACAT GTGTAGCCTAAGAACTGACACAGC (SEQ ID NO: 63) | T7 terminator |
| LIRA_trigger_24 | GGGCTGCTCCCGTGGGAGCAGGACGGACAGTGAT GATCGATTTGGACGAGATGACATA (SEQ ID NO: 64) | T7 terminator |

TABLE 5

| | Sequences of LIRA variants with different loop lengths |
|---|---|
| Name | Sequence |
| LIRA_hairpin_1_loop03 | GGGTCTATCTATTTCACATCTCCTAAGTTTCCGTATTCTATACA GAAACAGAGGAGATGACAAATGAATAGAAACCTGGCGGCAGC GCAAAG (SEQ ID NO: 121) |
| LIRA_hairpin_1_loop06 | GGGTCTATCTATTTCACATCTCCTAAGTTTCCGTATTCTGTGAT ACAGAAACAGAGGAGATGACAAATGAATAGAAACCTGGCGGC AGCGCAAAG (SEQ ID NO: 122) |
| LIRA_hairpin_1_loop09 | GGGTCTATCTATTTCACATCTCCTAAGTTTCCGTATTCTGTGAA GATACAGAAACAGAGGAGATGACAAATGAATAGAAACCTGGC GGCAGCGCAAAG (SEQ ID NO: 123) |
| LIRA_hairpin_1_loop12 | GGGTCTATCTATTTCACATCTCCTAAGTTTCCGTATTCTGTGAA GCCCATACAGAAACAGAGGAGATGACAAATGAATAGAAACCT GGCGGCAGCGCAAAG (SEQ ID NO: 124) |
| LIRA_hairpin_1_loop15 | GGGTCTATCTATTTCACATCTCCTAAGTTTCCGTATTCTGTGAA GCCCTAGATACAGAAACAGAGGAGATGACAAATGAATAGAAA CCTGGCGGCAGCGCAAAG (SEQ ID NO: 125) |
| LIRA_hairpin_1_loop18 | GGGTCTATCTATTTCACATCTCCTAAGTTTCCGTATTCTGTGAA GCCCTAGGGTATACAGAAACAGAGGAGATGACAAATGAATAG AAACCTGGCGGCAGCGCAAAG (SEQ ID NO: 126) |
| LIRA_hairpin_5_loop03 | GGGTAGTGCCATATCTTATCTCCTGAGTTTCATCTTAAAAAGAC GAAACAGAGGAGATAACATATGACACTAAACCTGGCGGCAGC GCAAAG (SEQ ID NO: 127) |
| LIRA_hairpin_5_loop06 | GGGTAGTGCCATATCTTATCTCCTGAGTTTCATCTTAAAGTCAA GACGAAACAGAGGAGATAACATATGACACTAAACCTGGCGGC AGCGCAAAG (SEQ ID NO: 128) |
| LIRA_hairpin_5_loop09 | GGGTAGTGCCATATCTTATCTCCTGAGTTTCATCTTAAAGTCCT TAAGACGAAACAGAGGAGATAACATATGACACTAAACCTGGC GGCAGCGCAAAG (SEQ ID NO: 129) |
| LIRA_hairpin_5_loop12 | GGGTAGTGCCATATCTTATCTCCTGAGTTTCATCTTAAAGTCCT TGTAAAGACGAAACAGAGGAGATAACATATGACACTAAACCT GGCGGCAGCGCAAAG (SEQ ID NO: 130) |

TABLE 5-continued

Sequences of LIRA variants with different loop lengths

| Name | Sequence |
|------|----------|
| LIRA_hairpin_5_loop15 | GGGTAGTGCCATATCTTATCTCCTGAGTTTCATCTTAAAGTCCT TGTAACAAAGACGAAACAGAGGAGATAACATATGACACTAAA CCTGGCGGCAGCGCAAAAG (SEQ ID NO: 131) |
| LIRA_hairpin_5_loop18 | GGGTAGTGCCATATCTTATCTCCTGAGTTTCATCTTAAAGTCCT TGTAACAGTCAAGACGAAACAGAGGAGATAACATATGACACT AAACCTGGCGGCAGCGCAAAAG (SEQ ID NO: 132) |

TABLE 6

Sequences of truncated LIRA input RNAs

| Name | Sequence | Terminator |
|------|----------|------------|
| LIRA1_complete_len31 | GGGCGGACCCTAGGGCTTCACAGAATACGGAA AC (SEQ ID NO: 133) | T7 terminator |
| LIRA1_trunc3_len10 | GGGCGGACCCTAG (SEQ ID NO: 134) | T7 terminator |
| LIRA1_trunc3_len12 | GGGCGGACCCTAGGG (SEQ ID NO: 135) | T7 terminator |
| LIRA1_trunc3_len14 | GGGCGGACCCTAGGGCT (SEQ ID NO: 136) | T7 terminator |
| LIRA1_trunc3_len16 | GGGCGGACCCTAGGGCTTC (SEQ ID NO: 137) | T7 terminator |
| LIRA1_trunc3_len18 | GGGCGGACCCTAGGGCTTCAC (SEQ ID NO: 138) | T7 terminator |
| LIRA1_trunc3_len19 | GGGCGGACCCTAGGGCTTCACA (SEQ ID NO: 139) | T7 terminator |
| LIRA1_trunc3_len20 | GGGCGGACCCTAGGGCTTCACAG (SEQ ID NO: 140) | T7 terminator |
| LIRA1_trunc3_len21 | GGGCGGACCCTAGGGCTTCACAGA (SEQ ID NO: 141) | T7 terminator |
| LIRA1_trunc3_len22 | GGGCGGACCCTAGGGCTTCACAGAA (SEQ ID NO: 142) | T7 terminator |
| LIRA1_trunc3_len23 | GGGCGGACCCTAGGGCTTCACAGAAT (SEQ ID NO: 143) | T7 terminator |
| LIRA1_trunc3_len24 | GGGCGGACCCTAGGGCTTCACAGAATA (SEQ ID NO: 144) | T7 terminator |
| LIRA1_trunc3_len25 | GGGCGGACCCTAGGGCTTCACAGAATAC (SEQ ID NO: 145) | T7 terminator |
| LIRA1_trunc3_len27 | GGGCGGACCCTAGGGCTTCACAGAATACGG (SEQ ID NO: 146) | T7 terminator |
| LIRA1_trunc3_len29 | GGGCGGACCCTAGGGCTTCACAGAATACGGAA (SEQ ID NO: 147) | T7 terminator |
| LIRA1_trunc5_len10 | GGGATACGGAAAC (SEQ ID NO: 148) | T7 terminator |
| LIRA1_trunc5_len12 | GGGAATACGGAAAC (SEQ ID NO: 149) | T7 terminator |
| LIRA1_trunc5_len14 | GGGCAGAATACGGAAAC (SEQ ID NO: 150) | T7 terminator |
| LIRA1_trunc5_len16 | GGGCACAGAATACGGAAAC (SEQ ID NO: 151) | T7 terminator |
| LIRA1_trunc5_len18 | GGGTTCACAGAATACGGAAAC (SEQ ID NO: 152) | T7 terminator |

TABLE 6-continued

Sequences of truncated LIRA input RNAs

| Name | Sequence | Terminator |
|---|---|---|
| LIRA1_trunc5_len25 | GGGCTAGGGCTTCACAGAATACGGAAAC (SEQ ID NO: 153) | T7 terminator |
| LIRA1_trunc5_len26 | GGGCCTAGGGCTTCACAGAATACGGAAAC (SEQ ID NO: 154) | T7 terminator |
| LIRA1_trunc5_len27 | GGGCCCTAGGGCTTCACAGAATACGGAAAC (SEQ ID NO: 155) | T7 terminator |
| LIRA1_trunc5_len29 | GGGACCCTAGGGCTTCACAGAATACGGAAAC (SEQ ID NO: 156) | T7 terminator |
| LIRA5_complete_len31 | GGGACGACTGTTACAAGGACTTTAAGATGAAAC (SEQ ID NO: 157) | T7 terminator |
| LIRA5_trunc3_len10 | GGGACGACTGTT (SEQ ID NO: 158) | T7 terminator |
| LIRA5_trunc3_len12 | GGGACGACTGTTAC (SEQ ID NO: 159) | T7 terminator |
| LIRA5_trunc3_len14 | GGGACGACTGTTACAA (SEQ ID NO: 160) | T7 terminator |
| LIRA5_trunc3_len16 | GGGACGACTGTTACAAGG (SEQ ID NO: 161) | T7 terminator |
| LIRA5_trunc3_len18 | GGGACGACTGTTACAAGGAC (SEQ ID NO: 162) | T7 terminator |
| LIRA5_trunc3_len19 | GGGACGACTGTTACAAGGACT (SEQ ID NO: 163) | T7 terminator |
| LIRA5_trunc3_len20 | GGGACGACTGTTACAAGGACTT (SEQ ID NO: 164) | T7 terminator |
| LIRA5_trunc3_len21 | GGGACGACTGTTACAAGGACTTT (SEQ ID NO: 165) | T7 terminator |
| LIRA5_trunc3_len22 | GGGACGACTGTTACAAGGACTTTA (SEQ ID NO: 166) | T7 terminator |
| LIRA5_trunc3_len23 | GGGACGACTGTTACAAGGACTTTAA (SEQ ID NO: 167) | T7 terminator |
| LIRA5_trunc3_len24 | GGGACGACTGTTACAAGGACTTTAAG (SEQ ID NO: 168) | T7 terminator |
| LIRA5_trunc3_len25 | GGGACGACTGTTACAAGGACTTTAAGA (SEQ ID NO: 169) | T7 terminator |
| LIRA5_trunc3_len27 | GGGACGACTGTTACAAGGACTTTAAGATG (SEQ ID NO: 170) | T7 terminator |
| LIRA5_trunc3_len29 | GGGACGACTGTTACAAGGACTTTAAGATGAA (SEQ ID NO: 171) | T7 terminator |
| LIRA5_trunc5_len10 | GGGAAGATGAAAC (SEQ ID NO: 172) | T7 terminator |
| LIRA5_trunc5_len12 | GGGTTAAGATGAAAC (SEQ ID NO: 173) | T7 terminator |
| LIRA5_trunc5_len14 | GGGCTTTAAGATGAAAC (SEQ ID NO: 174) | T7 terminator |
| LIRA5_trunc5_len16 | GGGACTTTAAGATGAAAC (SEQ ID NO: 175) | T7 terminator |
| LIRA5_trunc5_len18 | GGGAGGACTTTAAGATGAAAC (SEQ ID NO: 176) | T7 terminator |
| LIRA5_trunc5_len20 | GGGCAAGGACTTTAAGATGAAAC (SEQ ID NO: 177) | T7 terminator |

TABLE 6-continued

Sequences of truncated LIRA input RNAs

| Name | Sequence | Terminator |
|------|----------|------------|
| LIRA5_trunc5_len21 | GGGACAAGGACTTTAAGATGAAAC (SEQ ID NO: 178) | T7 terminator |
| LIRA5_trunc5_len22 | GGGTACAAGGACTTTAAGATGAAAC (SEQ ID NO: 179) | T7 terminator |
| LIRA5_trunc5_len24 | GGGTTACAAGGACTTTAAGATGAAAC (SEQ ID NO: 180) | T7 terminator |
| LIRA5_trunc5_len25 | GGGTGTTACAAGGACTTTAAGATGAAAC (SEQ ID NO: 181) | T7 terminator |
| LIRA5_trunc5_len26 | GGGCTGTTACAAGGACTTTAAGATGAAAC (SEQ ID NO: 182) | T7 terminator |
| LIRA5_trunc5_len28 | GGGACTGTTACAAGGACTTTAAGATGAAAC (SEQ ID NO: 183) | T7 terminator |
| LIRA5_trunc5_len29 | GGGCGACTGTTACAAGGACTTTAAGATGAAAC (SEQ ID NO: 184) | T7 terminator |

Figure 9:
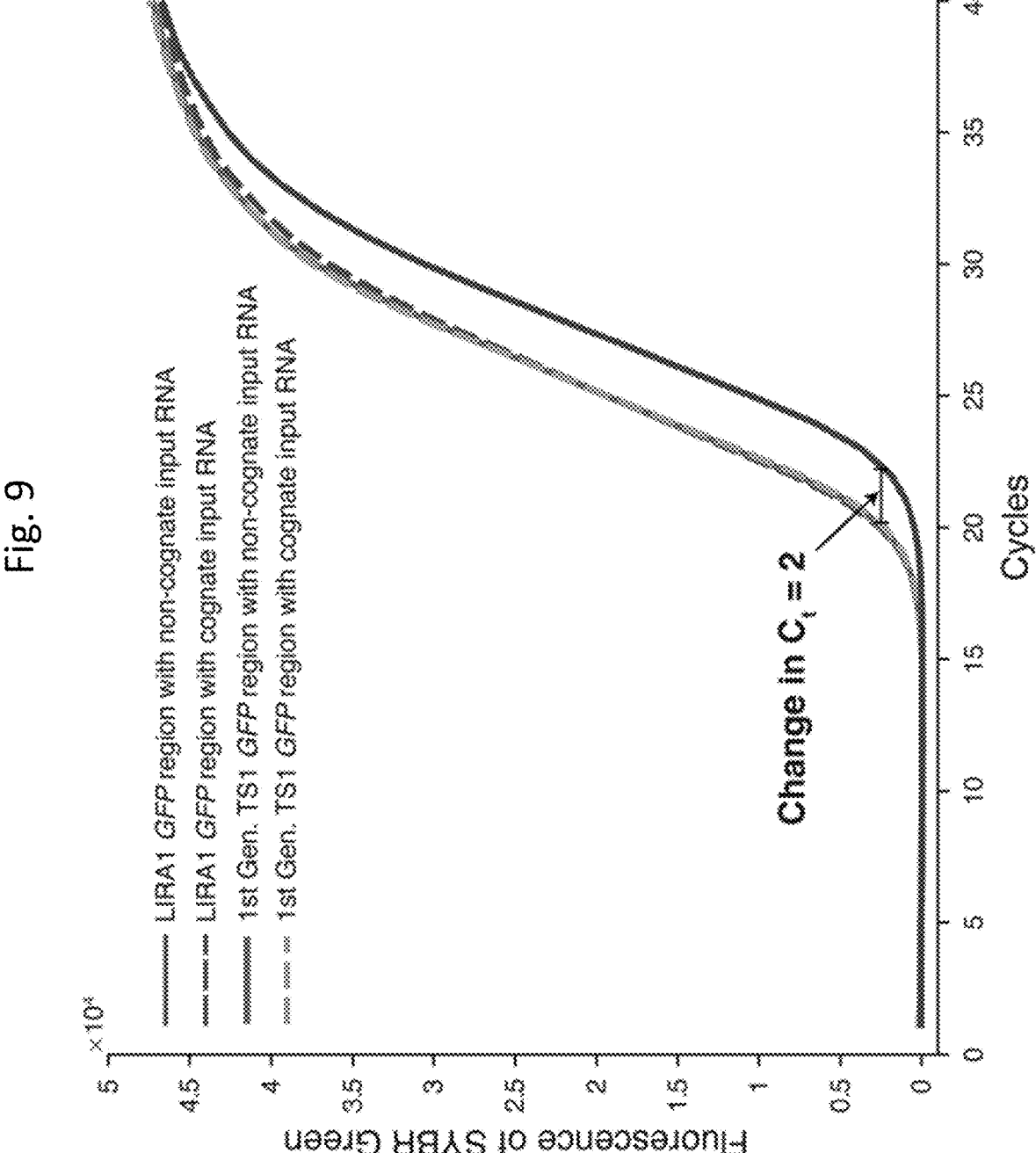
FIG. 9 shows RT-qPCR data for LIRA1 compared to first-generation toehold switch #1. RT-qPCR measurements were performed on the GFP gene downstream of the ribo-regulator hairpins. In absence of a cognate input RNA, the Ct value for the LIRA1 mRNA decreased by two compared to LIRA1 mRNA with the cognate input RNA. This result indicates a 4-fold decrease in LIRA1 mRNA levels without the input RNA and the presence of transcriptional regulation. In comparison, mRNA levels for toehold switch #1 (TS1) were unaffected by the expression of the input or trigger RNA. For normalization, RT-qPCR was also performed on the housekeeping 16S rRNA and showed the same Ct value across all samples.
Figure 14:
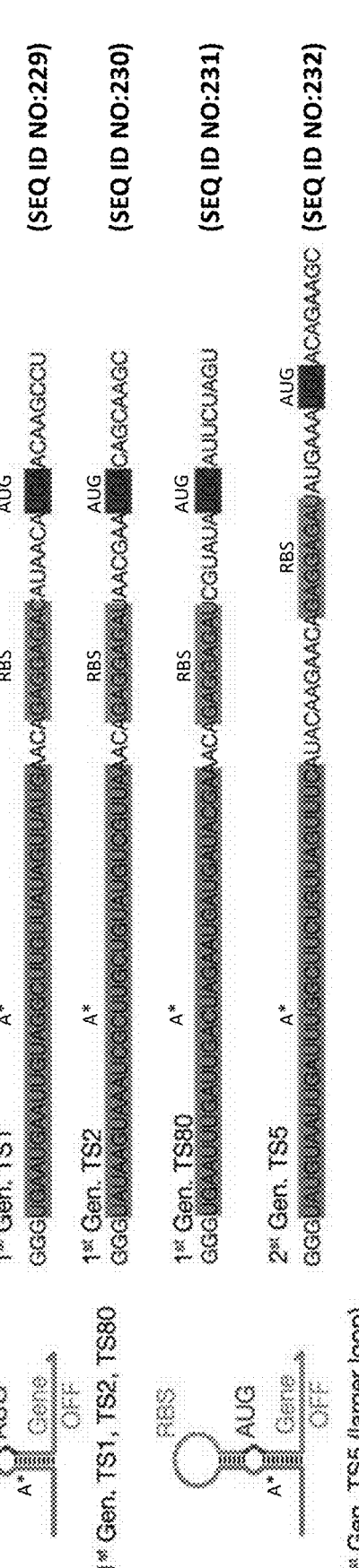
FIG. 14 shows transcriptional regulation of LIRAs and comparison to toehold switches. a, Structure and sequences of selected toehold switches used for testing translational leakage in FIG. 2c. b, ON-state GFP fluorescence of toehold switches and LIRAs tested for translational leakage in FIG. 2c. n=3 biological replicates, bars represent the geometric mean±s.d. c, Schematic of the putative transcriptional regulation mechanism of LIRAs. The strong hairpin structure of the LIRA can cause early transcriptional termination for some transcripts. In the presence of the input RNA, binding of the input prevents formation of the hairpin structure and promotes transcription of the full-length mRNA. d, Minimum free energy (MFE) of the T7 terminator and the hairpin structures of the toehold Switches and LIRAs from FIG. 2c. Toehold switches have a weaker secondary structure than the T7 terminator, which makes them unlikely candidates for transcriptional termination. LIRAs possess a longer hairpin structure and have a stronger secondary structure than the T7 terminator. The stronger hairpin structure is expected to encourage transcriptional termination, albeit at a lower rate than natural terminators that feature 3' U-tracts and short loop domains to promote faster hairpin formation.
Figure 14:
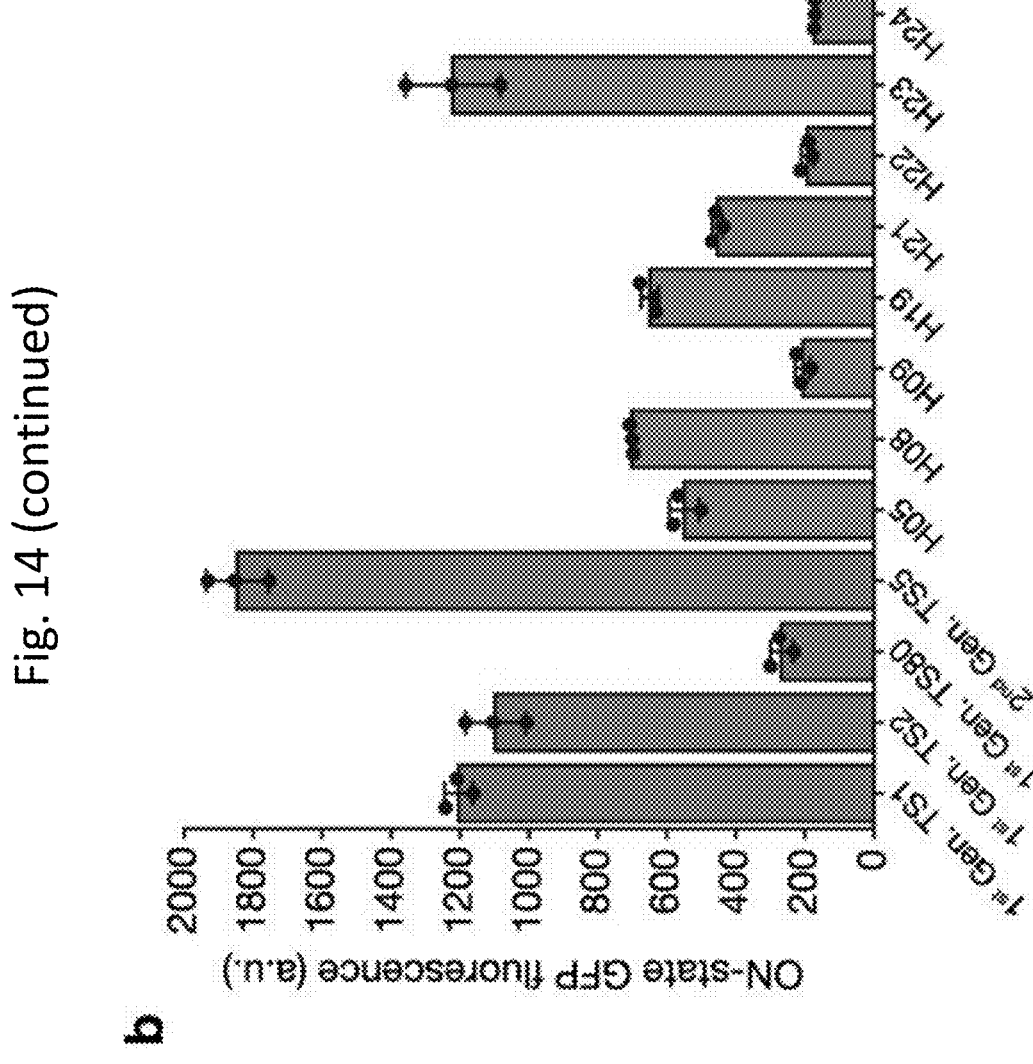

We observed that multiple LIRAs provided very low translational leakage in the absence of the input RNA. FIG. 2c shows the OFF-state GFP fluorescence of eight different LIRAs with ON/OFF ratios greater than 50 compared to the auto-fluorescence of cells lacking GFP and a set of previously reported toehold switch riboregulators with wide dynamic range[7] (FIG. 14a). We found that the toehold switches in the OFF-state yielded 2- to 3-fold higher fluorescence than the cells lacking GFP plasmids. In contrast, all eight of the LIRAs examined provided fluorescence leakage that was statistically indistinguishable from the background cellular fluorescence with p-values greater than 0.067 for all the LIRA devices in the plot compared to cell autofluorescence. Comparison of ON-state signals showed that three out of the four toehold switches provided higher signal output than the LIRAs (FIG. 14b). To explain the very low OFF-state signals, we hypothesized that low-leakage LIRAs could be making use of a combined translational and transcriptional regulation mechanism to yield virtually undetectable leakage (FIG. 14c), assisted by the strong secondary structure of the LIRA hairpin (see FIG. 14d for a comparison of minimum free energies for LIRA and toehold-switch hairpins). To verify this hypothesis, we performed reverse transcription quantitative polymerase chain reaction (RT-qPCR) experiments to measure the concentration of LIRA RNAs and cognate and non-cognate input RNAs expressed from cells in the ON and OFF states, respectively (FIG. 9). We found that expression of the LIRA transcript with a non-cognate input was only 25% of that measured for the transcript with a cognate input, confirming that part of the LIRA regulation is due to transcriptional control. We also studied a set of four LIRA variants that contained different sequences in the stem below the start codon (see Table 13 for sequence information), which in turn modify the N-terminal residues in the output protein. We found that these clamp sequence changes did not impact the OFF-state signal of the LIRAs (FIG. 13c), but they did cause variations in ON-state expression levels ranging from 40% to 230% of the parent LIRA (FIG. 13d). Despite these variations, all of the devices with clamp modifications displayed ON/OFF ratios of at least 50-fold (FIG. 13e), indicating that changes in clamp sequence and the N-terminal residues are well tolerated by the riboregulators.

TABLE 13

Sequences of LIRA H01 clamp variants

| Name | Sequence |
|------|----------|
| LIRA_H01 | GGGTCTATCTATTTCACATCTCCTAAGTTTCCGTATTCTGTGAAGCCCTAG GGTCCGATACAGAAACAGAGGAGATGACAAATGAATAGAAACCTGGCGG CAGCGCAAAAG (SEQ ID NO: 224) |
| LIRA_H01 v1 | GGGTCGTGCTATTTCACATCTCCTAAGTTTCCGTATTCTGTGAAGCCCTAG GGTCCGATACAGAAACAGAGGAGATGACAAATGACACGAAACCTGGCGG CAGCGCAAAAG (SEQ ID NO: 225) |
| LIRA_H01 v2 | GGGCTTATGTATTTCACATCTCCTAAGTTTCCGTATTCTGTGAAGCCCTAG GGTCCGATACAGAAACAGAGGAGATGACAAATGAATAAGAACCTGGCGG CAGCGCAAAAG (SEQ ID NO: 226) |
| LIRA_H01 v3 | GGGTCGTTGTATTTCACATCTCCTAAGTTTCCGTATTCTGTGAAGCCCTAG GGTCCGATACAGAAACAGAGGAGATGACAAATGGAACGAAACCTGGCGG CAGCGCAAAAG (SEQ ID NO: 227) |

TABLE 13-continued

| Sequences of LIRA H01 clamp variants | |
|---|---|
| Name | Sequence |
| LIRA_H01 v4 | GGGCTTGTCTATTTCACATCTCCTAAGTTTCCGTATTCTGTGAAGCCCTAG GGTCCGATACAGAAACAGAGGAGATGACAAATGAACAAGAACCTGGCGG CAGCGCAAAAG (SEQ ID NO: 228) |

Foreshadowing their use in multi-arm junctions, we evaluated LIRA orthogonality by measuring the crosstalk observed between the 16 devices providing the widest dynamic range. A 16×16 matrix of pairwise LIRA-input RNA interactions was measured by transforming cells with different combinations of plasmids. FIG. 2d shows the measured crosstalk between the devices. Cognate interactions along the diagonal are normalized to 1 for the riboregulators in their ON states, while off-diagonal, non-cogand chloramphenicol, respectively, was investigated (see Table 7 for sequence information). All LIRAs were based on a high-performance design identified during library screening and were generated simply by replacing the original target-binding site with the reverse complement of the mRNA target site. We found that all four mRNAs could be readily detected using the LIRAs and provided ON/OFF GFP levels ranging from 22- to 38-fold (FIG. 2e).

TABLE 7

| Sequences of mRNA-responsive LIRAs | | |
|---|---|---|
| Name | Sequence | Terminator |
| aadA_sensor | GGGATCTACCATTCATTATCTCCTAGAGGTTTC ATTTAGCGCCTCAAATAGATCCTGTTCAGTAAA TGTAACCTAGAGGAGATACGGAATGATAGATA ACCTGGCGGCAGCGCAAAAG (SEQ ID NO: 65) | N/A |
| ampR_sensor | GGGATCTACCATTCATTATCTCCTAGATCTGTCT ATTTCGTTCATCCATAGTTGCCTGACTGAAATA GACAGATAGAGGAGATACGGAATGATAGATAA CCTGGCGGCAGCGCAAAAG (SEQ ID NO: 66) | N/A |
| cat_sensor | GGGATCTACCATTCATTATCTCCTAGACGAAAA ACATATTCTCAATAAACCCTTTAGGGAAATATG TTATTCGTAGAGGAGATACGGAATGATAGATA ACCTGGCGGCAGCGCAAAAG (SEQ ID NO: 67) | N/A |
| mCherry_sensor | GGGATCTACCATTCATTATCTCCTAGCTTGGCCT TGTAGGTGGTCTTGACCTCAGCGTCGTATACAA GACCAAGAGAGGAGATACGGAATGATAGATAA CCTGGCGGCAGCGCAAAAG (SEQ ID NO: 68) | N/A |
| Name | Sequence (binding site of LIRA within full-length mRNA) | Terminator |
| aadA_trigger | GGGCTGAACAGGATCTATTTGAGGCGCTAAATG AAACCT (SEQ ID NO: 69) | T7 terminator |
| ampR_trigger | GGGATCTGTCTATTTCGTTCATCCATAGTTGCCT GACTG (SEQ ID NO: 70) | T7 terminator |
| cat_trigger | GGGTTTCCCTAAAGGGTTTATTGAGAATATGTT TTTCGT (SEQ ID NO: 71) | T7 terminator |
| mCherry_trigger | GGGTACGACGCTGAGGTCAAGACCACCTACAA GGCCAAG (SEQ ID NO: 72) | T7 terminator | nate interactions reflect the percent activation with respect to the ON state. We found that crosstalk from the non-cognate inputs was very low, less than 4% in nearly all cases with a single strong off-target interaction observed between LIRA 22 and input 18 showing 5.6% crosstalk. Thus, the LIRAs provided a set of 15 orthogonal devices for regulation of gene expression in vivo.

Based on their low crosstalk and lack of sequence constraints, we also investigated whether LIRAs could be designed to detect mRNAs within the cell. A set of LIRAs targeting regions of low secondary structure in the mRNAs for mCherry and the antibiotic resistance genes aadA, ampR, and cat, conferring resistance to spectinomycin, ampicillin, Multi-Arm RNA Junctions for In Vivo Molecular Logic Having developed a set of orthogonal LIRAs lacking sequence constraints, we next integrated them as sensing modules into the multi-arm RNA junction nanostructures for computing intracellular OR and AND logic expressions. The sensor arms of the resulting logic gate RNA are each capped by different LIRA modules and designed to direct the unfolding of the structure as input RNAs bind to the gate RNA. Two-input OR logic devices were constructed upstream of a GFP reporter using a three-arm junction containing a pair of LTRA sensor arms (FIG. 3a). The base arm contains the RBS and start codon signals topped by the LIRA arms to provide binding sites A* and B* for interaction with the complementary input RNAs A and B. Binding of either input RNA disrupts the cognate stem-loop structure and further draws apart the base arm to reveal the RBS and start codon for translation initiation. To increase translational output for this input and reduce the likelihood of transcriptional regulation, we also incorporated a hairpin reconfiguration domain (see "HRD" in FIG. 3a) that generated an additional stem-loop upon binding of input A to the gate RNA. This newly formed stem disrupted the bottom gray portion of the input B LIRA module, providing a single-stranded region upstream of the RBS and greater space to better accommodate the ribosomal footprint. During transcription, the hairpin domain can also help delay formation of the strong LIRA stem-loop structures to discourage transcriptional termination.

We tested the two-input OR device by transcribing the input and gate RNAs off separate high- and medium-copy plasmids, respectively, in E. coli (see Table 5 for sequence information). Using flow cytometry, we found that GFP expression increased by 38- to 84-fold when any combination of the two input RNAs was expressed (FIG. 3b,c). We also constructed a three-input OR gate RNA using three orthogonal LIRA modules (FIG. 3d). This four-arm junction system contained a base arm with the RBS and start codon and contained the LIRA stem loop for input C between modules for inputs A and B. Like the two-input device, the two left LIRA stem loops also contained hairpin reconfiguration domains to enable increased translation upon binding of inputs A and C. This circuit also performed as expected in vivo with low expression for the null-input logical FALSE case and 6- to 19-fold increases in expression when the input RNAs were expressed in any combination (FIG. 3e,f).

Figure 4:
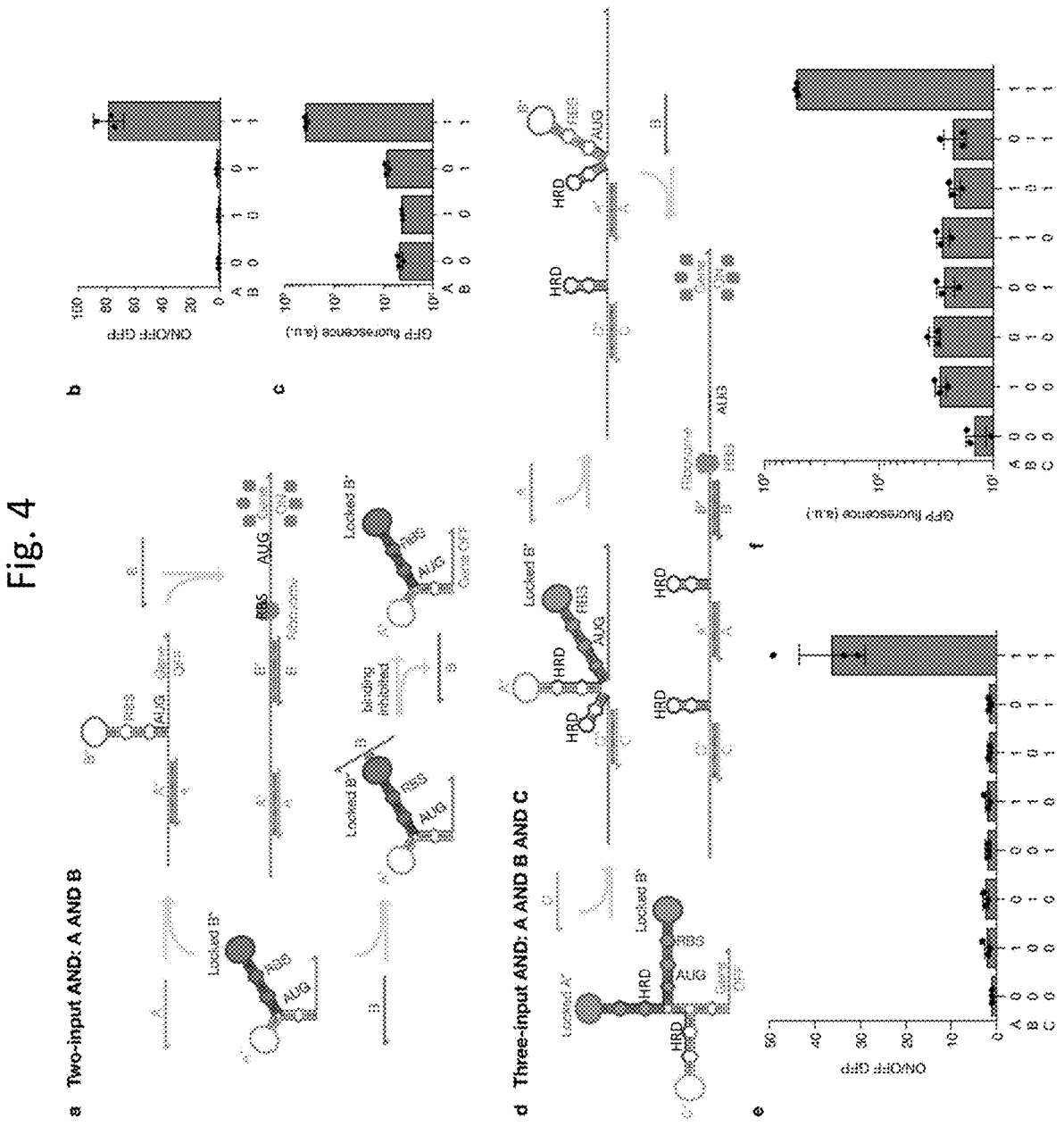
FIG. 4 depicts multi-arm RNA junction molecular AND logic in *E. coli* using hairpin reconfiguration domains (HRD). a, Schematic of the two-input AND logic design and its interaction mechanism with the input RNAs. b, ON/OFF fluorescence ratios for each input combination. c, GFP fluorescence for each input combination. d, Schematic of the three-input AND logic design and its interaction mechanism with the input RNAs. e, ON/OFF ratios for each input combination. f, GFP fluorescence for each input combination. All p values from two-tailed student's t-tests between each FALSE state and TRUE state are less than 0.05. Measurements were taken after 4 hours after induction with IPTG, n=3, bars represent the geometric mean±SD.
Figure 12:
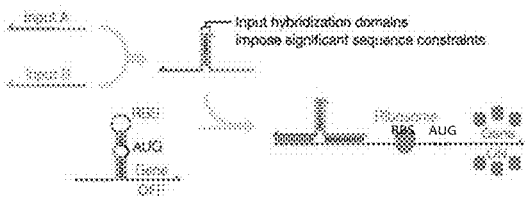
FIG. 12 illustrates limitations of previously reported toehold-switch-based logic systems. a, Toehold-mediated two-input AND logic requires hybridization between input RNAs to activate gene expression. This requirement is challenging to meet when detecting natural RNA sequences, such as those from viruses. b, Toehold-mediated three-input OR gates consist of three toehold switches assembled one after the other in the same open reading frame. This design appends extended N-terminal peptides to the output protein depending on the input species binding site. The ribosome must also translate through downstream toehold switch hairpins, which leads to substantial variations in output protein expression levels. c, Scaling of the largest reporter protein N-terminal peptide generated as a function of gate RNA architecture and number of inputs. Toehold-mediated OR gate RNAs append a peptide of up to 49% of the length of GFP for six-input logic. LIRA AND gates also generate N-terminal peptides, but peptide size scales at a much lower rate. Circles mark gate RNAs that have been demonstrated experimentally and squares are projections for gate RNAs that have yet to be demonstrated experimentally.
Figure 12:
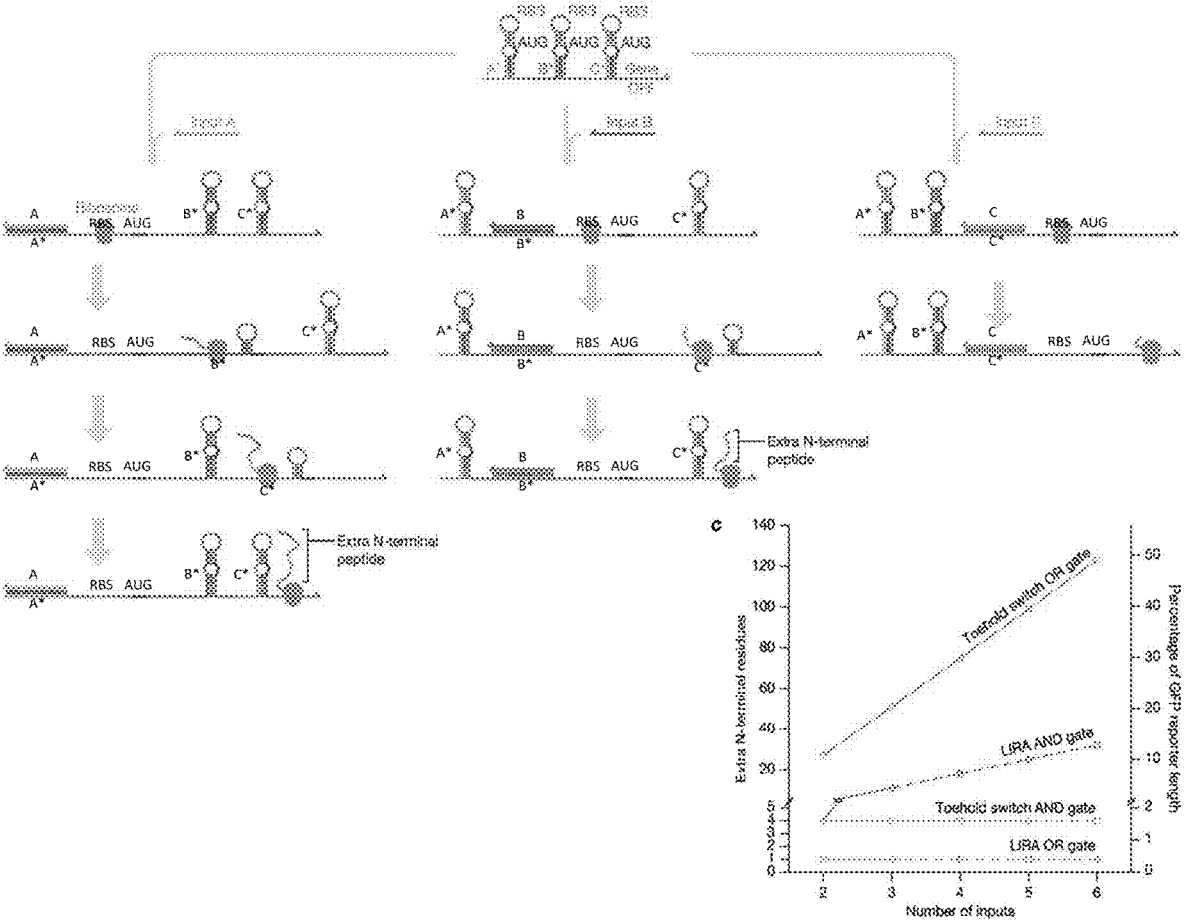

Multi-arm junctions for AND logic employ sensor arms of different strengths to implement locked and unlocked LIRA sites (FIG. 4a). The gate RNA contains a base arm topped by a weak, unlocked sensor arm for LIRA module A* and a strong, locked sensor arm for LIRA module B*. The locked arm also conceals the RBS and start codon translation initiation signals within an RNA duplex. For the logical FALSE case when only input B is expressed, the locked stem-loop structure and the base stem are designed to be too thermodynamically stable to be disrupted by input RNA B, preventing system activation. However, if input A interacts with the gate RNA first, its binding energy is sufficiently strong to disrupt both the left stem loop and the base stem of the gate RNA. Unwinding the base stem in turn unlocks the LIRA B* module, making it sufficiently weak to interact with input B. Thus, when input B is also expressed, the B* module is completely disrupted and the RBS and start codon are exposed for translation of the GFP reporter gene. Unlike the LIRA OR gates, use of locked sensor arms for LIRA AND gates does add multiple N-terminal residues to the output protein (FIG. 4a and FIG. 12c).

We tested the two-input AND device in E. coli using different combinations of input RNAs. We found that only strong GFP reporter expression was observed for the logical TRUE case with both inputs expressed. GFP expression increased by 79-fold for the TRUE case compared to the case with neither input transcribed (FIG. 4b,c). In addition, we found that translational leakage in the presence of input RNA B was low, 43-fold lower than the TRUE state, indicating that the extended stem-loop structure effectively blocked access of the transcript to the gate RNA. We also extended the AND ribocomputing strategy to three inputs using the four-arm junction structure shown in FIG. 4d. This device incorporated the binding site for input C to lock modules A* and B* and prevent them from interacting with their corresponding input RNAs without expression of input C. To increase translational output and encourage stem-loop disruption, hairpin reconfiguration domains were added to the arms for inputs A and C. This device also functioned properly in E. coli, providing a 36-fold increase in GFP expression in the logical TRUE case with all three inputs expressed compared to the null-input case (FIG. 4e,f). Leakage in all logical FALSE conditions was low with the TRUE state providing at least 16-fold higher GFP output in all cases. All of the designed sequences are listed in Table 8.

TABLE 8

| | | Sequences of multi-arm RNA junction logic systems tested in E. coli | | | |
|---|---|---|---|---|---|
| Name | Strand | Sequence | Input Order | LIRA identity | Terminator |
| 2-input OR | Gate RNA | GGGATTCATTTCACATCTCCTAATCCAGTCGTGGATGGGCTC TGTTTCCGTATTCTGTGAAGCCCTAGGGTCCGATACAGAAA CAGAGCCCATCCACGACTGGAATGGCTCTGTTTCATCTTAA AGTCCTTGTAACAGTCGTCAAGACGAAACTAAGCCATAGAG GAGATGACAAATGAATAACCTGGCGGCAGCGCAAAAG (SEQ ID NO: 73) | A, B | | N/A |
| | Input A | GGGCCAGTGACTTGTCACTGGGAACGGACCCTAGGGCTTCA CAGAATACGGAAACGAC (SEQ ID NO: 74) | N/A | LIRA1 | T7 terminator |
| | Input B | GGGCTCACCTGCCAAGGTGAGAGCGACGACTGTTACAAGG ACTTTAAGATGAAACGAC (SEQ ID NO: 75) | N/A | LIRA5 | T7 terminator |
| 3-input OR | Gate RNA | GGGATTCATTTCACATCTCCTCCTCCAGTCGTGGATGGGCTC TGTTTCCGTATTCTGTGAAGCCCTAGGGTCCGATACAGAAA CTGAGCCATTCCACATCTGGATCCAGTCGTGGATGGGCTCT GCTTAGTCGTGAAACCTATACAATCCTGTGCACGAATAAGC TGAGCCATTCCACATCTGGATAGGCTCAGTTTCATCTTAAA GTCCTTGTAACAGTCGTCAAGACGAAACCAAGCCTAAGAGG AGATGACAAATGAATAACCTGGCGGCAGCGCAAAAG (SEQ ID NO: 76) | A, C, B | | N/A |
| | Input A | GGGCCAGTGACTTGTCACTGGGAACGGACCCTAGGGCTTCA CAGAATACGGAAACGAC (SEQ ID NO: 77) | N/A | LIRA1 | T7 terminator |

TABLE 8-continued

| | | | Input | | |
| Name | Strand | Sequence | Order | LIRA identity | Terminator |
|---|---|---|---|---|---|
| | Input B | GGGCTCACCTGCCAAGGTGAGAGCGACGACTGTTACAAGG ACTTTAAGATGAAACGAC (SEQ ID NO: 78) | N/A | LIRA5 | T7 terminator |
| | Input C | GGGCACAGACGTACGTCTGTGGAAGCACAGGATTGTATAG GTTTCACGACTAAGCGAA (SEQ ID NO: 79) | N/A | LIRA19 | T7 terminator |
| 2-input AND | Gate RNA | GGGCGTGAACCAGTTTCCGTATTCTGTGAAGCCCTAGGGTC CGATACTGAAACTATCATATCTTATCTCCTGAGTTTCATCTT AAAGTCCTTGTAACAGTCGTCAAGACGAAACAGAGGAGAT AACATATGATATGGTGCACGAACCTGGCGGCAGCGCAAAA G (SEQ ID NO: 80) | A, B | | N/A |
| | Input A | GGGCCAGTGACTTGTCACTGGGAACGGACCCTAGGGCTTCA CAGAATACGGAAACGAC (SEQ ID NO: 81) | N/A | LIRA1 | T7 terminator |
| | Input B | GGGCTCACCTGCCAAGGTGAGAGCGACGACTGTTACAAGG ACTTTAAGATGAAACGAC (SEQ ID NO: 82) | N/A | LIRA5 | T7 terminator |
| 3-input AND | Gate RNA | GGGCGGGTACCTCGTTCCGTGCGGAATCTTGGAGGCTTAGT CGTGAAACCTATACAATCCTGTGCACGAATAAGCATCCAAG ATTCCGCTCGGAAAGTTGGATTCAATTCGCGAGAATAACAT CACGTTTCCGTATTCTGTGAAGCCCTAGGGTCCGATACAGA AACTTGATGGCATTCTTTCGAATCACATCAAAATCATCTCAT GTCTCCTGAGTTTCATCTTAAAGTCCTTGTAACAGTCGTCAA GACGAAACAGAGGAGACAACAGATGATTGCGATGTGTGAA TCCAACTCGAGGTACCCGAACCTGGCGGCAGCGCAAAAG (SEQ ID NO: 83) | C, A, B | | N/A |
| | Input A | GGGCCAGTGACTTGTCACTGGGAACGGACCCTAGGGCTTCA CAGAATACGGAAACGAC (SEQ ID NO: 84) | N/A | LIRA1 | T7 terminator |
| | Input B | GGGCTCACCTGCCAAGGTGAGAGCGACGACTGTTACAAGG ACTTTAAGATGAAACGAC (SEQ ID NO: 85) | N/A | LIRA5 | T7 terminator |
| | Input C | GGGCACAGACGTACGTCTGTGGAAGCACAGGATTGTATAG GTTTCACGACTAAGCGAA (SEQ ID NO: 86) | N/A | LIRA19 | T7 terminator |

Validation of LIRAs in Paper-Based Diagnostics

Figure 5:
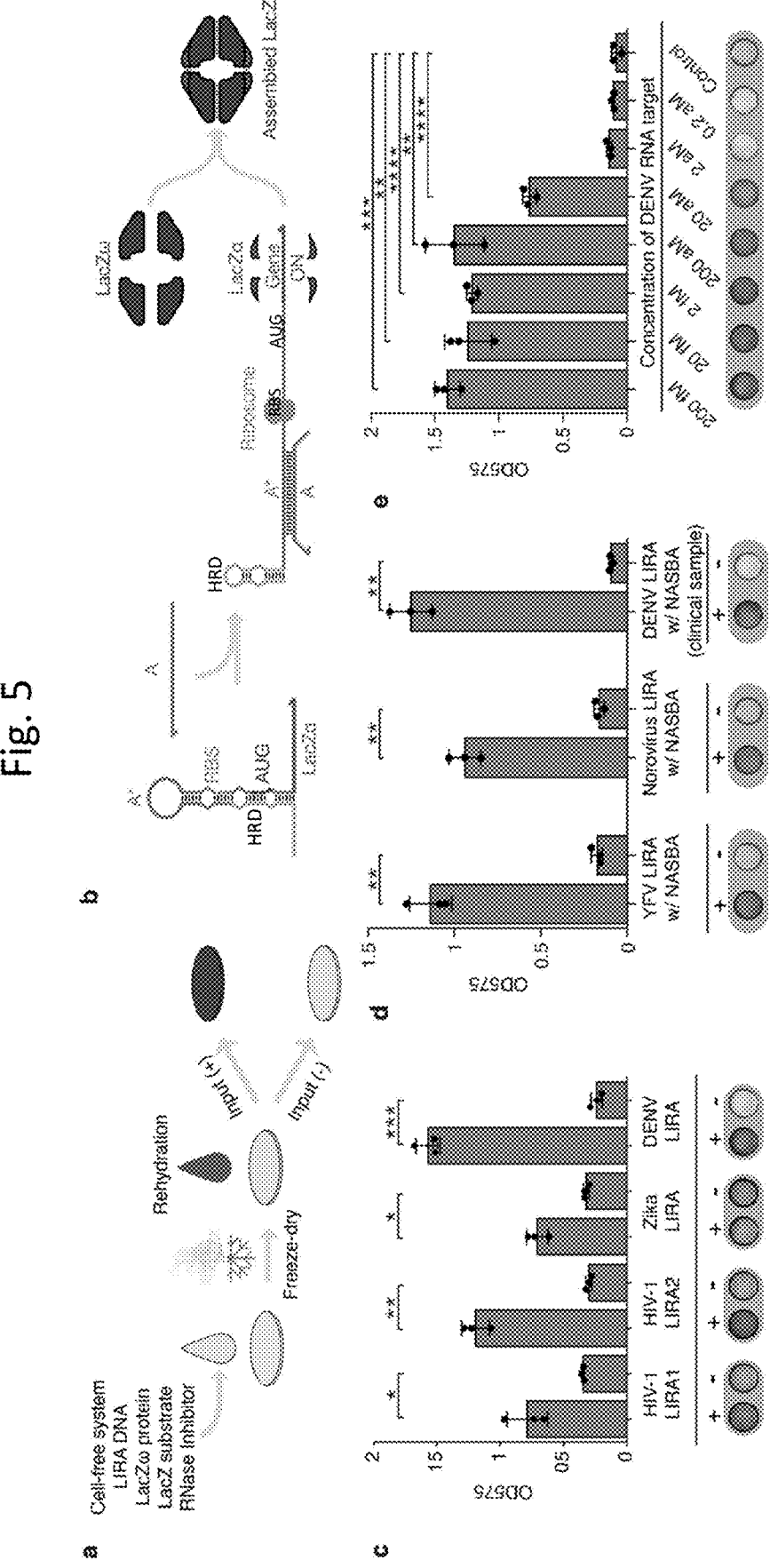
FIG. 5 depicts pathogen-detecting LIRAs in paper-based cell-free assays. a, Schematic of paper-based diagnostic assays in which cell-free transcription-translation reactions are freeze dried on paper disks to stabilize them at room temperature. Paper-based systems are reactivated by adding water with the RNA analyte of interest. b, LIRA design used for detection of viral RNAs in paper-based reactions. The optimized LIRA contains a 5' hairpin reconfiguration domain (HRD) that forms after input RNA binding to assist with activating the LIRA and increasing output gene expression. c, Detection of synthetic RNA targets for HIV, Zika virus, and dengue virus (DENV) in 80-minute paper-based reactions. The purple color change of the disks is measured by the optical density at 575 nm (OD575) and indicates that the input RNA has been detected. d, Detection of viral RNA targets at initial concentrations of 200 aM after coupling with NASBA isothermal amplification and running cell-free reactions for 80 minutes for the yellow fever virus (YFV) and 90 minutes for norovirus. Clinical serum samples positive and negative for DENV were amplified by NASBA and detected after 90 minutes in paper-based reactions containing a DENV-specific LIRA. e, Detection limit test of DENV at different starting concentrations of synthetic input RNAs demonstrating a limit of detection of 20 aM after 90-minute paper-based cell-free reactions. Two tailed student's t-test, *p<0.05, p<0.01, *p<0.001, ****p<0.0001. n=3, bars represent the arithmetic mean±SD.

The sensing and logic capabilities of LIRAs and multi-arm junction RNA nanostructures also make them promising devices for use in paper-based cell-free systems, where they can be used as diagnostics without the need for expensive equipment and provide results that can be detected by the naked eye[14-17]. Since RNA-RNA interactions differ in cell-free reactions compared to the cytoplasmic environment, we first tested LIRAs by using them as riboregulators in paper-based reactions. These reactions employed freeze-dried cell-free transcription-translation reactions along with LIRA plasmids, the lacZ ω subunit, and the lacZ colorimetric substrate chlorophenol-red-β-d-galactopyranoside (CPRG) deposited onto 2-mm diameter paper discs (FIG. 5a). At the time of use, the paper discs were rehydrated with solutions containing RNAs for detection by the embedded LIRA riboregulators. We first tested the paper-based reactions with LIRAs that showed wide dynamic range during in vivo experiments. However, in the cell-free reactions, they were unable to be turned on by their cognate input RNAs. To increase translational output and encourage stem-loop disruption, a hairpin reconfiguration domain was added to the 5' end of each LIRA sensor (FIG. 5b). Applying synthetic viral RNA targets to a final concentration of 5 μM, we found that the updated LIRA pathogen sensors provided strong increases in absorbance at 575 nm wavelength as the yellow-to-purple CPRG cleavage reaction was carried out by lacZ (FIG. 5c). Reactions with the pathogen RNAs turned to the expected pink or purple color as the reactions proceeded, while those without the pathogen RNAs remained yellow to yellow-pink in color depending on the sensor (FIG. 5c, bottom).

To enable detection of RNAs at the concentrations typically present in clinical samples, we used nucleic acid sequence-based amplification (NASBA) to amplify low-concentration pathogen RNAs prior to use in the paper-based assays. In NASBA, a combined reaction featuring reverse transcription, T7 RNA polymerase, RNase H, and DNA primers that incorporate the T7 promoter sequence are used to generate multiple RNA copies from a starting RNA template. Synthetic RNA targets from norovirus and yellow fever virus (YFV) were supplied to NASBA reactions at an initial concentration of 200 aM and amplified over 2 hours at 41° C. We found that both pathogen RNAs could be detected in the colorimetric paper-based reactions following NASBA (FIG. 5d).

In addition, we applied the assay to clinical serum samples that were positive and negative for the dengue virus. The serum samples were first diluted by 10-fold into water and heated to 95° C. for 2 minutes to release the viral genome from the capsid. The RNA was then amplified using NASBA and applied to the paper-based LIRA sensors. We found that LIRAs could unambiguously identify the clinical dengue sample through the resulting purple color. To determine the detection limit of the dengue assay, we carried out a series of NASBA/LIRA reactions with synthetic dengue target RNA concentrations ranging from 200 fM down to 0.2 aM. We found that the dengue transcript could be detected down to concentrations as low as 20 aM in the NASBA reaction, which corresponds to 12 RNA copies per μL of reaction (FIG. 5e). All of the designed sequences are listed in Table 9.

TABLE 9

| Sequences of pathogen-detecting LIRAs and NASBA primers | |
| --- | --- |
| Name | Sequence |
| HIV1_LIRA1 | GGGTAACGGATGATGTACAATCCATTATCTCCTAAGTCCT<br>CCTACTCCCTGACATGCTGTCATCATTTCTTCGTAGGAGGA<br>CAGAGGAGATAACGGATGATACATAACCTGGCGGCAGCG<br>CAAAAG (SEQ ID NO: 87) |
| HIV1_LIRA2 | GGGTAACGGATGATGTACAATCCATTATCTCCTAACTTAT<br>GGCCGGGTCCTCCTACTCCCTGACATGCTGTCCGGCCATA<br>AGAGAGGAGATAACGGATGATACATAACCTGGCGGCAGC<br>GCAAAAG (SEQ ID NO: 88) |
| Zika_LIRA | GGGTAACGGATGATGTACAATCCATTATCTCCTAAGGTGG<br>CTTCGGCTCTTGGTGAATTGGGCGTTATCTCACGAAGCCA<br>CCAGAGGAGATAACGGATGATACATAACCTGGCGGCAGC<br>GCAAAAG (SEQ ID NO: 89) |
| Norovirus_LIRA | GGGTAACGGATGATGTACAATCCATTATCTCCTAAGATGA<br>GATTCTCAGATCTGAGCACGTGGGAGGGCGATGAATCTCA<br>TCAGAGGAGATAACGGATGATACATAACCTGGCGGCAGC<br>GCAAAAG (SEQ ID NO: 90) |
| YFV_LIRA | GGGTAACGGATGATGTACAATCCATTATCTCCTAAGAAAA<br>ACCCTGGGCGTCAATATGGTACGACGAGGAGTAGGGTTTT<br>TCAGAGGAGATAACGGATGATACATAACCTGGCGGCAGC<br>GCAAAAG (SEQ ID NO: 91) |
| DENV1_LIRA | GGGTAACGGATGATGTACAATCCATTATCTCCTAAGCCAA<br>AATTCCTGCTGTTGGGGGTATGGCTAGAAATCGAATTTTG<br>GCAGAGGAGATAACGGATGATACATAACCTGGCGGCAGC<br>GCAAAAG (SEQ ID NO: 92) |

| Name | Sequence | NASBA fwd | NASBA rev |
| --- | --- | --- | --- |
| anti-<br>sense_HIV1_target1_for_HIV1_LIRA1&2 | GGGCCCCAAGGGGTTATGCTATGCTATGTCACTTCCCCTT<br>GGTTCTCTCATCTGGCCTGGTGCAATAGGCCCTGCATGCA<br>CTGGATGCACTCTATCCCATTCTGCAGCTTCCTCATTGATG<br>GTCTCTTTTAACATTTGCATGGCTGCTTGATGTCCCCCCAC<br>TCCCTATAGTGAGTCGTATTAGCGC (SEQ ID NO: 93) | | |
| anti-<br>sense_HIV1_target2_for_HIV1_LIRA3 | GGGCCCCAAGGGGTTATGCTAATTGCCTCTCTGCATCATT<br>ATGGTAGCTGAATTTGTTACTTGGCTCATTGCTTCAGCCAA<br>AACTCTTGCCTTATGGCCGGGTCCTCCTACTCCCTGACATG<br>CTGTCATCATTTCTTCTAGTGTAGCCGCTGGTCCCAATGCT<br>CCCTATAGTGAGTCGTATTAGCGC (SEQ ID NO: 94) | N/A | N/A |
| antisense_Zika_target | GGGCCTGTCCTCGGTTCACAATCAAGTCCTAGGCTTCCAA<br>ACCCCCCCAGGGTGGCTTCGGCTCTTGGTGAATTGGGCGT<br>TATCTCAACTTTCGCTCTATTCTCATCAGTTTCATGTCCTG<br>TGTCATTAACGATCATCCCACTGTGCTGGCCCTATAGTGA<br>GTCGTATTAGCGC (SEQ ID NO: 95) | N/A | N/A |
| Norovirus_target | GGGATGGATTTTTACGTGCCCAGGCAAGAGCCAATGTTCA<br>GATGGATGAGATTCTCAGATCTGAGCACGTGGGAGGGCG<br>ATCGCAATCTGGCTCCCAGTTTTGTGAATGAAGATGGCGT<br>CGAATGACGCCAACCCATCTGATGGGTCCGCAGCCAACCT<br>CGTCCCAGAGGTCAACAATGAGGTTATGGCTTTGGAGCCC<br>GT (SEQ ID NO: 96) | AATTCTAATACGAC<br>TCACTATAGGGAGA<br>AGGCTCATTGTTGA<br>CCTCTGGGA (SEQ<br>ID NO: 97) | CAGGCAA<br>GAGCCAA<br>TGTTCA<br>(SEQ ID<br>NO: 98) |
| YFV_target | GGGTGCTAATTGAGGTGCATTGGTCTGCAAATCGAGTTGC<br>TAGGCAATAAACACATTTGGATTAATTTTAATCGTTCGTT<br>GAGCGATTAGCAGAGAACTGACCAGAACATGTCTGGTCG<br>TAAAGCTCAGGGAAAAACCCTGGGCGTCAATATGGTACG<br>ACGAGGAGTTCGCTCCTTGTCAAACAAAATAAAACAAAA<br>AACAAAACAAATTGGAAACAGACCTGGACCTTCAAGAGG<br>TGTTCAAGGATTTAT (SEQ ID NO: 99) | AATTCTAATACGAC<br>TCACTATAGGGAGA<br>AGGCTTGAAGGTCC<br>AGGTCTGTTTCCA<br>(SEQ ID NO: 100) | GAGCGAT<br>TAGCAGA<br>GAACTGA<br>CCA (SEQ<br>ID NO:<br>101) |
| DENV1_target | GGGATTGCTTTCAGGCCAAGGACCCATGAAATTGGTGATG<br>GCTTTCATAGCATTTCTAAGATTTCTAGCCATACCCCCAAC<br>AGCAGGAATTTTGGCTAGATGGAGCTCATTCAAGAAGAAT<br>GGAGCGATCAAAGTGTTACGGGGTTTC (SEQ ID NO:<br>102) | AATTCTAATACGAC<br>TCACTATAGGGAGA<br>AGGCCAAGGACCCA<br>TGAAATTGGTGA<br>(SEQ ID NO: 103) | CCGTAAC<br>ACTTTGAT<br>CGCTCCA<br>(SEQ ID<br>NO: 104) |

Paper-Based Diagnostic with Embedded Molecular Logic

Diagnostic devices that combine visible readouts with the ability to perform information processing on biomolecular inputs have the potential to improve assay capabilities by expanding the number of pathogens a single test can detect, reducing false positives, and lowering assay complexity and cost. To demonstrate the potential of such logic-enabled paper-based diagnostic devices, we carried out proof-of-concept studies exploiting the logic capabilities of multi-arm junction molecular logic for HIV and SARS-CoV-2 detection. All of the designed sequences are listed in Table 10. HIV continues to be a major global health threat with HIV-1 group M being the predominant cause of infections worldwide[42,43]. Within group M, there are nine different subtypes with genetic distances of 25% to 35% and prevalences that vary depending on the geographic region. HIV-1 subtype C causes >50% of infections worldwide and circulates mostly in India and regions of Africa, while HIV-1 subtype B predominates in Europe and the Americas[44]. We thus aimed to develop a logic system capable of detecting both HIV-1 subtype B and C using a single OR operation, which could be deployed in an area such as Southern Brazil where both subtypes are common[45].

TABLE 10

| Sequences of virus-detecting multi-arm RNA junction logic systems and NASBA primers | | | |
|---|---|---|---|
| Name | Sequence | | |
| HIV1_2-input_Or_sensor | GGGATTCATTTCACATCTGCTCTATAGCCTGTACCGTCAGCGTT ATTGACGCCGCGCCCATAGTGCTTCCTGTCACTAACGAGGACG GGCCAGGCGTTCTGCGATTCTTCAATTAAGGTGTATATTTCTCT TGTGTAATTACCTCAATTGATGAATCAAAGAACAATAGAGGAG ATGACAAATGAATAACCTGGCGGCAGCGCAAAAG (SEQ ID NO: 105) | | |
| SARS2_N1*N2* | GGGACTCAAATCTTCGCTACAGCGACATCTACACATTACGTTT GGTGGACCCTCAGATTCAACTAAACCTAATGGGTAGAACTCGC TAAAGCGATGTCTACCTGCCATATCTTATCTCCTGAACTGATTA CAAACATTGGCCGCAAATTGTGTATTCAGTAGAGGAGATACAA TATGGCAATTAGACAAGATACGAGTAACCTGGCGGCAGCGCA AAAG (SEQ ID NO: 1) | | |
| SARS2_N2*N1 | GGGACTCAAATCTTCGCTACAGCGACATCTACAGGAACTGATT ACAAACATTGGCCGCAAATTGAATCTGTTCCGGTAGAACTCGC TAAAGCGATGTCTACCTGCCATATCTTATCTCCTGACTGCGTTC TCCATTCTGGTTACTGCCAGGAGAACGCAGAGAGGAGATACAA TATGGCAATTAGACAAGATACGAGTAACCTGGCGGCAGCGCA AAAG (SEQ ID NO: 2) | | |
| Name | Sequence | NASBA fwd | NASBA rev |
| HIV1_subB_sense_target | GGGCACCACTGCTGTGCCTTGGAATGCTAGTTGGAGTAATAAA TCTCTGAATGAGATTTGGGATAACATGACTTGGATGGAGTGGG AAAGAGAAATTGACAATTACACAAGAGAAATATACACCTTAAT TGAAGAATCGCAGAACCAACAAGAAAAGAATGAACTAGACTT ATTGGAATTGGATAAGTGGGCAAGTTTGTGG (SEQ ID NO: 106) | AATTCTAATACGACT CACTATAGGGCCTTG GAATGCTAGTTGGAG TAATA (SEQ ID NO: 107) | GTTGGTTCTGC GATTCTTCAAT TA (SEQ ID NO: 108) |
| HIV1_subC_sense_target | GGGAGTAGCACCCACTGAGGCAAAAAGGAGAGTGGTGGAGAG AGAAAAAAGAGCAGTGGGAATAGGAGCTGTGCTCCTTGGGTTC TTGGGAGCAGCAGGAAGCACTATGGGCGCGGCGTCAATAACG CTGACGGTACAGGCCAGACAACTGTTGTCTGGTATAGTGCAAC AGCAAAGCAATTTGCTGAGGGCTATAGAGGCGCAACAGC (SEQ ID NO: 109) | AATTCTAATACGACT CACTATAGGGAAAGA GCAGTGGGAATAGGA (SEQ ID NO: 110) | GCAAATTGCTT TGCTGTTGCAC TA (SEQ ID NO: 111) |
| SARS2_sense_N1 | GGGTTCGTGTTGTTTTAGATTTCATCTAAACGAACAAACTAAA ATGTCTGATAATGGACCCCAAAATCAGCGAAATGCACCCCGCA TTACGTTTGGTGGACCCTCAGATTCAACTGGCAGTAACCAGAA TGGAGAACGCAGTGGGGCGCGATCAAAACAACGTCGGCCCCA AGGTTTACCCA (SEQ ID NO: 112) | AATTCTAATACGACT CACTATAGGGAGAAG GACGTTCGTGTTGTTT TAGA (SEQ ID NO: 113) | TTATTGGGTAA ACCTTGGGGCC GA (SEQ ID NO: 114) |
| SARS2_antisense_N1 | GGGTGGGTAAACCTTGGGGCCGACGTTGTTTTGATCGCGCCCC ACTGCGTTCTCCATTCTGGTTACTGCCAGTTGAATCTGAGGGTC CACCAAACGTAATGCGGGGTGCATTTCGCTGATTTTGGGGTCC ATTATCAGACATTTTAGTTTGTTCGTTTAGATGAAATCTAAAAC AACACGAA (SEQ ID NO: 115) | AATTCTAATACGACT CACTATAGGGAGAAG GATGTTGAGTGAGAG CGGTGAACCA (SEQ ID NO: 116) | GACCCCAAAT CAGCGAAATG CA (SEQ ID NO: 117) |
| SARS2_antisense_N2 | GGGCACCTGTGTAGGTCAACCACGTTCCCGAAGGTGTGACTTC CATGCCAATGCGCGACATTCCGAAGAACGCTGAAGCGCTGGGG GCAAATTGTGCAATTTGCGGCCAATGTTTGTAATCAGTTCCTTG TCTGATTAGTTCCTGGTCCCCAAAATTTCCTTGGGTTTGTTCTG GACCACGTC (SEQ ID NO: 118) | AATTCTAATACGACT CACTATAGGGAGAAG GTTTGATGGCACCTG TGTAGGTCA (SEQ ID NO: 119) | AAGCTTTCGGC AGACGTGGTCC A (SEQ ID NO: 120) |

Figure 6:
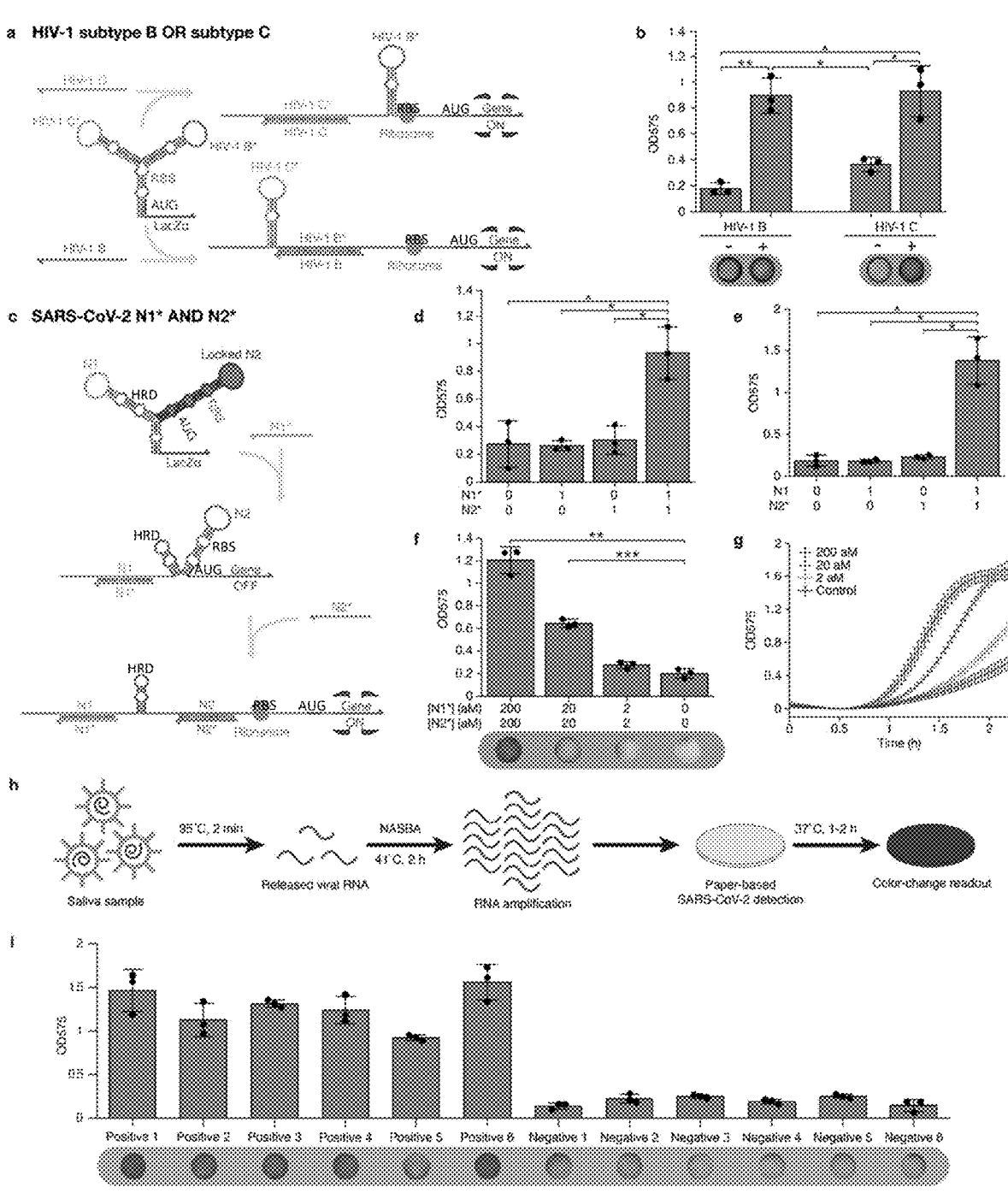
FIG. 6 depicts logic-enabled paper-based assays using multi-arm junction gate RNAs for identification of HIV-1 group M subtypes and SARS-CoV-2. a, Schematic of the three-arm junction gate RNA used for simultaneous detection of B and C HIV-1 subtypes via two-input OR logic. b, Detection of HIV-1 B and HIV-1 C subtypes in paper-based reactions. Photographs are taken after 90 minutes of the cell-free reaction. c, Schematic of the three-arm junction gate RNA used for SARS-CoV-2 detection via two-input AND logic. d, OD575 for an AND gate RNA N1*N2* detecting synthetic input fragments N1* and N2* from the SARS-CoV-2 genome. e, OD575 for an AND gate RNA N2*N1 detecting synthetic input fragments N2* and N1 from the SARS-CoV-2 genome. f, Validation of AND gate RNA N1*N2* with heat-inactivated SARS-CoV-2 virions amplified via isothermal NASBA reactions. Inactivated viruses were diluted with water. Photos were taken after 90-minute reactions. g, Time-course curves for the reactions tested in panel f. h, Schematic of the process for measuring clinical saliva samples starting from heat-driven RNA extraction through to the colorimetric paper-based cell-free assay. i, AND gate RNA N2*N1 tested with SARS-CoV-2 positive and negative saliva samples with NASBA products after 2-hour reactions, p values between each pair of positive and negative samples are all less than 0.05. Two tailed student's T test, *p<0.05, p<0.01, *p<0.001, ****p<0.0001. n=3, curves represent arithmetic mean±SD.

To create this system, we first identified conserved regions in the genomes of HIV-1 subtypes B and C to use as circuit input RNAs. Complementary sequences for these inputs were then incorporated into a two-input OR three-arm junction gate RNA (FIG. 6a). To ensure the system functioned properly in paper-based cell-free reactions, the binding site for the input RNAs was extended so that it included both the loop domain and the entire stem of the LIRA module. The gate RNA was transcribed in the cell-free reactions and supplied with the HIV-1 subtypes B and C input RNAs. For both inputs, output of the lacZ a subunit was produced, as evidenced by increased production of the purple cleavage product in the paper-based reactions (FIG. 6b). Reactions lacking either input RNA remained yellow.

We next made use of AND logic operations to implement RNA devices for severe acute respiratory syndrome coronavirus 2 (SARS-CoV-2) detection. SARS-CoV-2 was first reported in 2019 in Wuhan, China, has now become a global pandemic with over 100 million reported cases and over 3 million deaths worldwide according to data from the Johns Hopkins Coronavirus Resource Center. SARS-CoV-2 can be transmissible even before any symptoms have developed[46, 47] and studies have shown that many patients who test positive for the virus do not show any symptoms[48]. These factors have allowed the pandemic to take hold and emphasize the importance of developing diagnostic assays that can be widely deployed to detect SARS-CoV-2, even in carriers who do not have any signs of illness.

Following the US Centers for Disease Control and Prevention (CDC) recommendations[49], SARS-CoV-2 infections are often identified by amplification of two selected regions of the virus nucleocapsid (N) gene, 2019-nCoV_N1 and 2019-nCoV_N2. RT-qPCR is the most common method of detection of SARS-CoV-2 given its excellent specificity and sensitivity. However, it requires well-trained personnel and expensive equipment, which makes virus detection more challenging in rural areas with limited medical resources and requires additional time to ship samples to centralized facilities. Previous paper-based cell-free assays have been limited to detecting only a single pathogen target sequence at a time, and parallel assays that detect target RNAs in separate reactions can suffer as a result of differences in riboregulator activation speeds and lead to increased assay cost.

To overcome these issues, we combined AND logic multi-arm junctions with isothermal amplification reactions to simultaneously detect two different SARS-CoV-2 N gene sequences using a single paper-based readout reaction. The resulting two-input AND gate RNAs contained a hairpin reconfiguration domain to encourage binding between the gate RNA and the input viral RNAs (FIG. 6c). The sequences of these RNAs are provided in Table 11. We first evaluated several devices using synthetic targets and identified two with the best performance. Gate RNA N1*N2* recognizes the antisense sequences in regions N1 and N2 of the SARS-CoV-2 N gene, with left and right sensor arms targeting N1* and N2*, respectively (FIG. 6d). Similarly, gate N2*N1 targets the antisense sequence of the N2 region with the left sensor arm and the sense sequence of the N1 region with the right sensor arm (FIG. 6e). Both devices show clear color changes in the presence of the two input RNAs, but did not activate when one or both inputs were absent, successfully carrying out AND logic (FIG. 6d,e). The other tested sequences either exhibited high signal leakage or took a much longer time to provide color change readout.

TABLE 11

Sequences of the two-input AND gate RNAs for detection of SARS-COV-2

| Riboregulator | Sequence |
|---|---|
| SARS2_N1*N2 | GGGACTCAAATCTTCGCTACAGCGACATCTACACATTACGTTTG GTGGACCCTCAGATTCAACTAAACCTAATGGGTAGAACTCGCTA AAGCGATGTCTACCTGCCATATCTTATCTCCTGAATCAGTTCCTT GTCTGATTAGTTCCTGGAGGAACTGATAGAGGAGATACAATATG GCAATTAGACAAGATACGAGTAACCTGGCGGCAGCGCAAAAGA TGCGTAAAGGAGAAGAACTTTTCACTGG (SEQ ID NO: 193) |
| aN2N1_A SARS2_N2*N1 | GGGACTCAAATCTTCGCTACAGCGACATCTACAGGAACTGATTA CAAACATTGGCCGCAAATTGAATCTGTTCCGGTAGAACTCGCTA AAGCGATGTCTACCTGCCATATCTTATCTCCTGACTGCGTTCTCC ATTCTGGTTACTGCCAGGAGAACGCAGAGAGGAGATACAATAT GGCAATTAGACAAGATACGAGTAACCTGGCGGCAGCGCAAAAG ATGCGTAAAGGAGAAGAACTTTTCACTGG (SEQ ID NO: 194) |
| SARS2_N1N2* | GGGACTCAAATCTTCGCTACAGCGACATCTACACTGCGTTCTCC ATTCTGGTTACTGCCAGTTGGAGACCGCAGGGTAGAACTCGCTA AAGCGATGTCTACCTGCCATATCTTATCTCCTGAACTGATTACAA ACATTGGCCGCAAATTGTGTATTCAGTAGAGGAGATACAATATG GCAATTAGACAAGATACGAGTAACCTGGCGGCAGCGCAAAAGA TGCGTAAAGGAGAAGAACTTTTCACTGG (SEQ ID NO: 195) |
| SARS2_N1N2 | GGGACTCAAATCTTCGCTACAGCGACATCTACACTGCGTTCTCC ATTCTGGTTACTGCCAGTTGGAGACCGCAGGGTAGAACTCGCTA AAGCGATGTCTACCTGCCATATCTTATCTCCTGAAATTTGCGGCC AATGTTTGTAATCAGTTGCCGCAAATTAGAGGAGATACAATATG GCAATTAGACAAGATACGAGTAACCTGGCGGCAGCGCAAAAGA TGCGTAAAGGAGAAGAACTTTTCACTGG (SEQ ID NO: 196) |
| SARS2_N1*N2* | GGGACTCAAATCTTCGCTACAGCGACATCTACACATTACGTTTG GTGGACCCTCAGATTCAACTAAACCTAATGGGTAGAACTCGCTA AAGCGATGTCTACCTGCCATATCTTATCTCCTGAACTGATTACAA ACATTGGCCGCAAATTGTGTATTCAGTAGAGGAGATACAATATG GCAATTAGACAAGATACGAGTAACCTGGCGGCAGCGCAAAAGA TGCGTAAAGGAGAAGAACTTTTCACTGG (SEQ ID NO: 197) |

TABLE 11-continued

Sequences of the two-input AND gate RNAs for detection of SARS-COV-2

| Riboregulator | Sequence |
|---|---|
| SARS2_N2N1* | GGGACTCAAATCTTCGCTACAGCGACATCTACACGGCCAATGTT TGTAATCAGTTCCTTGTCTGACATCGGCCGGGTAGAACTCGCTA AAGCGATGTCTACCTGCCATATCTTATCTCCTGATTAGATTTCAT CTAAACGAACAAACTAATGAAATCTAAAGAGGAGATACAATAT GGCAATTAGACAAGATACGAGTAACCTGGCGGCAGCGCAAAAG ATGCGTAAAGGAGAAGAACTTTTCACTGG (SEQ ID NO: 198) |
| SARS2_N2N1 | GGGACTCAAATCTTCGCTACAGCGACATCTACACGGCCAATGTT TGTAATCAGTTCCTTGTCTGACATGGGCCGGGTAGAACTCGCTA AAGCGATGTCTACCTGCCATATCTTATCTCCTGAGCGTTCTCCAT TCTGGTTACTGCCAGTTTGGAGAACGCAGAGGAGATACAATATG GCAATTAGACAAGATACGAGTAACCTGGCGGCAGCGCAAAAGA TGCGTAAAGGAGAAGAACTTTTCACTGG (SEQ ID NO: 199) |
| SARS2_N2*N1* | GGGACTCAAATCTTCGCTACAGCGACATCTACAGGAACTGATTA CAAACATTGGCCGCAAATTGAATCTGTTCCGGTAGAACTCGCTA AAGCGATGTCTACCTGCCATATCTTATCTCCTGATTAGATTTCAT CTAAACGAACAAACTAATGAAATCTAAAGAGGAGATACAATAT GGCAATTAGACAAGATACGAGTAACCTGGCGGCAGCGCAAAAG ATGCGTAAAGGAGAAGAACTTTTCACTGG (SEQ ID NO: 200) |

*The riboregulators in bold produced the best results.

Figure 10:
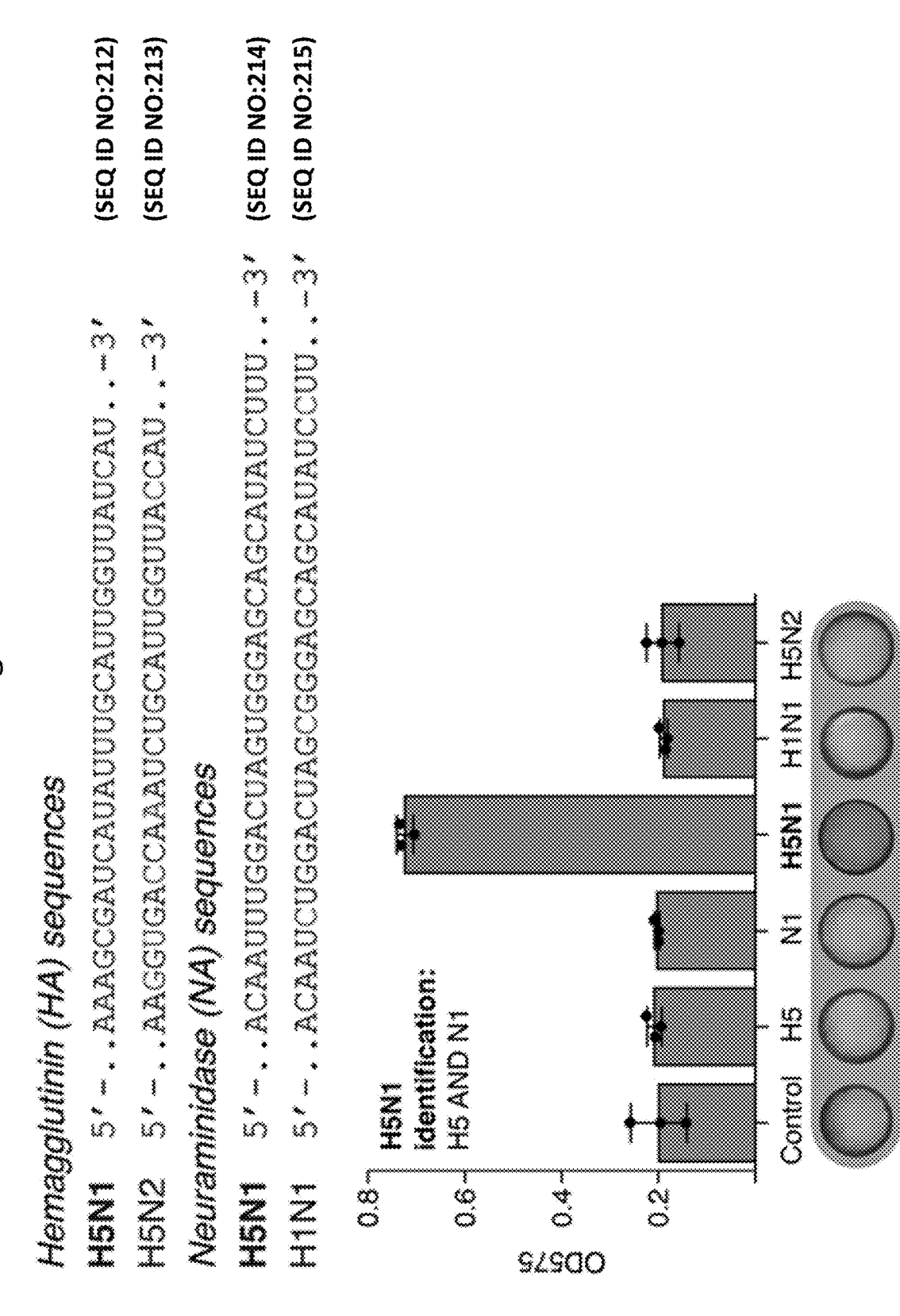
FIG. 10 shows testing of multi-arm junction gate RNAs for identification of influenza A subtypes. a, Sequences of H5N1 and related subtypes. b, Differentiation of H5N1 from related subtypes in 2-hour paper-based reactions. c, Sequences of H1N1 and related subtypes. d, Differentiation of H1N1 from related subtypes in 2-hour paper-based reactions. e, Sequences of H1N2 and related subtypes. f, Differentiation of H1N2 from related subtypes in 80-minute paper-based reactions.
Figure 10:
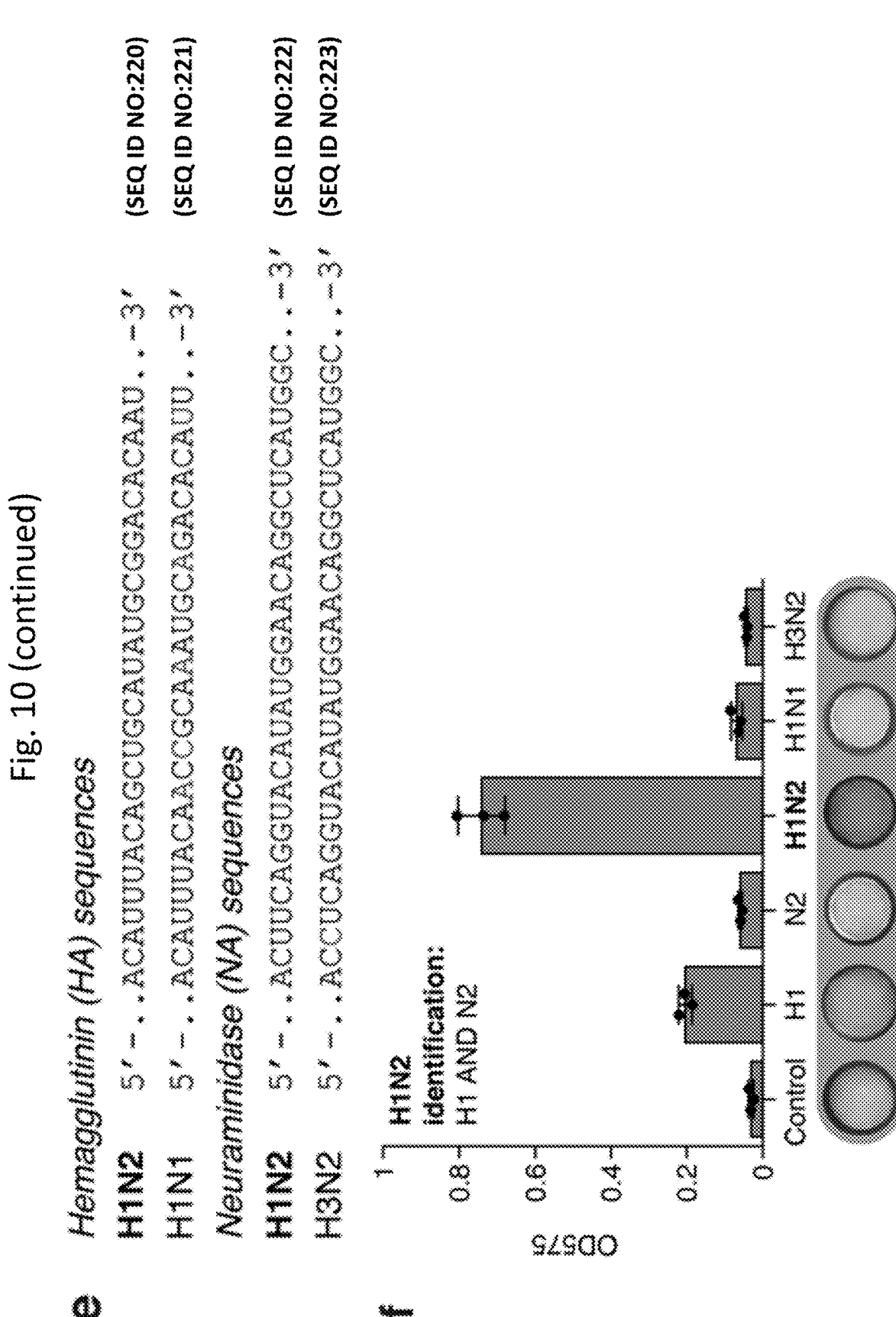

We then designed specific NASBA primer pairs for each of the two devices to amplify the input RNAs from the SARS-CoV-2 genome. NASBA reactions were performed using heat-inactivated SARS-CoV-2 virus particles at a range of different concentrations. We found that gate N1*N2* performed better than gate N2*N1 and enabled detection of SARS-CoV-2 down to concentrations of 20 aM in the NASBA reactions when viewed by the naked eye (FIG. 6g), a concentration that is within the range necessary for detecting the virus in clinical samples[50]. Using a plate reader, we could distinguish SARS-CoV-2 in the NASBA reaction down to a concentration of 2 aM. We then tested six positive saliva samples from SARS-CoV-2 patients together with six negative ones. FIG. 6h illustrates the process from sample treatment to paper-based reactions. Diluted saliva samples were subjected to a brief 95° C. heating step for 2 minutes to release the viral RNA and then added to NASBA reactions for amplification of each input RNA. The resulting amplicons were then applied to paper-based cell-free reactions for testing with the SARS-CoV-2 AND gate N2*N1 RNA. As shown in FIG. 6i, the gate RNA successfully detected the six positive samples generating a clearly visible purple color, while the six negative samples remained yellow in color. A similar strategy was also applied to differentiate different influenza A subtypes and distinguished H1N1, H5N1, and H1N2 from closely related virus subtypes (FIG. 10; tested sequences are listed in Table 12).

TABLE 12

| | Sequences of multi-arm RNA junction logic systems for influenza subtyping | | |
|---|---|
| Name | Sequence |
| N2H1_1 | GGGACTCAAATCTTCGCTACAGCGACATCTACAGCCATGAGCCTGTTC CATATGTACCTGAAGTGGCTGATGGCGGTAGAACTCGCTAAAGCGAT GTCTACCTGCCATATCTTATCTCCTGATTGTGTCCGCATATGCAGCTGT AAATGTGCGGACACAAAGAGGAGATACAATATGGCAATTAGACAAG ATACGAGTAACCTGGCGGCAGCGCAAAAG (SEQ ID NO: 201) |
| N1H5_1 | GGGACTCAAATCTTCGCTACAGCGACATCTACAAAGATATGCTGCTCC CACTAGTCCAAATTGTAGCAAATCTTGGTAGAACTCGCTAAAGCGAT GTCTACCTGCCATATCTTATCTCCTGAATGATAACCAATGCAAATATG ATCGCTTTGGTCATCATAGAGGAGATACAATATGGCAATTAGACAAG ATACGAGTAACCTGGCGGCAGCGCAAAAG (SEQ ID NO: 202) |
| N1H1_L15 | GGGACTCAAATCTTCGCTACAGCGACATCTACAGCTCCCGCTAGTCCA GATTGTGTTCTCTTCGTAGCTGGAGCGGTAGAACTCGCTAAAGCGATG TCTACCTGCCATATCTTATCTCCTGACAGTGTCTGTTGAATTGTTCGCA TGACAGACACTGAGAGGAGATACAATATGGCAATTAGACAAGATACG AGTAACCTGGCGGCAGCGCAAAAG (SEQ ID NO: 203) |
| H1N1_H | GGGTACATTTACAACCGCAAATGCAGACACATTATGTATAGGTTATC ATGCGAACAATTCAACAGACACTGTAGACACAGTACTAGAAAAGAAT GTAACAGTAACACACTCTGTTAATCTTCT (SEQ ID NO: 204) |
| H1N2_H | GGGTACATTTACAGCTGCATATGCGGACACAATATGTATAGGATACC ATGCCAACAACTCAACCGACACTGTTGACACAGTACTTGAAAAGAAT GTGACAGTGACCCACTCTGTCAACCTACT (SEQ ID NO: 205) |

TABLE 12-continued

Sequences of multi-arm RNA junction
logic systems for influenza subtyping

| Name | Sequence |
|------|----------|
| H3N2_H | GGGTCTATGTCTGGTTTTCGCTCAAAAAATTCCTGGAAATGACAATAG CACGGCAACGCTGTGCCTTGGGCACCATGCAGTACCAAACGGAACGA TAGTGAAAACAATCACAAATGACCGAAT (SEQ ID NO: 206) |
| H5N1_H | GGGAATCAGCCTTGTCAAAAGCGATCATATTTGCATTGGTTATCATGC AAATAACTCGACAGAGCAGGTTGACACAATAATGGAAAAGAACGTTA CTGTTACACATGCCCAAGACATACTGGA (SEQ ID NO: 207) |
| H1N1_N | GGGAGTTTTGTTCAGCATCCAGAACTAACAGGGCTGGATTGTATAAG ACCTTGCTTCTGGGTTGAACTAATAAGAGGACGACCCGAAGAGAACA CAATCTGGACTAGCGGGAGCAGCATATCCTTTTGTGGTGTAGACAGT GACACTGTGGGTTGGTCTTGGCCAGACGGTGCTGAGTTGCCATTTACC ATTGACAAGTAA (SEQ ID NO: 208) |
| H1N2_N | GGGTCCGGTTATTCTGGCATTTTCTCTGTCGAAGGCAAAAACTGCATC AATCGGTGCTTTTATGTGGAGTTGATAAGGGGAAGGAAACAGGAAAC TGAAGTCGGGTGGACCTCAAACAGTATTGTTGTGTTTTGTGGGACTTC AGGTACATATGGAACAGGCTCATGGCCTGATGGGGCAGACATCAATC TCATGCCTATATAA (SEQ ID NO: 209) |
| H3N2_N | GGGTCCGGTTATTCTGGTATTTTCTCTGTTGAAGGCAAAAGCTGCATC AATCGGTGCTTTTATGTGGAGTTGATTAGGGGAAGAAAAGAGGAAAC TGAAGTCTTGTGGACCTCAAACAGTATTGTTGTGTTTTGTGGCACCTC AGGTACATATGGAACAGGCTCATGGCCTGATGGGGCGGACCTCAATC TCATGCATATATAA (SEQ ID NO: 210) |
| H5N1_N | GGGAGTTTTGTCCAGCACCCAGAACTGACAGGATTAGATTGCATGAG ACCTTGCTTCTGGGTTGAGTTAATCAGAGGGCGGCCCAAAGAGAGCA CAATTTGGACTAGTGGGAGCAGCATATCTTTTTGTGGTGTAAATAGTG ACACTGTGAGCTGGTCTTGGCCAGACGGTGCTGAGTTGCCATTCACCA TTGACAAGTAGC (SEQ ID NO: 211) |

Discussion:

We have implemented a strategy for encoding molecular logic operations in multi-arm RNA junctions for regulation at the translational level. These systems make use of loop-initiated RNA-RNA interactions via LIRA modules to detect input RNAs and direct the programmed unfolding of the multi-arm RNA nanostructures to report on computation results. We have found that LIRAs on their own can operate as riboregulators with wide dynamic ranges, good orthogonality, and low translational leakage using such loop interactions. Moreover, they completely decouple the sequence of their cognate input RNA from the sequence of the output module that they expose, which avoids some of the limitations of toehold-based riboregulators. By incorporating LIRA modules into the multi-arm junction nanostructures, we implemented three-input OR and three-input AND operations in living E. coli cells. We also applied these systems in paper-based cell-free assays for detection of viruses, including the dengue virus and SARS-CoV-2 from clinical samples. Using multi-arm junctions in paper-based reactions, we produced colorimetric assays that harness OR logic to activate in response to two different subtypes of HIV-1 and AND logic to target two regions of nucleocapsid gene of SARS-CoV-2 at the same time. Application of the system to a set of positive and negative saliva samples demonstrated accurate identification of SARS-CoV-2 using a two-input multi-arm junction gate RNA.

Our results show that loop-initiated interactions can be very effective at driving RNA-RNA interactions in vivo and in paper-based cell-free reactions. However, effective interactions require loop domains that are sufficiently long (≥15 nt, see FIG. 7) to provide effective binding sites and sufficient binding free energy to promote capture of the input RNA. Invasion of the input RNA into the regulator stem region further promotes the interaction and helps drive apart the remaining base pairs in the stem. In comparison with ribocomputing devices based on toehold switches, our results indicate that LIRA-based molecular logic systems generally provide lower ON/OFF ratios, probably because loop-initiated interactions are not quite as effective as toehold-initiated ones. Despite this disadvantage, we do find that LIRA-based systems offer several key benefits over toehold-switch-based circuitry[11]. The use of multi-arm junctions for LIRA OR gate RNAs does not require translation through downstream hairpin structures and alleviates the need for long N-terminal peptides to be added to the output protein. These design features for toehold-mediated OR gates result in N-terminal peptides that increase in size by about 24 residues for each additional input detected (FIG. 12c). This condition has led to the fusion of N-terminal peptides up to 123 residues long to the reporter protein[11], which corresponds to nearly half the length of GFP. Moreover, these OR gates can exhibit substantial variations in output protein expression as a function of the input RNA, yielding as much as a 14-fold difference in signal depending on the input used[11]. For the LIRA-based OR gates reported herein, the peak variation in output expression observed is 3.2-fold (FIG. 3e). Since loop-initiated OR gate performance is dominated by effects at the RNA level, as opposed to less predictable factors such as ribosome processivity and N-terminal peptide folding and translation efficiency, we expect that future refinements in LIRA OR gate secondary structure and computational design will enable higher ON/OFF ratios to be achieved. For LIRA-based AND gates, the use of loop-initiated interactions allows sets of completely unrelated input RNA sequences to be monitored, facilitating accurate detection of two SARS-CoV-2 targets in a single paper-based colorimetric reaction. Direct detection of two pathogen targets is not possible using previously reported cell-free toehold-switch assays as a result of input sequence complementarity requirements. Detection of two genomic sites simultaneously can also offer advantages compared with recently reported riboregulators with single-nucleotide specificity when targeting pathogens that are known to be mutating rapidly[17]. The multi-arm junction AND gate design does require some N-terminal residues to be added to the output protein. However, the length of the additional peptide is much smaller than that used for toe-hold-mediated OR gate RNAs. This peptide length increases at an expected rate of only about seven residues for each additional input (FIG. 12c). Given the strengths and weaknesses of toehold- and loop-initiated interactions, we expect that future ribocomputing systems can make use of both of these strategies in the same gate RNA to achieve optimal performance by maximizing dynamic range, reducing expression variability, and avoiding input sequence constraints.

CRISPR-based molecular diagnostics[56-58] have also been applied for rapid detection of SARS-CoV-2[59,60]. These assays have demonstrated limits of detection of ~10 copies per µl in the sample[59] compared with the 60 copies per µl (or 20 aM in the amplification reaction) reported in this work for visible detection. CRISPR-based visible readout reactions have relied on lateral flow strips and targeted a single viral site in each reaction[59,60]. Our strategy provides a simplified procedure by monitoring two SARS-CoV-2 amplicons in the same reaction. Since the paper-based riboregulator assays can be run in array formats[14] and monitored directly using cameras without added light sources or filters, readout via colorimetric cell-free reactions could also enable parallel testing of larger numbers of samples than CRISPR-based assays.

We expect that the in vivo-validated loop-initiated motifs described here, which eliminate any correlation between the input and output sequence, will prove broadly useful for implementing a variety of other forms of RNA-based regulation, particularly those that can require strict sequence constraints, such as conditional guide RNAs[51-55] and aptamer-based probes[18]. Moreover, the strategy for encoding molecular logic using multi-arm junction nanostructures can also be applied to a variety of different forms of RNA output and provide the capacity to respond to multiple input species without sequence constraints. We anticipate that these capabilities will prove valuable for constructing intracellular systems that respond to endogenous RNAs to report and control cell state for biological circuits. In addition, they can be deployed in diagnostic assays to increase specificity and sensitivity, while reducing cost and test complexity to help respond to infectious disease outbreaks.

REFERENCES

1. O. H. Tam, A. A. Aravin, P. Stein, A. Girard, E. P. Murchison, S. Cheloufi, E. Hodges, M. Anger, R. Sachidanandam, R. M. Schultz & G. J. Hannon, "Pseudogene-derived small interfering RNAs regulate gene expression in mouse oocytes," *Nature* 453, 534-538 (2008).
2. E. A. Doherty & J. A. Doudna, "Ribozyme structures and mechanisms," *Annu Rev Biophys Biomol Struct* 30, 457-475 (2001).
3. A. Serganov & E. Nudler, "A decade of riboswitches," *Cell* 152, 17-24 (2013).
4. J. G. Zalatan, M. E. Lee, R. Almeida, L. A. Gilbert, E. H. Whitehead, M. La Russa, J. C. Tsai, J. S. Weissman, J. E. Dueber, L. S. Qi & W. A. Lim, "Engineering complex synthetic transcriptional programs with CRISPR RNA scaffolds," *Cell* 160, 339-350 (2015).
5. M. C. Tsai, O. Manor, Y Wan, N. Mosammaparast, J. K. Wang, F. Lan, Y Shi, E. Segal & H. Y Chang, "Long noncoding RNA as modular scaffold of histone modification complexes," *Science* 329, 689-693 (2010).
6. F. J. Isaacs, D. J. Dwyer, C. Ding, D. D. Pervouchine, C. R. Cantor & J. J. Collins, "Engineered riboregulators enable post-transcriptional control of gene expression," *Nat Biotechnol* 22, 841-847 (2004).
7. A. A. Green, P. A. Silver, J. J. Collins & P. Yin, "Toehold switches: de-novo-designed regulators of gene expression," *Cell* 159, 925-939 (2014).
8. A. Wittmann & B. Suess, "Engineered riboswitches: Expanding researchers' toolbox with synthetic RNA regulators," *FEBS Letters* 586, 2076-2083 (2012).
9. B. M. Lunde, C. Moore & G. Varani, "RNA-binding proteins: modular design for efficient function," *Nat Rev Mol Cell Biol* 8, 479-490 (2007).
10. L. M. Hochrein, M. Schwarzkopf, M. Shahgholi, P. Yin & N. A. Pierce, "Conditional Dicer substrate formation via shape and sequence transduction with small conditional RNAs," *J Am Chem Soc* 135, 17322-17330 (2013).
11. A. A. Green, J. Kim, D. Ma, P. A. Silver, J. J. Collins & P. Yin, "Complex cellular logic computation using ribocomputing devices," *Nature* 548, 117-121 (2017).
12. B. Groves, Y-J. Chen, C. Zurla, S. Pochekailov, J. L. Kirschman, P. J. Santangelo & G. Seelig, "Computing in mammalian cells with nucleic acid strand exchange," *Nature Nanotechnology* 11, 287-294 (2016).
13. G. Chatterjee, Y-J. Chen & G. Seelig, "Nucleic Acid Strand Displacement with Synthetic mRNA Inputs in Living Mammalian Cells," *ACS Synthetic Biology* 7, 2737-2741 (2018).
14. K. Pardee, A. A. Green, T. Ferrante, D. E. Cameron, A. DaleyKeyser, P. Yin & J. J. Collins, "Paper-based synthetic gene networks," *Cell* 159, 940-954 (2014).
15. K. Pardee, A. A. Green, M. K. Takahashi, D. Braff, G. Lambert, J. W. Lee, T. Ferrante, D. Ma, N. Donghia, M. Fan, N. M. Daringer, I. Bosch, D. M. Dudley, D. H. O'Connor, L. Gehrke & J. J. Collins, "Rapid, Low-Cost Detection of Zika Virus Using Programmable Biomolecular Components," *Cell* 165, 1255-1266 (2016).
16. D. Ma, L. Shen, K. Wu, C. W. Diehnelt & A. A. Green, "Low-cost detection of norovirus using paper-based cell-free systems and synbody-based viral enrichment," *Synth Biol (Oxf)* 3, ysy018 (2018).
17. F. Hong, D. Ma, K. Wu, L. A. Mina, R. C. Luiten, Y Liu, H. Yan & A. A. Green, "Precise and Programmable Detection of Mutations Using Ultraspecific Riboregulators," *Cell* 183, 835-836 (2020).
18. S. Bhadra & A. D. Ellington, "A Spinach molecular beacon triggered by strand displacement," *RNA* 20, 1183-1194 (2014).
19. J. K. Jung, K. K. Alam, M. S. Verosloff, D. A. Capdevila, M. Desmau, P. R. Clauer, J. W. Lee, P. Q. Nguyen, P. A. Pasten, S. J. Matiasek, J. F. Gaillard, D. P. Giedroc, J. J. Collins & J. B. Lucks, "Cell-free biosensors for rapid detection of water contaminants," *Nat Biotechnol* 38, 1451-1459 (2020).
20. J. Li, A. A. Green, H. Yan & C. Fan, "Engineering nucleic acid structures for programmable molecular circuitry and intracellular biocomputation," *Nat Chem* 9, 1056-1067 (2017).
21. D. Jasinski, F. Haque, D. W. Binzel & P. Guo, "Advancement of the Emerging Field of RNA Nanotechnology," *ACS Nano* 11, 1142-1164 (2017).

51

22. Y Weizmann & E. S. Andersen, "RNA nanotechnology—The knots and folds of RNA nanoparticle engineering," *MRS Bulletin* 42, 930-935 (2017).

23. I. Severcan, C. Geary, A. Chworos, N. Voss, E. Jacovetty & L. Jaeger, "A polyhedron made of tRNAs," *Nature Chemistry* 2, 772-779 (2010).

24. C. Geary, P. W. K. Rothemund & E. S. Andersen, "A single-stranded architecture for cotranscriptional folding of RNA nanostructures," *Science* 345, 799-804 (2014).

25. D. Han, X. Qi, C. Myhrvold, B. Wang, M. Dai, S. Jiang, M. Bates, Y Liu, B. An, F. Zhang, H. Yan & P. Yin, "Single-stranded DNA and RNA origami," *Science* 358, eaao2648 (2017).

26. M. Li, M. Zheng, S. Wu, C. Tian, D. Liu, Y Weizmann, W. Jiang, G. Wang & C. Mao, "In vivo production of RNA nanostructures via programmed folding of single-stranded RNAs," *Nature Communications* 9, 2196 (2018).

27. D. Liu, C. W. Geary, G. Chen, Y Shao, M. Li, C. Mao, E. S. Andersen, J. A. Piccirilli, P. W. K. Rothemund & Y Weizmann, "Branched kissing loops for the construction of diverse RNA homooligomeric nanostructures," *Nature Chemistry* (2020).

28. D. Shu, Y Shu, F. Haque, S. Abdelmawla & P. Guo, "Thermodynamically stable RNA three-way junction for constructing multifunctional nanoparticles for delivery of therapeutics," *Nature Nanotechnology* 6, 658-667 (2011).

29. Y Nakashima, H. Abe, N. Abe, K. Aikawa & Y Ito, "Branched RNA nanostructures for RNA interference," *Chemical Communications* 47, 8367-8369 (2011).

30. K. A. Afonin, M. Kireeva, W. W. Grabow, M. Kashlev, L. Jaeger & B. A. Shapiro, "Co-transcriptional Assembly of Chemically Modified RNA Nanoparticles Functionalized with siRNAs," *Nano Letters* 12, 5192-5195 (2012).

31. C. J. Delebecque, A. B. Lindner, P. A. Silver & F. A. Aldaye, "Organization of Intracellular Reactions with Rationally Designed RNA Assemblies," *Science* 333, 470-474 (2011).

32. G. Sachdeva, A. Garg, D. Godding, J. C. Way & P. A. Silver, "In vivo co-localization of enzymes on RNA scaffolds increases metabolic production in a geometrically dependent manner," *Nucleic Acids Research* 42, 9493-9503 (2014).

33. J. Kim, P. Yin & A. A. Green, "Ribocomputing: Cellular Logic Computation Using RNA Devices," *Biochemistry* 57, 883-885 (2018).

34. A. A. Green, "Synthetic bionanotechnology: synthetic biology finds a toehold in nanotechnology," *Emerg Top Life Sci* 3, 507-516 (2019).

35. G. Rodrigo, S. Prakash, S. Shen, E. Majer, J.-A. Daros & A. Jaramillo, "Model-based design of RNA hybridization networks implemented in living cells," *Nucleic Acids Research* 45, 9797-9808 (2017).

36. J. Kim, Y Zhou, P. D. Carlson, M. Teichmann, S. Chaudhary, F. C. Simmel, P. A. Silver, J. J. Collins, J. B. Lucks, P. Yin & A. A. Green, "De novo-designed translation-repressing riboregulators for multi-input cellular logic," *Nature Chemical Biology* 15, 1173-1182 (2019).

37. J. Chappell, M. K. Takahashi & J. B. Lucks, "Creating small transcription activating RNAs," *Nat Chem Biol* 11, 214-220 (2015).

38. A. A. Green, P. A. Silver, J. J. Collins & P. Yin, "Toehold Switches: De-Novo-Designed Regulators of Gene Expression," *Cell* 159, 925-939 (2014).

39. F. Hong, D. Ma, K. Wu, L. A. Mina, R. C. Luiten, Y Liu, H. Yan & A. A. Green, "Precise and Programmable Detection of Mutations Using Ultraspecific Riboregulators," *Cell* 180, 1018-1032 (2020).

52

40. J. Kim, Y Zhou, P. D. Carlson, M. Teichmann, S. Chaudhary, F. C. Simmel, P. A. Silver, J. J. Collins, J. B. Lucks, P. Yin & A. A. Green, "De novo-designed translation-repressing riboregulators for multi-input cellular logic," *Nat Chem Biol* 15, 1173-1182 (2019).

41. J. N. Zadeh, C. D. Steenberg, J. S. Bois, B. R. Wolfe, M. B. Pierce, A. R. Khan, R. M. Dirks & N. A. Pierce, "NUPACK: Analysis and design of nucleic acid systems," *J Comput Chem* 32, 170-173 (2011).

42. K. A. Curtis, D. L. Rudolph & S. M. Owen, "Rapid detection of HIV-1 by reverse-transcription, loop-mediated isothermal amplification (RT-LAMP)," *J Virol Methods* 151, 264-270 (2008).

43. J. Hemelaar, "The origin and diversity of the HIV-1 pandemic," *Trends Mol Med* 18, 182-192 (2012).

44. T. Gräf, H. Machado Fritsch, R. M. de Medeiros, D. Maletich Junqueira, S. Esteves de Matos Almeida & A. R. Pinto, "Comprehensive Characterization of HIV-1 Molecular Epidemiology and Demographic History in the Brazilian Region Most Heavily Affected by AIDS," *Journal of Virology* 90, 8160-8168 (2016).

45. T. Gräf & A. R. Pinto, "The increasing prevalence of HIV-1 subtype C in Southern Brazil and its dispersion through the continent," *Virology* 435, 170-178 (2013).

46. L. Zou, F. Ruan, M. Huang, L. Liang, H. Huang, Z. Hong, J. Yu, M. Kang, Y Song, J. Xia, Q. Guo, T. Song, J. He, H. L. Yen, M. Peiris & J. Wu, "SARS-CoV-2 Viral Load in Upper Respiratory Specimens of Infected Patients," *N Engl J Med* 382, 1177-1179 (2020).

47. Z. D. Tong, A. Tang, K. F. Li, P. Li, H. L. Wang, J. P. Yi, Y L. Zhang & J. B. Yan, "Potential Presymptomatic Transmission of SARS-CoV-2, Zhejiang Province, China, 2020," *Emerg Infect Dis* 26, 1052-1054 (2020).

48. M. M. Arons, K. M. Hatfield, S. C. Reddy, A. Kimball, A. James, J. R. Jacobs, J. Taylor, K. Spicer, A. C. Bardossy, L. P. Oakley, S. Tanwar, J. W. Dyal, J. Harney, Z. Chisty, J. M. Bell, M. Methner, P. Paul, C. M. Carlson, H. P. McLaughlin, N. Thornburg, S. Tong, A. Tamin, Y Tao, A. Uehara, J. Harcourt, S. Clark, C. Brostrom-Smith, L. C. Page, M. Kay, J. Lewis, P. Montgomery, N. D. Stone, T. A. Clark, M. A. Honein, J. S. Duchin, J. A. Jernigan, H.-S. Public, C. King & C. C.-I. Team, "Presymptomatic SARS-CoV-2 Infections and Transmission in a Skilled Nursing Facility," *N Engl J Med* 382, 2081-2090 (2020).

49. X. Lu, L. Wang, S. K. Sakthivel, B. Whitaker, J. Murray, S. Kamili, B. Lynch, L. Malapati, S. A. Burke, J. Harcourt, A. Tamin, N. J. Thornburg, J. M. Villanueva & S. Lindstrom, "US CDC Real-Time Reverse Transcription PCR Panel for Detection of Severe Acute Respiratory Syndrome Coronavirus 2," *Emerg Infect Dis* 26 (2020).

50. W. Wang, Y Xu, R. Gao, R. Lu, K. Han, G. Wu & W. Tan, "Detection of SARS-CoV-2 in Different Types of Clinical Specimens," *JAMA* 323, 1843-1844 (2020).

51. M. H. Hanewich-Hollatz, Z. Chen, L. M. Hochrein, J. Huang & N. A. Pierce, "Conditional Guide RNAs: Programmable Conditional Regulation of CRISPR/Cas Function in Bacterial and Mammalian Cells via Dynamic RNA Nanotechnology," *ACS Cent Sci* 5, 1241-1249 (2019).

52. K. H. Siu & W. Chen, "Riboregulated toehold-gated gRNA for programmable CRISPR-Cas9 function," *Nat Chem Biol* 15, 217-220 (2019).

53. L. Oesinghaus & F. C. Simmel, "Switching the activity of Cas12a using guide RNA strand displacement circuits," *Nat Commun* 10, 2092 (2019).

54. R. Galizi, J. N. Duncan, W. Rostain, C. M. Quinn, M. Storch, M. Kushwaha & A. Jaramillo, "Engineered RNA- Interacting CRISPR Guide RNAs for Genetic Sensing and Diagnostics," *CRISPR J* 3, 398-408 (2020).

55. S. P. Collins, W. Rostain, C. Liao & C. L. Beisel, "Sequence-independent RNA sensing and DNA targeting by a split domain CRISPR-Cas12a gRNA switch," *Nucleic Acids Res* (2021).

56. Gootenberg, J. S. et al. Multiplexed and portable nucleic acid detection platform with Cas13, Cas12a, and Csm6. *Science* 360, 439-444 (2018).

57. Chen, J. S. et al. CRISPR-Cas12a target binding unleashes indiscriminate single-stranded DNase activity. *Science* 360, 436-439 (2018).

58. Myhrvold, C. et al. Field-deployable viral diagnostics using CRISPR-Cas13. *Science* 360, 444-448 (2018).

59. Broughton, J. P. et al. CRISPR-Cas12-based detection of SARS-CoV-2. *Nat. Biotechnol.* 38, 870-874 (2020).

60. Patchsung, M. et al. Clinical validation of a Cas13-based assay for the detection of SARS-CoV-2 RNA. *Nat. Biomed. Eng.* 4, 1140-1149 (2020).

What is claimed:

1. A loop-mediated riboregulator comprising a multi-arm junction upstream of the coding sequence of a reporter gene; wherein the multi-arm junction comprises from 5' to 3': a first base stem region, at least two sensor arms, and a second base stem region, and wherein the first base stem region is at least partially complementary to the second base stem region such that the first and second base stem regions pair to form a base stem; wherein each sensor arm comprises from 5' to 3': a first sensor stem region, a loop region, and a second sensor stem region, wherein the first sensor stem region is at least partially complementary to the second sensor stem region such that the first and second sensor stem regions pair to form a sensor stem, and wherein a portion of the loop region is at least partially complementary to a target RNA sequence; wherein the multi-arm junction comprises a ribosome binding site (RBS) and start codon within one of the base stem regions or sensor stem regions such that the secondary structure of the multi-arm junction conceals the RBS and start codon in the absence of target RNA sequences, and wherein binding of one or more target RNA sequences to one or more loop regions unwinds at least a portion of the secondary structure to expose the RBS and start codon thereby enabling translation of the reporter gene; and wherein the two or more target RNA sequences are from severe acute respiratory syndrome coronavirus 2 (SARS-CoV-2).

2. The loop-mediated riboregulator of claim 1, wherein the multi-arm junction further comprises one or more hairpin reconfiguration domains positioned between the two sensor arms.

3. The loop-mediated riboregulator of claim 1, wherein the multi-arm junction comprises at least three sensor arms.

4. The loop-mediated riboregulator of claim 1, wherein the loop region of the at least two sensor arms is at least 15 nucleotides in length.

5. The loop-mediated riboregulator of claim 4, wherein the loop region of the at least two sensor arms is at least 21 nucleotides in length.

6. The loop-mediated riboregulator of claim 1, wherein the sensor stem comprises one or more bulges.

7. The loop-mediated riboregulator of claim 6, wherein the sensor stem comprises four bulges.

8. The loop-mediated riboregulator of claim 1, wherein one of the sensor arms has a locked configuration and the other sensor arms have an unlocked configuration.

9. The loop-mediated riboregulator of claim 8, wherein the RBS and stop codon are positioned within the stem of the sensor arm with the locked configuration.

10. The loop-mediated riboregulator of claim 1, wherein all of the sensor arms have an unlocked configuration.

11. The loop-mediated riboregulator of claim 10, wherein the RBS and stop codon are positioned within the base stem.

12. The loop-mediated riboregulator of claim 1, wherein the two or more target RNA sequences are from a SARS-CoV-2 nucleocapsid (N) gene.

13. The loop-mediated riboregulator of claim 12, wherein each of the sensor stems comprise an RNA sequence selected from the group consisting of: SEQ ID NOs:3-6.

14. The loop-mediated riboregulator of claim 13, wherein the multi-arm junction comprises an RNA sequence selected from SEQ ID NO:1 and SEQ ID NO:2.

15. The loop-mediated riboregulator of claim 1, wherein the reporter gene is a resistance gene or a gene encoding a fluorescent protein.

16. A DNA construct comprising a promoter and a sequence encoding the loop-mediated riboregulator of claim 1.

17. A method for detecting the presence of two or more target RNA sequences from SARS-CoV-2 in a sample, the method comprising:
   a) providing a sample comprising RNA;
   b) contacting the sample with the loop-mediated riboregulator of claim 1;
   c) detecting translation of the reporter gene;
wherein translation of the reporter gene indicates that SARS-CoV-2 is present in the sample.

18. The method of claim 17, wherein the method is carried out in a paper-based cell-free system.

19. The method of claim 17, wherein translation of the reporter gene produces a colorimetric readout.

20. The method of claim 17, wherein the RNA in the sample is amplified prior to step (b).

* * * * *

SEQUENCE LISTING

```
Sequence total quantity: 232
SEQ ID NO: 1            moltype = RNA  length = 219
FEATURE                 Location/Qualifiers
source                  1..219
                        mol_type = other RNA
                        organism = synthetic construct
SEQUENCE: 1
gggactcaaa tcttcgctac agcgacatct acacattacg tttggtggac cctcagattc  60
aactaaacct aatgggtaga actcgctaaa gcgatgtcta cctgccatat cttatctcct  120
gaactgatta caaacattgg ccgcaaattg tgtattcagt agaggagata caatatggca  180
attagacaag atacgagtaa cctggcggca gcgcaaaag                         219

SEQ ID NO: 2            moltype = RNA  length = 219
FEATURE                 Location/Qualifiers
source                  1..219
                        mol_type = other RNA
                        organism = synthetic construct
SEQUENCE: 2
gggactcaaa tcttcgctac agcgacatct acaggaactg attacaaaca ttggccgcaa  60
attgaatctg ttccggtaga actcgctaaa gcgatgtcta cctgccatat cttatctcct  120
gactgcgttc tccattctgg ttactgccag gagaacgcag agaggagata caatatggca  180
attagacaag atacgagtaa cctggcggca gcgcaaaag                         219

SEQ ID NO: 3            moltype = RNA  length = 81
FEATURE                 Location/Qualifiers
source                  1..81
                        mol_type = other RNA
                        organism = synthetic construct
SEQUENCE: 3
tcgctacagc gacatctaca cattacgttt ggtggaccct cagattcaac taaacctaat  60
gggtagaact cgctaaagcg a                                            81

SEQ ID NO: 4            moltype = RNA  length = 94
FEATURE                 Location/Qualifiers
source                  1..94
                        mol_type = other RNA
                        organism = synthetic construct
SEQUENCE: 4
tgtctacctg ccatatctta tctcctgaac tgattacaaa cattggccgc aaattgtgta  60
ttcagtagag gagatacaat atggcaatta gaca                              94

SEQ ID NO: 5            moltype = RNA  length = 81
FEATURE                 Location/Qualifiers
source                  1..81
                        mol_type = other RNA
                        organism = synthetic construct
SEQUENCE: 5
tcgctacagc gacatctaca ggaactgatt acaaacattg gccgcaaatt gaatctgttc  60
cggtagaact cgctaaagcg a                                            81

SEQ ID NO: 6            moltype = RNA  length = 94
FEATURE                 Location/Qualifiers
source                  1..94
                        mol_type = other RNA
                        organism = synthetic construct
SEQUENCE: 6
tgtctacctg ccatatctta tctcctgaac tgattacaaa cattggccgc aaattgtgta  60
ttcagtagag gagatacaat atggcaatta gaca                              94

SEQ ID NO: 7            moltype = DNA  length = 54
FEATURE                 Location/Qualifiers
source                  1..54
                        mol_type = other DNA
                        organism = synthetic construct
SEQUENCE: 7
```

-continued

```
ctagtaaatt cgcgtttcta cggtagccgg gcgctaatac gactcactat aggg              54

SEQ ID NO: 8          moltype = DNA   length = 21
FEATURE               Location/Qualifiers
source                1..21
                      mol_type = other DNA
                      organism = synthetic construct
SEQUENCE: 8
cttttgcgct gccgccaggt t                                                  21

SEQ ID NO: 9          moltype = DNA   length = 29
FEATURE               Location/Qualifiers
source                1..29
                      mol_type = other DNA
                      organism = synthetic construct
SEQUENCE: 9
cccgtttaga ggccccaagg ggttatgct                                          29

SEQ ID NO: 10         moltype = DNA   length = 18
FEATURE               Location/Qualifiers
source                1..18
                      mol_type = other DNA
                      organism = synthetic construct
SEQUENCE: 10
aacctggcgg cagcgcaa                                                      18

SEQ ID NO: 11         moltype = DNA   length = 19
FEATURE               Location/Qualifiers
source                1..19
                      mol_type = other DNA
                      organism = synthetic construct
SEQUENCE: 11
tagcataacc ccttggggc                                                     19

SEQ ID NO: 12         moltype = DNA   length = 55
FEATURE               Location/Qualifiers
source                1..55
                      mol_type = other DNA
                      organism = synthetic construct
SEQUENCE: 12
aacctggcgg cagcgcaaaa gatgcgtaaa atgaccatga ttacggattc actgg            55

SEQ ID NO: 13         moltype = DNA   length = 51
FEATURE               Location/Qualifiers
source                1..51
                      mol_type = other DNA
                      organism = synthetic construct
SEQUENCE: 13
ccggctaccg tagaaacgcg aatttactag cgagatctcg atcctctacg c                51

SEQ ID NO: 14         moltype = DNA   length = 52
FEATURE               Location/Qualifiers
source                1..52
                      mol_type = other DNA
                      organism = synthetic construct
SEQUENCE: 14
ccggctaccg tagaaacgcg aatttactag cataagggag agcgtcgaga tc               52

SEQ ID NO: 15         moltype = DNA   length = 19
FEATURE               Location/Qualifiers
source                1..19
                      mol_type = other DNA
                      organism = synthetic construct
SEQUENCE: 15
cctgccacca tacccacgc                                                     19

SEQ ID NO: 16         moltype = DNA   length = 26
FEATURE               Location/Qualifiers
source                1..26
                      mol_type = other DNA
                      organism = synthetic construct
SEQUENCE: 16
cgttactggt ttcacattca ccaccc                                             26

SEQ ID NO: 17         moltype = RNA   length = 111
FEATURE               Location/Qualifiers
source                1..111
                      mol_type = other RNA
                      organism = synthetic construct
```

```
SEQUENCE: 17
gggtctatct atttcacatc tcctaagttt ccgtattctg tgaagcccta gggtccgata     60
cagaaacaga ggagatgaca aatgaataga aacctggcgg cagcgcaaaa g             111

SEQ ID NO: 18           moltype = RNA   length = 111
FEATURE                 Location/Qualifiers
source                  1..111
                        mol_type = other RNA
                        organism = synthetic construct
SEQUENCE: 18
gggtccattc atatactatc tcctaagttc tcgttccaat tcgctctcgt cctgtccgaa     60
caagaacaga ggagataaga tatgaatgga aacctggcgg cagcgcaaaa g             111

SEQ ID NO: 19           moltype = RNA   length = 111
FEATURE                 Location/Qualifiers
source                  1..111
                        mol_type = other RNA
                        organism = synthetic construct
SEQUENCE: 19
gggcttatca atatcacatc tcctacgtct ttagtcgctt cgggacagtg tgcatccgac     60
taaagacaga ggagatgaca tatgaataag aacctggcgg cagcgcaaaa g             111

SEQ ID NO: 20           moltype = RNA   length = 111
FEATURE                 Location/Qualifiers
source                  1..111
                        mol_type = other RNA
                        organism = synthetic construct
SEQUENCE: 20
gggcgttgaa atctgctatc tcctacgtat tagtttatgc taccgtaagc ctgtctcaaa     60
cgaatacaga ggagatacaa gatgacaacg aacctggcgg cagcgcaaaa g             111

SEQ ID NO: 21           moltype = RNA   length = 111
FEATURE                 Location/Qualifiers
source                  1..111
                        mol_type = other RNA
                        organism = synthetic construct
SEQUENCE: 21
gggtagtgcc atatcttatc tcctgagttt catcttaaag tccttgtaac agtcgtcaag     60
acgaaacaga ggagataaca tatgacacta aacctggcgg cagcgcaaaa g             111

SEQ ID NO: 22           moltype = RNA   length = 111
FEATURE                 Location/Qualifiers
source                  1..111
                        mol_type = other RNA
                        organism = synthetic construct
SEQUENCE: 22
gggatgtcca attacctgtc tcctgagtct actctacctc gctcgttctc atgactctag     60
aatagacaga ggagacacat aatgggacat aacctggcgg cagcgcaaaa g             111

SEQ ID NO: 23           moltype = RNA   length = 111
FEATURE                 Location/Qualifiers
source                  1..111
                        mol_type = other RNA
                        organism = synthetic construct
SEQUENCE: 23
gggcattgga atcgagtatc tcctacgttt aacttaaccc tataccctca taacccttaa     60
gataaacaga ggagatatac gatggcaatg aacctggcgg cagcgcaaaa g             111

SEQ ID NO: 24           moltype = RNA   length = 111
FEATURE                 Location/Qualifiers
source                  1..111
                        mol_type = other RNA
                        organism = synthetic construct
SEQUENCE: 24
gggatgtaca atccattatc tcctaagtct tattctactg ccttgttcca ctcccgtaga     60
acaagacaga ggagataacg gatgatacat aacctggcgg cagcgcaaaa g             111

SEQ ID NO: 25           moltype = RNA   length = 111
FEATURE                 Location/Qualifiers
source                  1..111
                        mol_type = other RNA
                        organism = synthetic construct
SEQUENCE: 25
gggcattaca attacctatc tcctacattc tagtgccacg agttagtatc ttcgcctgca     60
caagaataga ggagatagat aatggtaatg aacctggcgg cagcgcaaaa g             111

SEQ ID NO: 26           moltype = RNA   length = 111
FEATURE                 Location/Qualifiers
source                  1..111
```

```
                        mol_type = other RNA
                        organism = synthetic construct
SEQUENCE: 26
gggcatatga atcggaagtc tcctacagtc atttcgtctt cgaggccgtc tcatctgcga   60
actgactaga ggagactaac gatgaatatg aacctggcgg cagcgcaaaa g           111

SEQ ID NO: 27          moltype = RNA   length = 111
FEATURE                Location/Qualifiers
source                 1..111
                        mol_type = other RNA
                        organism = synthetic construct
SEQUENCE: 27
gggcatcaca attacatatc tcctgaatct tcattccatt ccattgtctc cagaccggaa   60
tgaagataga ggagatagat aatgatgatg aacctggcgg cagcgcaaaa g           111

SEQ ID NO: 28          moltype = RNA   length = 111
FEATURE                Location/Qualifiers
source                 1..111
                        mol_type = other RNA
                        organism = synthetic construct
SEQUENCE: 28
gggatcatag atgcagtatc tcctaaactt ccacttcgat cgcaggtttc acactacaag   60
tagaagtaga ggagataacg catgaatgat aacctggcgg cagcgcaaaa g           111

SEQ ID NO: 29          moltype = RNA   length = 111
FEATURE                Location/Qualifiers
source                 1..111
                        mol_type = other RNA
                        organism = synthetic construct
SEQUENCE: 29
gggtcgttca atgtagtatc tcctaagtcg tttctagtac gagatcgcct gttcccatag   60
atacgacaga ggagataaga catgaaacga aacctggcgg cagcgcaaaa g           111

SEQ ID NO: 30          moltype = RNA   length = 111
FEATURE                Location/Qualifiers
source                 1..111
                        mol_type = other RNA
                        organism = synthetic construct
SEQUENCE: 30
gggcatttgc atataccatc tcctaagtct tattcgtgac gcttaagtcc cgcagagcga   60
ataagacaga ggagatgaga tatggaaatg aacctggcgg cagcgcaaaa g           111

SEQ ID NO: 31          moltype = RNA   length = 111
FEATURE                Location/Qualifiers
source                 1..111
                        mol_type = other RNA
                        organism = synthetic construct
SEQUENCE: 31
gggccataca atcaaccgtc tcctaagtat tccataccg tgtcaatctc tataagcatt    60
gaaatacaga ggagacggat gatgatatgg aacctggcgg cagcgcaaaa g           111

SEQ ID NO: 32          moltype = RNA   length = 111
FEATURE                Location/Qualifiers
source                 1..111
                        mol_type = other RNA
                        organism = synthetic construct
SEQUENCE: 32
gggcaattac atgcaacgtc tcctacattc ttatctatca aagttcacgc actacgcaga   60
taagaataga ggagacgaag catgaaattg aacctggcgg cagcgcaaaa g           111

SEQ ID NO: 33          moltype = RNA   length = 111
FEATURE                Location/Qualifiers
source                 1..111
                        mol_type = other RNA
                        organism = synthetic construct
SEQUENCE: 33
gggactctac atgtactatc tcctacgttt atctatgctc ctatatcgtc acgtctgata   60
gataaacaga ggagataaga catgcagagt aacctggcgg cagcgcaaaa g           111

SEQ ID NO: 34          moltype = RNA   length = 111
FEATURE                Location/Qualifiers
source                 1..111
                        mol_type = other RNA
                        organism = synthetic construct
SEQUENCE: 34
gggatctacc attcattatc tcctaggttt cagttctatt agggctacga agaccgtgaa   60
cagaaacaga ggagatacgg aatgatagat aacctggcgg cagcgcaaaa g           111

SEQ ID NO: 35          moltype = RNA   length = 111
```

-continued

```
FEATURE                 Location/Qualifiers
source                  1..111
                        mol_type = other RNA
                        organism = synthetic construct
SEQUENCE: 35
gggcttatac atttaccgtc tcctaagctt agtcgtgaaa cctatacaat cctgtgcacg   60
aataagcaga ggagacgaca aatgaataag aacctggcgg cagcgcaaaa g          111

SEQ ID NO: 36           moltype = RNA   length = 111
FEATURE                 Location/Qualifiers
source                  1..111
                        mol_type = other RNA
                        organism = synthetic construct
SEQUENCE: 36
gggcttagca atgtagaatc tcctgagtta gttcccattg ttactttcac atctcacggg   60
aactaacaga ggagattgaa catgactaag aacctggcgg cagcgcaaaa g          111

SEQ ID NO: 37           moltype = RNA   length = 111
FEATURE                 Location/Qualifiers
source                  1..111
                        mol_type = other RNA
                        organism = synthetic construct
SEQUENCE: 37
gggcctaaca atgtaccgtc tcctaagtct cgatcccggt atcttatggc ctggtcggga   60
tagagacaga ggagacgaaa catgattagg aacctggcgg cagcgcaaaa g          111

SEQ ID NO: 38           moltype = RNA   length = 111
FEATURE                 Location/Qualifiers
source                  1..111
                        mol_type = other RNA
                        organism = synthetic construct
SEQUENCE: 38
gggcttatcc atttcacgtc tcctacgcct tcatcgtcgt cttgcaccgt cctactccga   60
taaaggcaga ggagacgaca aatgaataag aacctggcgg cagcgcaaaa g          111

SEQ ID NO: 39           moltype = RNA   length = 111
FEATURE                 Location/Qualifiers
source                  1..111
                        mol_type = other RNA
                        organism = synthetic construct
SEQUENCE: 39
gggcctaaca attctatatc tcctaagtgt cagttcttag gctacacatg tgagtgtgaa   60
cagacacaga ggagataacg aatgattagg aacctggcgg cagcgcaaaa g          111

SEQ ID NO: 40           moltype = RNA   length = 111
FEATURE                 Location/Qualifiers
source                  1..111
                        mol_type = other RNA
                        organism = synthetic construct
SEQUENCE: 40
gggcttatca attgcacatc tcctaggtca tctcgtccaa atcgatcatc actgtccacg   60
agatgacaga ggagatgaac aatggataag aacctggcgg cagcgcaaaa g          111

SEQ ID NO: 41           moltype = RNA   length = 58
FEATURE                 Location/Qualifiers
source                  1..58
                        mol_type = other RNA
                        organism = synthetic construct
SEQUENCE: 41
gggccagtga cttgtcactg ggaacggacc ctagggcttc acagaatacg gaaacgac     58

SEQ ID NO: 42           moltype = RNA   length = 58
FEATURE                 Location/Qualifiers
source                  1..58
                        mol_type = other RNA
                        organism = synthetic construct
SEQUENCE: 42
gggagtggca cgcgtgccac taatggacag gacgagagcg aattggaacg agaacgac     58

SEQ ID NO: 43           moltype = RNA   length = 58
FEATURE                 Location/Qualifiers
source                  1..58
                        mol_type = other RNA
                        organism = synthetic construct
SEQUENCE: 43
gggtctccac ggaagtggag ataaggatgc acactgtccc gaagcgacta aagacaaa     58

SEQ ID NO: 44           moltype = RNA   length = 58
FEATURE                 Location/Qualifiers
```

-continued

```
source                   1..58
                         mol_type = other RNA
                         organism = synthetic construct
SEQUENCE: 44
gggcacggac tcctgtccgt gggcgagaca ggcttacggt agcataaact aatacaac     58

SEQ ID NO: 45            moltype = RNA   length = 58
FEATURE                  Location/Qualifiers
source                   1..58
                         mol_type = other RNA
                         organism = synthetic construct
SEQUENCE: 45
gggctcacct gccaaggtga gagcgacgac tgttacaagg actttaagat gaaacgac     58

SEQ ID NO: 46            moltype = RNA   length = 58
FEATURE                  Location/Qualifiers
source                   1..58
                         mol_type = other RNA
                         organism = synthetic construct
SEQUENCE: 46
gggctggagc atacgctcca gaatgagtca tgagaacgag cgaggtagag tagacgaa     58

SEQ ID NO: 47            moltype = RNA   length = 58
FEATURE                  Location/Qualifiers
source                   1..58
                         mol_type = other RNA
                         organism = synthetic construct
SEQUENCE: 47
gggacaatgt aagaacattg tacgagggtt atgagggtat agggttaagt taaacagc     58

SEQ ID NO: 48            moltype = RNA   length = 58
FEATURE                  Location/Qualifiers
source                   1..58
                         mol_type = other RNA
                         organism = synthetic construct
SEQUENCE: 48
gggatcctga atactcagga tgaaacggga gtggaacaag gcagtagaat aagacaac     58

SEQ ID NO: 49            moltype = RNA   length = 58
FEATURE                  Location/Qualifiers
source                   1..58
                         mol_type = other RNA
                         organism = synthetic construct
SEQUENCE: 49
gggtccgatc tagagatcgg ataaaggcga agatactaac tcgtggcact agaataca     58

SEQ ID NO: 50            moltype = RNA   length = 58
FEATURE                  Location/Qualifiers
source                   1..58
                         mol_type = other RNA
                         organism = synthetic construct
SEQUENCE: 50
gggatccagc cgatgctgga tgaacagatg agacggcctc gaagacgaaa tgactaga     58

SEQ ID NO: 51            moltype = RNA   length = 58
FEATURE                  Location/Qualifiers
source                   1..58
                         mol_type = other RNA
                         organism = synthetic construct
SEQUENCE: 51
gggagccatc gcatgatggc tggacggtct ggagacaatg gaatggaatg aagatact     58

SEQ ID NO: 52            moltype = RNA   length = 58
FEATURE                  Location/Qualifiers
source                   1..58
                         mol_type = other RNA
                         organism = synthetic construct
SEQUENCE: 52
gggcagctac tcaagtagct ggaggtagtg tgaaacctgc gatcgaagtg gaagtacg     58

SEQ ID NO: 53            moltype = RNA   length = 58
FEATURE                  Location/Qualifiers
source                   1..58
                         mol_type = other RNA
                         organism = synthetic construct
SEQUENCE: 53
gggagtcagc tgatgctgac taagtgggaa caggcgatct cgtactagaa acgacaat     58

SEQ ID NO: 54            moltype = RNA   length = 58
```

-continued

```
FEATURE                   Location/Qualifiers
source                    1..58
                          mol_type = other RNA
                          organism = synthetic construct
SEQUENCE: 54
gggcgtcacc tttaggtgac ggaactctgc gggacttaag cgtcacgaat aagacaca      58

SEQ ID NO: 55             moltype = RNA   length = 58
FEATURE                   Location/Qualifiers
source                    1..58
                          mol_type = other RNA
                          organism = synthetic construct
SEQUENCE: 55
gggcagaccc tgctgggtct ggacgcttat agagattgac acggtattgg aatacaaa      58

SEQ ID NO: 56             moltype = RNA   length = 58
FEATURE                   Location/Qualifiers
source                    1..58
                          mol_type = other RNA
                          organism = synthetic construct
SEQUENCE: 56
gggacgttac ttaggtaacg tggagcgtag tgcgtgaact ttgatagata agaatgaa      58

SEQ ID NO: 57             moltype = RNA   length = 58
FEATURE                   Location/Qualifiers
source                    1..58
                          mol_type = other RNA
                          organism = synthetic construct
SEQUENCE: 57
gggagctcgc aaccgcgagc tagacagacg tgacgatata ggagcataga taaactca      58

SEQ ID NO: 58             moltype = RNA   length = 58
FEATURE                   Location/Qualifiers
source                    1..58
                          mol_type = other RNA
                          organism = synthetic construct
SEQUENCE: 58
gggagcatgc cgtggcatgc taggacggtc ttcgtagccc taatagaact gaaacatg      58

SEQ ID NO: 59             moltype = RNA   length = 58
FEATURE                   Location/Qualifiers
source                    1..58
                          mol_type = other RNA
                          organism = synthetic construct
SEQUENCE: 59
gggcacagac gtacgtctgt ggaagcacag gattgtatag gtttcacgac taagcgaa      58

SEQ ID NO: 60             moltype = RNA   length = 58
FEATURE                   Location/Qualifiers
source                    1..58
                          mol_type = other RNA
                          organism = synthetic construct
SEQUENCE: 60
gggcctacgc actcgcgtag gattgtgaga tgtgaaagta acaatgggaa ctaacgaa      58

SEQ ID NO: 61             moltype = RNA   length = 58
FEATURE                   Location/Qualifiers
source                    1..58
                          mol_type = other RNA
                          organism = synthetic construct
SEQUENCE: 61
gggccagacc atcgggtctg gaggcgacca ggccataaga taccgggatc gagacaac      58

SEQ ID NO: 62             moltype = RNA   length = 58
FEATURE                   Location/Qualifiers
source                    1..58
                          mol_type = other RNA
                          organism = synthetic construct
SEQUENCE: 62
gggaccgtac tcccgtacgg tgatgagtag gacggtgcaa gacgacgatg aaggctac      58

SEQ ID NO: 63             moltype = RNA   length = 58
FEATURE                   Location/Qualifiers
source                    1..58
                          mol_type = other RNA
                          organism = synthetic construct
SEQUENCE: 63
gggatgatcg acaccgatca tagaacactc acatgtgtag cctaagaact gacacagc      58
```

-continued

```
SEQ ID NO: 64            moltype = RNA   length = 58
FEATURE                  Location/Qualifiers
source                   1..58
                         mol_type = other RNA
                         organism = synthetic construct
SEQUENCE: 64
gggctgctcc cgtgggagca ggacggacag tgatgatcga tttggacgag atgacata      58

SEQ ID NO: 65            moltype = RNA   length = 118
FEATURE                  Location/Qualifiers
source                   1..118
                         mol_type = other RNA
                         organism = synthetic construct
SEQUENCE: 65
gggatctacc attcattatc tcctagaggt ttcatttagc gcctcaaata gatcctgttc      60
agtaaatgta acctagagga gatacggaat gatagataac ctggcggcag cgcaaaag      118

SEQ ID NO: 66            moltype = RNA   length = 118
FEATURE                  Location/Qualifiers
source                   1..118
                         mol_type = other RNA
                         organism = synthetic construct
SEQUENCE: 66
gggatctacc attcattatc tcctagatct gtctatttcg ttcatccata gttgcctgac      60
tgaaatagac agatagagga gatacggaat gatagataac ctggcggcag cgcaaaag      118

SEQ ID NO: 67            moltype = RNA   length = 118
FEATURE                  Location/Qualifiers
source                   1..118
                         mol_type = other RNA
                         organism = synthetic construct
SEQUENCE: 67
gggatctacc attcattatc tcctagacga aaaacatatt ctcaataaac cctttaggga      60
aatatgttat tcgtagagga gatacggaat gatagataac ctggcggcag cgcaaaag      118

SEQ ID NO: 68            moltype = RNA   length = 118
FEATURE                  Location/Qualifiers
source                   1..118
                         mol_type = other RNA
                         organism = synthetic construct
SEQUENCE: 68
gggatctacc attcattatc tcctagcttg gccttgtagg tggtcttgac ctcagcgtcg      60
tatacaagac caagagagga gatacggaat gatagataac ctggcggcag cgcaaaag      118

SEQ ID NO: 69            moltype = RNA   length = 39
FEATURE                  Location/Qualifiers
source                   1..39
                         mol_type = other RNA
                         organism = synthetic construct
SEQUENCE: 69
gggctgaaca ggatctattt gaggcgctaa atgaaacct                            39

SEQ ID NO: 70            moltype = RNA   length = 39
FEATURE                  Location/Qualifiers
source                   1..39
                         mol_type = other RNA
                         organism = synthetic construct
SEQUENCE: 70
gggatctgtc tatttcgttc atccatagtt gcctgactg                            39

SEQ ID NO: 71            moltype = RNA   length = 39
FEATURE                  Location/Qualifiers
source                   1..39
                         mol_type = other RNA
                         organism = synthetic construct
SEQUENCE: 71
gggtttccct aaagggttta ttgagaatat gtttttcgt                            39

SEQ ID NO: 72            moltype = RNA   length = 39
FEATURE                  Location/Qualifiers
source                   1..39
                         mol_type = other RNA
                         organism = synthetic construct
SEQUENCE: 72
gggtacgacg ctgaggtcaa gaccacctac aaggccaag                            39

SEQ ID NO: 73            moltype = RNA   length = 202
FEATURE                  Location/Qualifiers
source                   1..202
```

```
                              mol_type = other RNA
                              organism = synthetic construct
SEQUENCE: 73
gggattcatt tcacatctcc taatccagtc gtggatgggc tctgtttccg tattctgtga    60
agccctaggg tccgatacag aaacagagcc catccacgac tggaatggct ctgtttcatc   120
ttaaagtcct tgtaacagtc gtcaagacga aactaagcca tagaggagat gacaaatgaa   180
taacctggcg gcagcgcaaa ag                                            202

SEQ ID NO: 74            moltype = RNA   length = 58
FEATURE                  Location/Qualifiers
source                   1..58
                         mol_type = other RNA
                         organism = synthetic construct
SEQUENCE: 74
gggccagtga cttgtcactg ggaacggacc ctagggcttc acagaatacg gaaacgac      58

SEQ ID NO: 75            moltype = RNA   length = 58
FEATURE                  Location/Qualifiers
source                   1..58
                         mol_type = other RNA
                         organism = synthetic construct
SEQUENCE: 75
gggctcacct gccaaggtga gagcgacgac tgttacaagg actttaagat gaaacgac      58

SEQ ID NO: 76            moltype = RNA   length = 283
FEATURE                  Location/Qualifiers
source                   1..283
                         mol_type = other RNA
                         organism = synthetic construct
SEQUENCE: 76
gggattcatt tcacatctcc tcctccagtc gtggatgggc tctgtttccg tattctgtga    60
agccctaggg tccgatacag aaactgagcc attccacatc tggatccagt cgtggatggg   120
ctctgcttag tcgtgaaacc tatacaatcc tgtgcacgaa taagctgagc cattccacat   180
ctggataggc tcagtttcat cttaaagtcc ttgtaacagt cgtcaagacg aaaccaagcc   240
taagaggaga tgacaaatga ataacctggc ggcagcgcaa aag                      283

SEQ ID NO: 77            moltype = RNA   length = 58
FEATURE                  Location/Qualifiers
source                   1..58
                         mol_type = other RNA
                         organism = synthetic construct
SEQUENCE: 77
gggccagtga cttgtcactg ggaacggacc ctagggcttc acagaatacg gaaacgac      58

SEQ ID NO: 78            moltype = RNA   length = 58
FEATURE                  Location/Qualifiers
source                   1..58
                         mol_type = other RNA
                         organism = synthetic construct
SEQUENCE: 78
gggctcacct gccaaggtga gagcgacgac tgttacaagg actttaagat gaaacgac      58

SEQ ID NO: 79            moltype = RNA   length = 58
FEATURE                  Location/Qualifiers
source                   1..58
                         mol_type = other RNA
                         organism = synthetic construct
SEQUENCE: 79
gggcacagac gtacgtctgt ggaagcacag gattgtatag gtttcacgac taagcgaa      58

SEQ ID NO: 80            moltype = RNA   length = 164
FEATURE                  Location/Qualifiers
source                   1..164
                         mol_type = other RNA
                         organism = synthetic construct
SEQUENCE: 80
gggcgtgaac cagtttccgt attctgtgaa gccctagggt ccgatactga aactatcata    60
tcttatctcc tgagtttcat cttaaagtcc ttgtaacagt cgtcaagacg aaacagagga   120
gataacatat gatatggtgc acgaacctgg cggcagcgca aaag                     164

SEQ ID NO: 81            moltype = RNA   length = 58
FEATURE                  Location/Qualifiers
source                   1..58
                         mol_type = other RNA
                         organism = synthetic construct
SEQUENCE: 81
gggccagtga cttgtcactg ggaacggacc ctagggcttc acagaatacg gaaacgac      58

SEQ ID NO: 82            moltype = RNA   length = 58
```

```
FEATURE                 Location/Qualifiers
source                  1..58
                        mol_type = other RNA
                        organism = synthetic construct
SEQUENCE: 82
gggctcacct gccaaggtga gagcgacgac tgttacaagg actttaagat gaaacgac      58

SEQ ID NO: 83           moltype = RNA   length = 327
FEATURE                 Location/Qualifiers
source                  1..327
                        mol_type = other RNA
                        organism = synthetic construct
SEQUENCE: 83
gggcgggtac ctcgttccgt gcggaatctt ggaggcttag tcgtgaaacc tatacaatcc      60
tgtgcacgaa taagcatcca agattccgct cggaaagttg gattcaattc gcgagaataa     120
catcacgttt ccgtattctg tgaagcccta gggtccgata cagaaacttg atggcattct     180
ttcgaatcac atcaaaatca tctcatgtct cctgagtttc atcttaaagt ccttgtaaca     240
gtcgtcaaga cgaaacagag gagacaacag atgattgcga tgtgtgaatc caactcgagg     300
tacccgaacc tggcggcagc gcaaaag                                         327

SEQ ID NO: 84           moltype = RNA   length = 58
FEATURE                 Location/Qualifiers
source                  1..58
                        mol_type = other RNA
                        organism = synthetic construct
SEQUENCE: 84
gggccagtga cttgtcactg ggaacggacc ctagggcttc acagaatacg gaaacgac      58

SEQ ID NO: 85           moltype = RNA   length = 58
FEATURE                 Location/Qualifiers
source                  1..58
                        mol_type = other RNA
                        organism = synthetic construct
SEQUENCE: 85
gggctcacct gccaaggtga gagcgacgac tgttacaagg actttaagat gaaacgac      58

SEQ ID NO: 86           moltype = RNA   length = 58
FEATURE                 Location/Qualifiers
source                  1..58
                        mol_type = other RNA
                        organism = synthetic construct
SEQUENCE: 86
gggcacagac gtacgtctgt ggaagcacag gattgtatag gtttcacgac taagcgaa      58

SEQ ID NO: 87           moltype = RNA   length = 126
FEATURE                 Location/Qualifiers
source                  1..126
                        mol_type = other RNA
                        organism = synthetic construct
SEQUENCE: 87
gggtaacgga tgatgtacaa tccattatct cctaagtcct cctactccct gacatgctgt      60
catcatttct tcgtaggagg acagaggaga taacggatga tacataacct ggcggcagcg     120
caaaag                                                               126

SEQ ID NO: 88           moltype = RNA   length = 126
FEATURE                 Location/Qualifiers
source                  1..126
                        mol_type = other RNA
                        organism = synthetic construct
SEQUENCE: 88
gggtaacgga tgatgtacaa tccattatct cctaacttat ggccgggtcc tcctactccc      60
tgacatgctg tccggccata agagaggaga taacggatga tacataacct ggcggcagcg     120
caaaag                                                               126

SEQ ID NO: 89           moltype = RNA   length = 126
FEATURE                 Location/Qualifiers
source                  1..126
                        mol_type = other RNA
                        organism = synthetic construct
SEQUENCE: 89
gggtaacgga tgatgtacaa tccattatct cctaagtgg cttcggctct tggtgaattg      60
ggcgttatct cacgaagcca ccagaggaga taacggatga tacataacct ggcggcagcg     120
caaaag                                                               126

SEQ ID NO: 90           moltype = RNA   length = 126
FEATURE                 Location/Qualifiers
source                  1..126
                        mol_type = other RNA
                        organism = synthetic construct
```

```
SEQUENCE: 90
gggtaacgga tgatgtacaa tccattatct cctaagatga gattctcaga tctgagcacg    60
tgggagggcg atgaatctca tcagaggaga taacggatga tacataacct ggcggcagcg   120
caaaag                                                              126

SEQ ID NO: 91           moltype = RNA   length = 126
FEATURE                 Location/Qualifiers
source                  1..126
                        mol_type = other RNA
                        organism = synthetic construct
SEQUENCE: 91
gggtaacgga tgatgtacaa tccattatct cctaagaaaa accctgggcg tcaatatggt    60
acgacgagga gtagggtttt tcagaggaga taacggatga tacataacct ggcggcagcg   120
caaaag                                                              126

SEQ ID NO: 92           moltype = RNA   length = 126
FEATURE                 Location/Qualifiers
source                  1..126
                        mol_type = other RNA
                        organism = synthetic construct
SEQUENCE: 92
gggtaacgga tgatgtacaa tccattatct cctaagccaa aattcctgct gttggggta     60
tggctagaaa tcgaattttg gcagaggaga taacggatga tacataacct ggcggcagcg   120
caaaag                                                              126

SEQ ID NO: 93           moltype = RNA   length = 187
FEATURE                 Location/Qualifiers
source                  1..187
                        mol_type = other RNA
                        organism = synthetic construct
SEQUENCE: 93
gggccccaag gggttatgct atgctatgtc acttcccctt ggttctctca tctggcctgg    60
tgcaataggc cctgcatgca ctggatgcac tctatcccat tctgcagctt cctcattgat   120
ggtctctttt aacatttgca tggctgcttg atgtccccc actccctata gtgagtcgta    180
ttagcgc                                                             187

SEQ ID NO: 94           moltype = RNA   length = 187
FEATURE                 Location/Qualifiers
source                  1..187
                        mol_type = other RNA
                        organism = synthetic construct
SEQUENCE: 94
gggccccaag gggttatgct aattgcctct ctgcatcatt atggtagctg aatttgttac    60
ttggctcatt gcttcagcca aaactcttgc cttatggccg ggtcctccta ctccctgaca   120
tgctgtcatc atttcttcta gtgtagccgc tggtcccaat gctccctata gtgagtcgta    180
ttagcgc                                                             187

SEQ ID NO: 95           moltype = RNA   length = 174
FEATURE                 Location/Qualifiers
source                  1..174
                        mol_type = other RNA
                        organism = synthetic construct
SEQUENCE: 95
gggcctgtcc tcggttcaca atcaagtcct aggcttccaa accccccag ggtggcttcg     60
gctcttggtg aattgggcgt tatctcaact ttcgctctat tctcatcagt ttcatgtcct   120
gtgtcattaa cgatcatccc actgtgctgg ccctatagtg agtcgtatta gcgc          174

SEQ ID NO: 96           moltype = RNA   length = 201
FEATURE                 Location/Qualifiers
source                  1..201
                        mol_type = other RNA
                        organism = synthetic construct
SEQUENCE: 96
gggatggatt tttacgtgcc caggcaagag ccaatgttca gatggatgag attctcagat    60
ctgagcacgt gggagggcga tcgcaatctg gctcccagtt ttgtgaatga agatggcgtc   120
gaatgacgcc aacccatctg atgggtccgc agccaacctc gtcccagagg tcaacaatga   180
ggttatggct ttggagcccg t                                             201

SEQ ID NO: 97           moltype = DNA   length = 51
FEATURE                 Location/Qualifiers
source                  1..51
                        mol_type = other DNA
                        organism = synthetic construct
SEQUENCE: 97
aattctaata cgactcacta tagggagaag gctcattgtt gacctctggg a             51

SEQ ID NO: 98           moltype = DNA   length = 20
FEATURE                 Location/Qualifiers
source                  1..20
```

-continued

```
                         mol_type = other DNA
                         organism = synthetic construct
SEQUENCE: 98
caggcaagag ccaatgttca                                          20

SEQ ID NO: 99          moltype = RNA   length = 251
FEATURE                Location/Qualifiers
source                 1..251
                       mol_type = other RNA
                       organism = synthetic construct
SEQUENCE: 99
gggtgctaat tgaggtgcat tggtctgcaa atcgagttgc taggcaataa acacatttgg   60
attaatttta atcgttcgtt gagcgattag cagagaactg accagaacat gtctggtcgt   120
aaagctcagg gaaaaaccct gggcgtcaat atggtacgac gaggagttcg ctccttgtca   180
aacaaaataa aacaaaaaac aaaacaaatt ggaaacagac ctggaccttc aagaggtgtt   240
caaggattta t                                                       251

SEQ ID NO: 100         moltype = DNA   length = 55
FEATURE                Location/Qualifiers
source                 1..55
                       mol_type = other DNA
                       organism = synthetic construct
SEQUENCE: 100
aattctaata cgactcacta tagggagaag gcttgaaggt ccaggtctgt ttcca         55

SEQ ID NO: 101         moltype = DNA   length = 24
FEATURE                Location/Qualifiers
source                 1..24
                       mol_type = other DNA
                       organism = synthetic construct
SEQUENCE: 101
gagcgattag cagagaactg acca                                          24

SEQ ID NO: 102         moltype = RNA   length = 148
FEATURE                Location/Qualifiers
source                 1..148
                       mol_type = other RNA
                       organism = synthetic construct
SEQUENCE: 102
gggattgctt tcaggccaag gacccatgaa attggtgatg gctttcatag catttctaag   60
atttctagcc atacccccaa cagcaggaat tttggctaga tggagctcat tcaagaagaa   120
tggagcgatc aaagtgttac ggggtttc                                      148

SEQ ID NO: 103         moltype = DNA   length = 54
FEATURE                Location/Qualifiers
source                 1..54
                       mol_type = other DNA
                       organism = synthetic construct
SEQUENCE: 103
aattctaata cgactcacta tagggagaag gccaaggacc catgaaattg gtga          54

SEQ ID NO: 104         moltype = DNA   length = 22
FEATURE                Location/Qualifiers
source                 1..22
                       mol_type = other DNA
                       organism = synthetic construct
SEQUENCE: 104
ccgtaacact ttgatcgctc ca                                            22

SEQ ID NO: 105         moltype = RNA   length = 208
FEATURE                Location/Qualifiers
source                 1..208
                       mol_type = other RNA
                       organism = synthetic construct
SEQUENCE: 105
gggattcatt tcacatctgc tctatagcct gtaccgtcag cgttattgac gccgcgccca   60
tagtgcttcc tgtcactaac gaggacgggc caggcgttct gcgattcttc aattaaggtg   120
tatatttctc ttgtgtaatt acctcaattg atgaatcaaa gaacaataga ggagatgaca   180
aatgaataac ctggcggcag cgcaaaag                                      208

SEQ ID NO: 106         moltype = RNA   length = 202
FEATURE                Location/Qualifiers
source                 1..202
                       mol_type = other RNA
                       organism = synthetic construct
SEQUENCE: 106
gggcaccact gctgtgcctt ggaatgctag ttggagtaat aaatctctga atgagatttg   60
ggataacatg acttggatgg agtgggaaag agaaattgac aattacacaa gagaaatata   120
caccttaatt gaagaatcgc agaaccaaca agaaaagaat gaactagact tattggaatt   180
```

-continued

```
ggataagtgg gcaagtttgt gg                                                 202

SEQ ID NO: 107          moltype = DNA   length = 50
FEATURE                 Location/Qualifiers
source                  1..50
                        mol_type = other DNA
                        organism = synthetic construct
SEQUENCE: 107
aattctaata cgactcacta tagggccttg gaatgctagt tggagtaata                   50

SEQ ID NO: 108          moltype = DNA   length = 24
FEATURE                 Location/Qualifiers
source                  1..24
                        mol_type = other DNA
                        organism = synthetic construct
SEQUENCE: 108
gttggttctg cgattcttca atta                                               24

SEQ ID NO: 109          moltype = RNA   length = 209
FEATURE                 Location/Qualifiers
source                  1..209
                        mol_type = other RNA
                        organism = synthetic construct
SEQUENCE: 109
gggagtagca cccactgagg caaaaaggag agtggtggag agagaaaaaa gagcagtggg        60
aataggagct gtgctccttg ggttcttggg agcagcagga agcactatgg gcgcggcgtc        120
aataacgctg acggtacagg ccagacaact gttgtctggt atagtgcaac agcaaagcaa        180
tttgctgagg gctatagagg cgcaacagc                                         209

SEQ ID NO: 110          moltype = DNA   length = 45
FEATURE                 Location/Qualifiers
source                  1..45
                        mol_type = other DNA
                        organism = synthetic construct
SEQUENCE: 110
aattctaata cgactcacta tagggaaaga gcagtgggaa tagga                        45

SEQ ID NO: 111          moltype = DNA   length = 24
FEATURE                 Location/Qualifiers
source                  1..24
                        mol_type = other DNA
                        organism = synthetic construct
SEQUENCE: 111
gcaaattgct ttgctgttgc acta                                               24

SEQ ID NO: 112          moltype = RNA   length = 182
FEATURE                 Location/Qualifiers
source                  1..182
                        mol_type = other RNA
                        organism = synthetic construct
SEQUENCE: 112
gggttcgtgt tgtttTagat ttcatctaaa cgaacaaact aaaatgtctg ataatggacc        60
ccaaaatcag cgaaatgcac cccgcattac gtttggtgga ccctcagatt caactggcag        120
taaccagaat ggagaacgca gtggggcgcg atcaaaacaa cgtcggcccc aaggtttacc        180
ca                                                                       182

SEQ ID NO: 113          moltype = DNA   length = 50
FEATURE                 Location/Qualifiers
source                  1..50
                        mol_type = other DNA
                        organism = synthetic construct
SEQUENCE: 113
aattctaata cgactcacta tagggagaag gacgttcgtg ttgttttaga                   50

SEQ ID NO: 114          moltype = DNA   length = 24
FEATURE                 Location/Qualifiers
source                  1..24
                        mol_type = other DNA
                        organism = synthetic construct
SEQUENCE: 114
ttattgggta aaccttgggg ccga                                               24

SEQ ID NO: 115          moltype = RNA   length = 182
FEATURE                 Location/Qualifiers
source                  1..182
                        mol_type = other RNA
                        organism = synthetic construct
SEQUENCE: 115
gggtgggtaa accttggggc cgacgttgtt ttgatcgcgc cccactgcgt tctccattct        60
```

-continued

```
ggttactgcc agttgaatct gagggtccac caaacgtaat gcggggtgca tttcgctgat    120
tttggggtcc attatcagac attttagttt gttcgtttag atgaaatcta aaacaacacg    180
aa                                                                    182

SEQ ID NO: 116          moltype = DNA   length = 55
FEATURE                 Location/Qualifiers
source                  1..55
                        mol_type = other DNA
                        organism = synthetic construct
SEQUENCE: 116
aattctaata cgactcacta tagggagaag gatgttgagt gagagcggtg aacca            55

SEQ ID NO: 117          moltype = DNA   length = 23
FEATURE                 Location/Qualifiers
source                  1..23
                        mol_type = other DNA
                        organism = synthetic construct
SEQUENCE: 117
gaccccaaaa tcagcgaaat gca                                               23

SEQ ID NO: 118          moltype = RNA   length = 183
FEATURE                 Location/Qualifiers
source                  1..183
                        mol_type = other RNA
                        organism = synthetic construct
SEQUENCE: 118
gggcacctgt gtaggtcaac cacgttcccg aaggtgtgac ttccatgcca atgcgcgaca     60
ttccgaagaa cgctgaagcg ctgggggcaa attgtgcaat ttgcggccaa tgtttgtaat    120
cagttccttg tctgattagt tcctggtccc caaaatttcc ttgggtttgt tctggaccac    180
gtc                                                                    183

SEQ ID NO: 119          moltype = DNA   length = 54
FEATURE                 Location/Qualifiers
source                  1..54
                        mol_type = other DNA
                        organism = synthetic construct
SEQUENCE: 119
aattctaata cgactcacta tagggagaag gtttgatggc acctgtgtag gtca             54

SEQ ID NO: 120          moltype = DNA   length = 23
FEATURE                 Location/Qualifiers
source                  1..23
                        mol_type = other DNA
                        organism = synthetic construct
SEQUENCE: 120
aagctttcgg cagacgtggt cca                                               23

SEQ ID NO: 121          moltype = RNA   length = 93
FEATURE                 Location/Qualifiers
source                  1..93
                        mol_type = other RNA
                        organism = synthetic construct
SEQUENCE: 121
gggtctatct atttcacatc tcctaagttt ccgtattcta tacagaaaca gaggagatga     60
caaatgaata gaaacctggc ggcagcgcaa aag                                   93

SEQ ID NO: 122          moltype = RNA   length = 96
FEATURE                 Location/Qualifiers
source                  1..96
                        mol_type = other RNA
                        organism = synthetic construct
SEQUENCE: 122
gggtctatct atttcacatc tcctaagttt ccgtattctg tgatacagaa acagaggaga     60
tgacaaatga atagaaacct ggcggcagcg caaaag                                96

SEQ ID NO: 123          moltype = RNA   length = 99
FEATURE                 Location/Qualifiers
source                  1..99
                        mol_type = other RNA
                        organism = synthetic construct
SEQUENCE: 123
gggtctatct atttcacatc tcctaagttt ccgtattctg tgaagataca gaaacagagg     60
agatgacaaa tgaatagaaa cctggcggca gcgcaaaag                             99

SEQ ID NO: 124          moltype = RNA   length = 102
FEATURE                 Location/Qualifiers
source                  1..102
                        mol_type = other RNA
                        organism = synthetic construct
```

-continued

```
SEQUENCE: 124
gggtctatct atttcacatc tcctaagttt ccgtattctg tgaagcccat acagaaacag   60
aggagatgac aaatgaatag aaacctggcg gcagcgcaaa ag                      102

SEQ ID NO: 125            moltype = RNA   length = 105
FEATURE                   Location/Qualifiers
source                    1..105
                          mol_type = other RNA
                          organism = synthetic construct
SEQUENCE: 125
gggtctatct atttcacatc tcctaagttt ccgtattctg tgaagccta gatacagaaa    60
cagaggagat gacaaatgaa tagaaacctg gcggcagcgc aaaag                   105

SEQ ID NO: 126            moltype = RNA   length = 108
FEATURE                   Location/Qualifiers
source                    1..108
                          mol_type = other RNA
                          organism = synthetic construct
SEQUENCE: 126
gggtctatct atttcacatc tcctaagttt ccgtattctg tgaagccta gggtatacag    60
aaacagagga gatgacaaat gaatagaaac ctggcggcag cgcaaaag                108

SEQ ID NO: 127            moltype = RNA   length = 96
FEATURE                   Location/Qualifiers
source                    1..96
                          mol_type = other RNA
                          organism = synthetic construct
SEQUENCE: 127
gggtagtgcc atatcttatc tcctgagttt catcttaaag tcaagacgaa acagaggaga    60
taacatatga cactaaacct ggcggcagcg caaaag                             96

SEQ ID NO: 128            moltype = RNA   length = 96
FEATURE                   Location/Qualifiers
source                    1..96
                          mol_type = other RNA
                          organism = synthetic construct
SEQUENCE: 128
gggtagtgcc atatcttatc tcctgagttt catcttaaag tcaagacgaa acagaggaga    60
taacatatga cactaaacct ggcggcagcg caaaag                             96

SEQ ID NO: 129            moltype = RNA   length = 99
FEATURE                   Location/Qualifiers
source                    1..99
                          mol_type = other RNA
                          organism = synthetic construct
SEQUENCE: 129
gggtagtgcc atatcttatc tcctgagttt catcttaaag tccttaagac gaaacagagg    60
agataacata tgacactaaa cctggcggca gcgcaaaag                          99

SEQ ID NO: 130            moltype = RNA   length = 102
FEATURE                   Location/Qualifiers
source                    1..102
                          mol_type = other RNA
                          organism = synthetic construct
SEQUENCE: 130
gggtagtgcc atatcttatc tcctgagttt catcttaaag tccttgtaaa gacgaaacag    60
aggagataac atatgacact aaacctggcg gcagcgcaaa ag                      102

SEQ ID NO: 131            moltype = RNA   length = 105
FEATURE                   Location/Qualifiers
source                    1..105
                          mol_type = other RNA
                          organism = synthetic construct
SEQUENCE: 131
gggtagtgcc atatcttatc tcctgagttt catcttaaag tccttgtaac aaagacgaaa    60
cagaggagat aacatatgac actaaacctg gcggcagcgc aaaag                   105

SEQ ID NO: 132            moltype = RNA   length = 108
FEATURE                   Location/Qualifiers
source                    1..108
                          mol_type = other RNA
                          organism = synthetic construct
SEQUENCE: 132
gggtagtgcc atatcttatc tcctgagttt catcttaaag tccttgtaac agtcaagacg    60
aaacagagga gataacatat gacactaaac ctggcggcag cgcaaaag                108

SEQ ID NO: 133            moltype = RNA   length = 34
FEATURE                   Location/Qualifiers
source                    1..34
```

```
                              mol_type = other RNA
                              organism = synthetic construct
SEQUENCE: 133
gggcggaccc tagggcttca cagaatacgg aaac                                    34

SEQ ID NO: 134          moltype = RNA   length = 13
FEATURE                 Location/Qualifiers
source                  1..13
                        mol_type = other RNA
                        organism = synthetic construct
SEQUENCE: 134
gggcggaccc tag                                                           13

SEQ ID NO: 135          moltype = RNA   length = 15
FEATURE                 Location/Qualifiers
source                  1..15
                        mol_type = other RNA
                        organism = synthetic construct
SEQUENCE: 135
gggcggaccc taggg                                                         15

SEQ ID NO: 136          moltype = RNA   length = 17
FEATURE                 Location/Qualifiers
source                  1..17
                        mol_type = other RNA
                        organism = synthetic construct
SEQUENCE: 136
gggcggaccc tagggct                                                       17

SEQ ID NO: 137          moltype = RNA   length = 19
FEATURE                 Location/Qualifiers
source                  1..19
                        mol_type = other RNA
                        organism = synthetic construct
SEQUENCE: 137
gggcggaccc tagggcttc                                                     19

SEQ ID NO: 138          moltype = RNA   length = 21
FEATURE                 Location/Qualifiers
source                  1..21
                        mol_type = other RNA
                        organism = synthetic construct
SEQUENCE: 138
gggcggaccc tagggcttca c                                                  21

SEQ ID NO: 139          moltype = RNA   length = 22
FEATURE                 Location/Qualifiers
source                  1..22
                        mol_type = other RNA
                        organism = synthetic construct
SEQUENCE: 139
gggcggaccc tagggcttca ca                                                 22

SEQ ID NO: 140          moltype = RNA   length = 23
FEATURE                 Location/Qualifiers
source                  1..23
                        mol_type = other RNA
                        organism = synthetic construct
SEQUENCE: 140
gggcggaccc tagggcttca cag                                                23

SEQ ID NO: 141          moltype = RNA   length = 24
FEATURE                 Location/Qualifiers
source                  1..24
                        mol_type = other RNA
                        organism = synthetic construct
SEQUENCE: 141
gggcggaccc tagggcttca caga                                               24

SEQ ID NO: 142          moltype = RNA   length = 25
FEATURE                 Location/Qualifiers
source                  1..25
                        mol_type = other RNA
                        organism = synthetic construct
SEQUENCE: 142
gggcggaccc tagggcttca cagaa                                              25

SEQ ID NO: 143          moltype = RNA   length = 26
FEATURE                 Location/Qualifiers
```

```
source                      1..26
                            mol_type = other RNA
                            organism = synthetic construct
SEQUENCE: 143
gggcggaccc tagggcttca cagaat                                                    26

SEQ ID NO: 144              moltype = RNA   length = 27
FEATURE                     Location/Qualifiers
source                      1..27
                            mol_type = other RNA
                            organism = synthetic construct
SEQUENCE: 144
gggcggaccc tagggcttca cagaata                                                   27

SEQ ID NO: 145              moltype = RNA   length = 28
FEATURE                     Location/Qualifiers
source                      1..28
                            mol_type = other RNA
                            organism = synthetic construct
SEQUENCE: 145
gggcggaccc tagggcttca cagaatac                                                  28

SEQ ID NO: 146              moltype = RNA   length = 30
FEATURE                     Location/Qualifiers
source                      1..30
                            mol_type = other RNA
                            organism = synthetic construct
SEQUENCE: 146
gggcggaccc tagggcttca cagaatacgg                                                30

SEQ ID NO: 147              moltype = RNA   length = 32
FEATURE                     Location/Qualifiers
source                      1..32
                            mol_type = other RNA
                            organism = synthetic construct
SEQUENCE: 147
gggcggaccc tagggcttca cagaatacgg aa                                             32

SEQ ID NO: 148              moltype = RNA   length = 13
FEATURE                     Location/Qualifiers
source                      1..13
                            mol_type = other RNA
                            organism = synthetic construct
SEQUENCE: 148
gggatacgga aac                                                                  13

SEQ ID NO: 149              moltype = RNA   length = 14
FEATURE                     Location/Qualifiers
source                      1..14
                            mol_type = other RNA
                            organism = synthetic construct
SEQUENCE: 149
gggaatacgg aaac                                                                 14

SEQ ID NO: 150              moltype = RNA   length = 17
FEATURE                     Location/Qualifiers
source                      1..17
                            mol_type = other RNA
                            organism = synthetic construct
SEQUENCE: 150
gggcagaata cggaaac                                                              17

SEQ ID NO: 151              moltype = RNA   length = 19
FEATURE                     Location/Qualifiers
source                      1..19
                            mol_type = other RNA
                            organism = synthetic construct
SEQUENCE: 151
gggcacagaa tacggaaac                                                            19

SEQ ID NO: 152              moltype = RNA   length = 21
FEATURE                     Location/Qualifiers
source                      1..21
                            mol_type = other RNA
                            organism = synthetic construct
SEQUENCE: 152
gggttcacag aatacggaaa c                                                         21

SEQ ID NO: 153              moltype = RNA   length = 28
```

-continued

```
FEATURE            Location/Qualifiers
source             1..28
                   mol_type = other RNA
                   organism = synthetic construct
SEQUENCE: 153
gggctagggc ttcacagaat acggaaac                                      28

SEQ ID NO: 154     moltype = RNA   length = 29
FEATURE            Location/Qualifiers
source             1..29
                   mol_type = other RNA
                   organism = synthetic construct
SEQUENCE: 154
gggcctaggg cttcacagaa tacggaaac                                     29

SEQ ID NO: 155     moltype = RNA   length = 30
FEATURE            Location/Qualifiers
source             1..30
                   mol_type = other RNA
                   organism = synthetic construct
SEQUENCE: 155
gggccctagg gcttcacaga atacggaaac                                    30

SEQ ID NO: 156     moltype = RNA   length = 31
FEATURE            Location/Qualifiers
source             1..31
                   mol_type = other RNA
                   organism = synthetic construct
SEQUENCE: 156
gggaccctag ggcttcacag aatacggaaa c                                  31

SEQ ID NO: 157     moltype = RNA   length = 33
FEATURE            Location/Qualifiers
source             1..33
                   mol_type = other RNA
                   organism = synthetic construct
SEQUENCE: 157
gggacgactg ttacaaggac tttaagatga aac                                33

SEQ ID NO: 158     moltype = RNA   length = 12
FEATURE            Location/Qualifiers
source             1..12
                   mol_type = other RNA
                   organism = synthetic construct
SEQUENCE: 158
gggacgactg tt                                                       12

SEQ ID NO: 159     moltype = RNA   length = 14
FEATURE            Location/Qualifiers
source             1..14
                   mol_type = other RNA
                   organism = synthetic construct
SEQUENCE: 159
gggacgactg ttac                                                     14

SEQ ID NO: 160     moltype = RNA   length = 16
FEATURE            Location/Qualifiers
source             1..16
                   mol_type = other RNA
                   organism = synthetic construct
SEQUENCE: 160
gggacgactg ttacaa                                                   16

SEQ ID NO: 161     moltype = RNA   length = 18
FEATURE            Location/Qualifiers
source             1..18
                   mol_type = other RNA
                   organism = synthetic construct
SEQUENCE: 161
gggacgactg ttacaagg                                                 18

SEQ ID NO: 162     moltype = RNA   length = 20
FEATURE            Location/Qualifiers
source             1..20
                   mol_type = other RNA
                   organism = synthetic construct
SEQUENCE: 162
gggacgactg ttacaaggac                                               20
```

-continued

```
SEQ ID NO: 163          moltype = RNA  length = 21
FEATURE                 Location/Qualifiers
source                  1..21
                        mol_type = other RNA
                        organism = synthetic construct
SEQUENCE: 163
gggacgactg ttacaaggac t                                          21

SEQ ID NO: 164          moltype = RNA  length = 22
FEATURE                 Location/Qualifiers
source                  1..22
                        mol_type = other RNA
                        organism = synthetic construct
SEQUENCE: 164
gggacgactg ttacaaggac tt                                         22

SEQ ID NO: 165          moltype = RNA  length = 23
FEATURE                 Location/Qualifiers
source                  1..23
                        mol_type = other RNA
                        organism = synthetic construct
SEQUENCE: 165
gggacgactg ttacaaggac ttt                                        23

SEQ ID NO: 166          moltype = RNA  length = 24
FEATURE                 Location/Qualifiers
source                  1..24
                        mol_type = other RNA
                        organism = synthetic construct
SEQUENCE: 166
gggacgactg ttacaaggac ttta                                       24

SEQ ID NO: 167          moltype = RNA  length = 25
FEATURE                 Location/Qualifiers
source                  1..25
                        mol_type = other RNA
                        organism = synthetic construct
SEQUENCE: 167
gggacgactg ttacaaggac tttaa                                      25

SEQ ID NO: 168          moltype = RNA  length = 26
FEATURE                 Location/Qualifiers
source                  1..26
                        mol_type = other RNA
                        organism = synthetic construct
SEQUENCE: 168
gggacgactg ttacaaggac tttaag                                     26

SEQ ID NO: 169          moltype = RNA  length = 27
FEATURE                 Location/Qualifiers
source                  1..27
                        mol_type = other RNA
                        organism = synthetic construct
SEQUENCE: 169
gggacgactg ttacaaggac tttaaga                                    27

SEQ ID NO: 170          moltype = RNA  length = 29
FEATURE                 Location/Qualifiers
source                  1..29
                        mol_type = other RNA
                        organism = synthetic construct
SEQUENCE: 170
gggacgactg ttacaaggac tttaagatg                                  29

SEQ ID NO: 171          moltype = RNA  length = 31
FEATURE                 Location/Qualifiers
source                  1..31
                        mol_type = other RNA
                        organism = synthetic construct
SEQUENCE: 171
gggacgactg ttacaaggac tttaagatga a                               31

SEQ ID NO: 172          moltype = RNA  length = 13
FEATURE                 Location/Qualifiers
source                  1..13
                        mol_type = other RNA
                        organism = synthetic construct
SEQUENCE: 172
gggaagatga aac                                                   13
```

-continued

```
SEQ ID NO: 173            moltype = RNA   length = 15
FEATURE                   Location/Qualifiers
source                    1..15
                          mol_type = other RNA
                          organism = synthetic construct
SEQUENCE: 173
gggttaagat gaaac                                                 15

SEQ ID NO: 174            moltype = RNA   length = 17
FEATURE                   Location/Qualifiers
source                    1..17
                          mol_type = other RNA
                          organism = synthetic construct
SEQUENCE: 174
gggctttaag atgaaac                                               17

SEQ ID NO: 175            moltype = RNA   length = 18
FEATURE                   Location/Qualifiers
source                    1..18
                          mol_type = other RNA
                          organism = synthetic construct
SEQUENCE: 175
gggactttaa gatgaaac                                              18

SEQ ID NO: 176            moltype = RNA   length = 21
FEATURE                   Location/Qualifiers
source                    1..21
                          mol_type = other RNA
                          organism = synthetic construct
SEQUENCE: 176
gggaggactt taagatgaaa c                                          21

SEQ ID NO: 177            moltype = RNA   length = 23
FEATURE                   Location/Qualifiers
source                    1..23
                          mol_type = other RNA
                          organism = synthetic construct
SEQUENCE: 177
gggcaaggac tttaagatga aac                                        23

SEQ ID NO: 178            moltype = RNA   length = 24
FEATURE                   Location/Qualifiers
source                    1..24
                          mol_type = other RNA
                          organism = synthetic construct
SEQUENCE: 178
gggacaagga ctttaagatg aaac                                       24

SEQ ID NO: 179            moltype = RNA   length = 25
FEATURE                   Location/Qualifiers
source                    1..25
                          mol_type = other RNA
                          organism = synthetic construct
SEQUENCE: 179
gggtacaagg actttaagat gaaac                                      25

SEQ ID NO: 180            moltype = RNA   length = 26
FEATURE                   Location/Qualifiers
source                    1..26
                          mol_type = other RNA
                          organism = synthetic construct
SEQUENCE: 180
gggttacaag gactttaaga tgaaac                                     26

SEQ ID NO: 181            moltype = RNA   length = 28
FEATURE                   Location/Qualifiers
source                    1..28
                          mol_type = other RNA
                          organism = synthetic construct
SEQUENCE: 181
gggtgttaca aggactttaa gatgaaac                                   28

SEQ ID NO: 182            moltype = RNA   length = 29
FEATURE                   Location/Qualifiers
source                    1..29
                          mol_type = other RNA
                          organism = synthetic construct
SEQUENCE: 182
```

-continued

```
gggctgttac aaggacttta agatgaaac                                    29

SEQ ID NO: 183           moltype = RNA   length = 30
FEATURE                  Location/Qualifiers
source                   1..30
                         mol_type = other RNA
                         organism = synthetic construct
SEQUENCE: 183
gggactgtta caaggacttt aagatgaaac                                   30

SEQ ID NO: 184           moltype = RNA   length = 32
FEATURE                  Location/Qualifiers
source                   1..32
                         mol_type = other RNA
                         organism = synthetic construct
SEQUENCE: 184
gggcgactgt tacaaggact ttaagatgaa ac                                32

SEQ ID NO: 185           moltype = DNA   length = 20
FEATURE                  Location/Qualifiers
source                   1..20
                         mol_type = other DNA
                         organism = synthetic construct
SEQUENCE: 185
aggtgatgca acatacggaa                                              20

SEQ ID NO: 186           moltype = DNA   length = 20
FEATURE                  Location/Qualifiers
source                   1..20
                         mol_type = other DNA
                         organism = synthetic construct
SEQUENCE: 186
tgatctgggt atctcgcaaa                                              20

SEQ ID NO: 187           moltype = DNA   length = 20
FEATURE                  Location/Qualifiers
source                   1..20
                         mol_type = other DNA
                         organism = synthetic construct
SEQUENCE: 187
cccagatcac atgaaacagc                                              20

SEQ ID NO: 188           moltype = DNA   length = 20
FEATURE                  Location/Qualifiers
source                   1..20
                         mol_type = other DNA
                         organism = synthetic construct
SEQUENCE: 188
gcacgtgtct tgtagttccc                                              20

SEQ ID NO: 189           moltype = DNA   length = 20
FEATURE                  Location/Qualifiers
source                   1..20
                         mol_type = other DNA
                         organism = synthetic construct
SEQUENCE: 189
cgcaaccctt atcctttgtt                                              20

SEQ ID NO: 190           moltype = DNA   length = 20
FEATURE                  Location/Qualifiers
source                   1..20
                         mol_type = other DNA
                         organism = synthetic construct
SEQUENCE: 190
taagggccat gatgacttga                                              20

SEQ ID NO: 191           moltype = DNA   length = 20
FEATURE                  Location/Qualifiers
source                   1..20
                         mol_type = other DNA
                         organism = synthetic construct
SEQUENCE: 191
acaatggcgc atacaaagag                                              20

SEQ ID NO: 192           moltype = DNA   length = 20
FEATURE                  Location/Qualifiers
source                   1..20
                         mol_type = other DNA
                         organism = synthetic construct
```

```
SEQUENCE: 192
gtattcaccg tggcattctg                                                    20

SEQ ID NO: 193          moltype = RNA   length = 248
FEATURE                 Location/Qualifiers
source                  1..248
                        mol_type = other RNA
                        organism = synthetic construct
SEQUENCE: 193
gggactcaaa tcttcgctac agcgacatct acacattacg tttggtggac cctcagattc    60
aactaaacct aatgggtaga actcgctaaa gcgatgtcta cctgccatat cttatctcct   120
gaatcagttc cttgtctgat tagttcctgg aggaactgat agaggagata caatatggca   180
attagacaag atacgagtaa cctggcggca gcgcaaaaga tgcgtaaagg agaagaactt   240
ttcactgg                                                             248

SEQ ID NO: 194          moltype = RNA   length = 248
FEATURE                 Location/Qualifiers
source                  1..248
                        mol_type = other RNA
                        organism = synthetic construct
SEQUENCE: 194
gggactcaaa tcttcgctac agcgacatct acaggaactg attacaaaca ttggccgcaa    60
attgaatctg ttccggtaga actcgctaaa gcgatgtcta cctgccatat cttatctcct   120
gactgcgttc tccattctgg ttactgccag gagaacgcag agaggagata caatatggca   180
attagacaag atacgagtaa cctggcggca gcgcaaaaga tgcgtaaagg agaagaactt   240
ttcactgg                                                             248

SEQ ID NO: 195          moltype = RNA   length = 248
FEATURE                 Location/Qualifiers
source                  1..248
                        mol_type = other RNA
                        organism = synthetic construct
SEQUENCE: 195
gggactcaaa tcttcgctac agcgacatct acactgcgtt ctccattctg gttactgcca    60
gttggagacc gcagggtaga actcgctaaa gcgatgtcta cctgccatat cttatctcct   120
gaactgatta caaacattgg ccgcaaattg tgtattcagt agaggagata caatatggca   180
attagacaag atacgagtaa cctggcggca gcgcaaaaga tgcgtaaagg agaagaactt   240
ttcactgg                                                             248

SEQ ID NO: 196          moltype = RNA   length = 248
FEATURE                 Location/Qualifiers
source                  1..248
                        mol_type = other RNA
                        organism = synthetic construct
SEQUENCE: 196
gggactcaaa tcttcgctac agcgacatct acactgcgtt ctccattctg gttactgcca    60
gttggagacc gcagggtaga actcgctaaa gcgatgtcta cctgccatat cttatctcct   120
gaaatttgcg gccaatgttt gtaatcagtt gccgcaaatt agaggagata caatatggca   180
attagacaag atacgagtaa cctggcggca gcgcaaaaga tgcgtaaagg agaagaactt   240
ttcactgg                                                             248

SEQ ID NO: 197          moltype = RNA   length = 248
FEATURE                 Location/Qualifiers
source                  1..248
                        mol_type = other RNA
                        organism = synthetic construct
SEQUENCE: 197
gggactcaaa tcttcgctac agcgacatct acacattacg tttggtggac cctcagattc    60
aactaaacct aatgggtaga actcgctaaa gcgatgtcta cctgccatat cttatctcct   120
gaactgatta caaacattgg ccgcaaattg tgtattcagt agaggagata caatatggca   180
attagacaag atacgagtaa cctggcggca gcgcaaaaga tgcgtaaagg agaagaactt   240
ttcactgg                                                             248

SEQ ID NO: 198          moltype = RNA   length = 248
FEATURE                 Location/Qualifiers
source                  1..248
                        mol_type = other RNA
                        organism = synthetic construct
SEQUENCE: 198
gggactcaaa tcttcgctac agcgacatct acacggccaa tgtttgtaat cagttccttg    60
tctgacatcg gccgggtaga actcgctaaa gcgatgtcta cctgccatat cttatctcct   120
gattagattt catctaaacg aacaaactaa tgaaatctaa agaggagata caatatggca   180
attagacaag atacgagtaa cctggcggca gcgcaaaaga tgcgtaaagg agaagaactt   240
ttcactgg                                                             248

SEQ ID NO: 199          moltype = RNA   length = 248
FEATURE                 Location/Qualifiers
source                  1..248
                        mol_type = other RNA
```

```
                        organism = synthetic construct
SEQUENCE: 199
gggactcaaa tcttcgctac agcgacatct cacggccaa tgtttgtaat cagttccttg    60
tctgacatgg gccgggtaga actcgctaaa gcgatgtcta cctgccatat cttatctcct   120
gagcgttctc cattctggtt actgccagtt tggagaacgc agaggagata caatatggca   180
attagacaag atacgagtaa cctggcggca gcgcaaaaga tgcgtaaagg agaagaactt   240
ttcactgg                                                            248

SEQ ID NO: 200          moltype = RNA   length = 248
FEATURE                 Location/Qualifiers
source                  1..248
                        mol_type = other RNA
                        organism = synthetic construct
SEQUENCE: 200
gggactcaaa tcttcgctac agcgacatct acaggaactg attacaaaca ttggccgcaa    60
attgaatctg ttccggtaga actcgctaaa gcgatgtcta cctgccatat cttatctcct   120
gattagattt catctaaacg aacaaactaa tgaaatctaa agaggagata caatatggca   180
attagacaag atacgagtaa cctggcggca gcgcaaaaga tgcgtaaagg agaagaactt   240
ttcactgg                                                            248

SEQ ID NO: 201          moltype = RNA   length = 219
FEATURE                 Location/Qualifiers
source                  1..219
                        mol_type = other RNA
                        organism = synthetic construct
SEQUENCE: 201
gggactcaaa tcttcgctac agcgacatct acagccatga gcctgttcca tatgtacctg    60
aagtggctga tggcggtaga actcgctaaa gcgatgtcta cctgccatat cttatctcct   120
gattgtgtcc gcatatgcag ctgtaaatgt gcggacacaa agaggagata caatatggca   180
attagacaag atacgagtaa cctggcggca gcgcaaaag                          219

SEQ ID NO: 202          moltype = RNA   length = 219
FEATURE                 Location/Qualifiers
source                  1..219
                        mol_type = other RNA
                        organism = synthetic construct
SEQUENCE: 202
gggactcaaa tcttcgctac agcgacatct acaaagatat gctgctccca ctagtccaaa    60
ttgtagcaaa tcttggtaga actcgctaaa gcgatgtcta cctgccatat cttatctcct   120
gaatgataac caatgcaaat atgatcgctt tggtcatcat agaggagata caatatggca   180
attagacaag atacgagtaa cctggcggca gcgcaaaag                          219

SEQ ID NO: 203          moltype = RNA   length = 216
FEATURE                 Location/Qualifiers
source                  1..216
                        mol_type = other RNA
                        organism = synthetic construct
SEQUENCE: 203
gggactcaaa tcttcgctac agcgacatct acagctcccg ctagtccaga ttgtgttctc    60
ttcgtagctg gagcggtaga actcgctaaa gcgatgtcta cctgccatat cttatctcct   120
gacagtgtct gttgaattgt tcgcatgaca gacactgaga ggagatacaa tatggcaatt   180
agacaagata cgagtaacct ggcggcagcg caaaag                            216

SEQ ID NO: 204          moltype = RNA   length = 123
FEATURE                 Location/Qualifiers
source                  1..123
                        mol_type = other RNA
                        organism = synthetic construct
SEQUENCE: 204
gggtacattt acaaccgcaa atgcagacac attatgtata ggttatcatg cgaacaattc    60
aacagacact gtagacacag tactagaaaa gaatgtaaca gtaacacact ctgttaatct   120
tct                                                                 123

SEQ ID NO: 205          moltype = RNA   length = 123
FEATURE                 Location/Qualifiers
source                  1..123
                        mol_type = other RNA
                        organism = synthetic construct
SEQUENCE: 205
gggtacattt acagctgcat atgcggacac aatatgtata ggataccatg ccaacaactc    60
aaccgacact gttgacacag tacttgaaaa gaatgtgaca gtgacccact ctgtcaacct   120
act                                                                 123

SEQ ID NO: 206          moltype = RNA   length = 123
FEATURE                 Location/Qualifiers
source                  1..123
                        mol_type = other RNA
                        organism = synthetic construct
SEQUENCE: 206
```

-continued

```
gggtctatgt ctggtttcg ctcaaaaaat tcctggaaat gacaatagca cggcaacgct   60
gtgccttggg caccatgcag taccaaacgg aacgatagtg aaaacaatca caaatgaccg   120
aat                                                                 123

SEQ ID NO: 207           moltype = RNA   length = 123
FEATURE                  Location/Qualifiers
source                   1..123
                         mol_type = other RNA
                         organism = synthetic construct
SEQUENCE: 207
gggaatcagc cttgtcaaaa gcgatcatat ttgcattggt tatcatgcaa ataactcgac   60
agagcaggtt gacacaataa tggaaaagaa cgttactgtt acacatgccc aagacatact   120
gga                                                                 123

SEQ ID NO: 208           moltype = RNA   length = 201
FEATURE                  Location/Qualifiers
source                   1..201
                         mol_type = other RNA
                         organism = synthetic construct
SEQUENCE: 208
gggagttttg ttcagcatcc agaactaaca gggctggatt gtataagacc ttgcttctgg   60
gttgaactaa taagaggacg acccgaagag aacacaatct ggactagcgg gagcagcata   120
tcctttgtg gtgtagacag tgacactgtg ggttggtctt ggccagacgg tgctgagttg    180
ccatttacca ttgacaagta a                                             201

SEQ ID NO: 209           moltype = RNA   length = 204
FEATURE                  Location/Qualifiers
source                   1..204
                         mol_type = other RNA
                         organism = synthetic construct
SEQUENCE: 209
gggtccggtt attctggcat tttctctgtc gaaggcaaaa actgcatcaa tcggtgcttt   60
tatgtggagt tgataagggg aaggaaacag gaaactgaag tcgggtggac ctcaaacagt   120
attgttgtgt tttgtgggac ttcaggtaca tatggaacag gctcatggcc tgatgggca    180
gacatcaatc tcatgcctat ataa                                          204

SEQ ID NO: 210           moltype = RNA   length = 204
FEATURE                  Location/Qualifiers
source                   1..204
                         mol_type = other RNA
                         organism = synthetic construct
SEQUENCE: 210
gggtccggtt attctggtat tttctctgtt gaaggcaaaa gctgcatcaa tcggtgcttt   60
tatgtggagt tgattagggg aagaaaagag gaaactgaag tcttgtggac ctcaaacagt   120
attgttgtgt tttgtggcac ctcaggtaca tatggaacag gctcatggcc tgatggggcg   180
gacctcaatc tcatgcatat ataa                                          204

SEQ ID NO: 211           moltype = RNA   length = 202
FEATURE                  Location/Qualifiers
source                   1..202
                         mol_type = other RNA
                         organism = synthetic construct
SEQUENCE: 211
gggagttttg tccagcaccc agaactgaca ggattagatt gcatgagacc ttgcttctgg   60
gttgagttaa tcagagggcg gcccaaagag agcacaattt ggactagtgg gagcagcata   120
tctttttgtg gtgtaaatag tgacactgtg agctggtctt ggccagacgg tgctgagttg   180
ccattcacca ttgacaagta gc                                            202

SEQ ID NO: 212           moltype = RNA   length = 29
FEATURE                  Location/Qualifiers
source                   1..29
                         mol_type = genomic RNA
                         organism = influenza virus
SEQUENCE: 212
aaagcgatca tatttgcatt ggttatcat                                     29

SEQ ID NO: 213           moltype = RNA   length = 29
FEATURE                  Location/Qualifiers
source                   1..29
                         mol_type = genomic RNA
                         organism = influenza virus
SEQUENCE: 213
aaggtgacca aatctgcatt ggttaccat                                     29

SEQ ID NO: 214           moltype = RNA   length = 32
FEATURE                  Location/Qualifiers
source                   1..32
                         mol_type = genomic RNA
                         organism = influenza virus
```

-continued

```
SEQUENCE: 214
acaatttgga ctagtgggag cagcatatct tt                                    32

SEQ ID NO: 215            moltype = RNA   length = 32
FEATURE                   Location/Qualifiers
source                    1..32
                          mol_type = genomic RNA
                          organism = influenza virus
SEQUENCE: 215
acaatctgga ctagcgggag cagcatatcc tt                                    32

SEQ ID NO: 216            moltype = RNA   length = 27
FEATURE                   Location/Qualifiers
source                    1..27
                          mol_type = genomic RNA
                          organism = influenza virus
SEQUENCE: 216
tcatgcgaac aattcaacag acactgt                                          27

SEQ ID NO: 217            moltype = RNA   length = 27
FEATURE                   Location/Qualifiers
source                    1..27
                          mol_type = genomic RNA
                          organism = influenza virus
SEQUENCE: 217
ccatgccaac aactcaaccg acactgt                                          27

SEQ ID NO: 218            moltype = RNA   length = 31
FEATURE                   Location/Qualifiers
source                    1..31
                          mol_type = genomic RNA
                          organism = influenza virus
SEQUENCE: 218
cgaagagaac acaatctgga ctagcgggag c                                     31

SEQ ID NO: 219            moltype = RNA   length = 31
FEATURE                   Location/Qualifiers
source                    1..31
                          mol_type = genomic RNA
                          organism = influenza virus
SEQUENCE: 219
caaagagagc acaatttgga ctagtgggag c                                     31

SEQ ID NO: 220            moltype = RNA   length = 29
FEATURE                   Location/Qualifiers
source                    1..29
                          mol_type = genomic RNA
                          organism = influenza virus
SEQUENCE: 220
acatttacag ctgcatatgc ggacacaat                                        29

SEQ ID NO: 221            moltype = RNA   length = 29
FEATURE                   Location/Qualifiers
source                    1..29
                          mol_type = genomic RNA
                          organism = influenza virus
SEQUENCE: 221
acatttacaa ccgcaaatgc agacacatt                                        29

SEQ ID NO: 222            moltype = RNA   length = 31
FEATURE                   Location/Qualifiers
source                    1..31
                          mol_type = genomic RNA
                          organism = influenza virus
SEQUENCE: 222
acttcaggta catatggaac aggctcatgg c                                     31

SEQ ID NO: 223            moltype = RNA   length = 31
FEATURE                   Location/Qualifiers
source                    1..31
                          mol_type = genomic RNA
                          organism = influenza virus
SEQUENCE: 223
acctcaggta catatggaac aggctcatgg c                                     31

SEQ ID NO: 224            moltype = RNA   length = 111
FEATURE                   Location/Qualifiers
source                    1..111
                          mol_type = other RNA
```

-continued

```
                                organism = synthetic construct
SEQUENCE: 224
gggtctatct atttcacatc tcctaagttt ccgtattctg tgaagcccta gggtccgata    60
cagaaacaga ggagatgaca aatgaataga aacctggcgg cagcgcaaaa g           111

SEQ ID NO: 225         moltype = RNA   length = 111
FEATURE                Location/Qualifiers
source                 1..111
                       mol_type = other RNA
                       organism = synthetic construct
SEQUENCE: 225
gggtcgtgct atttcacatc tcctaagttt ccgtattctg tgaagcccta gggtccgata    60
cagaaacaga ggagatgaca aatgacacga aacctggcgg cagcgcaaaa g           111

SEQ ID NO: 226         moltype = RNA   length = 111
FEATURE                Location/Qualifiers
source                 1..111
                       mol_type = other RNA
                       organism = synthetic construct
SEQUENCE: 226
gggcttatgt atttcacatc tcctaagttt ccgtattctg tgaagcccta gggtccgata    60
cagaaacaga ggagatgaca aatgaataag aacctggcgg cagcgcaaaa g           111

SEQ ID NO: 227         moltype = RNA   length = 111
FEATURE                Location/Qualifiers
source                 1..111
                       mol_type = other RNA
                       organism = synthetic construct
SEQUENCE: 227
gggtcgttgt atttcacatc tcctaagttt ccgtattctg tgaagcccta gggtccgata    60
cagaaacaga ggagatgaca aatggaacga aacctggcgg cagcgcaaaa g           111

SEQ ID NO: 228         moltype = RNA   length = 111
FEATURE                Location/Qualifiers
source                 1..111
                       mol_type = other RNA
                       organism = synthetic construct
SEQUENCE: 228
gggcttgtct atttcacatc tcctaagttt ccgtattctg tgaagcccta gggtccgata    60
cagaaacaga ggagatgaca aatgaacaag aacctggcgg cagcgcaaaa g           111

SEQ ID NO: 229         moltype = RNA   length = 62
FEATURE                Location/Qualifiers
source                 1..62
                       mol_type = other RNA
                       organism = synthetic construct
SEQUENCE: 229
gggtgaatga attgtaggct tgttatagtt atgaacagag gagacataac atgaacaagc    60
ct                                                                  62

SEQ ID NO: 230         moltype = RNA   length = 62
FEATURE                Location/Qualifiers
source                 1..62
                       mol_type = other RNA
                       organism = synthetic construct
SEQUENCE: 230
gggtataagt aaatcgcttg ctgtatgtcg ttaaacagag gagataacga atgacagcaa    60
gc                                                                  62

SEQ ID NO: 231         moltype = RNA   length = 62
FEATURE                Location/Qualifiers
source                 1..62
                       mol_type = other RNA
                       organism = synthetic construct
SEQUENCE: 231
gggtgaattt gattgactag aatgatgata cgaaacagag gagatcgtat atgcattcta    60
gt                                                                  62

SEQ ID NO: 232         moltype = RNA   length = 69
FEATURE                Location/Qualifiers
source                 1..69
                       mol_type = other RNA
                       organism = synthetic construct
SEQUENCE: 232
gggtatgtaa ttgatttggc ttctgttagt ttcatacaag aacagaggag atatgaaatg    60
aacagaagc                                                           69
```